(12) United States Patent
Aussant et al.

(10) Patent No.: US 10,537,868 B2
(45) Date of Patent: Jan. 21, 2020

(54) MICROCAPSULES

(71) Applicant: Givaudan, S.A., Vernier (CH)

(72) Inventors: Emmanuel Aussant, Paris (FR); Ian Michael Harrison, Poissy (FR)

(73) Assignee: Givaudan S.A., Vernier (CH)

( * ) Notice: Subject to any disclaimer, the term of this patent is extended or adjusted under 35 U.S.C. 154(b) by 107 days.

(21) Appl. No.: 15/736,378

(22) PCT Filed: Jul. 1, 2016

(86) PCT No.: PCT/EP2016/065538
§ 371 (c)(1),
(2) Date: Dec. 14, 2017

(87) PCT Pub. No.: WO2017/001672
PCT Pub. Date: Jan. 5, 2017

(65) Prior Publication Data
US 2018/0185808 A1   Jul. 5, 2018

(30) Foreign Application Priority Data

Jul. 2, 2015 (GB) .................................. 1511605.6

(51) Int. Cl.
| | | |
|---|---|---|
| *C11D 3/50* | (2006.01) | |
| *B01J 13/14* | (2006.01) | |
| *A61K 8/11* | (2006.01) | |
| *A61K 8/84* | (2006.01) | |
| *A61Q 13/00* | (2006.01) | |
| *A61K 8/04* | (2006.01) | |
| *B01J 13/22* | (2006.01) | |

(52) U.S. Cl.
CPC ............... *B01J 13/14* (2013.01); *A61K 8/04* (2013.01); *A61K 8/11* (2013.01); *A61K 8/84* (2013.01); *A61Q 13/00* (2013.01); *B01J 13/22* (2013.01); *C11D 3/505* (2013.01)

(58) Field of Classification Search
CPC ............................ C11D 3/505; C11D 17/0039
See application file for complete search history.

(56) References Cited

U.S. PATENT DOCUMENTS

| | | |
|---|---|---|
| 2,220,099 A | 11/1940 | Guenther et al. |
| 2,477,383 A | 7/1949 | Lewis et al. |
| 3,664,961 A | 5/1972 | Norris |
| 3,919,678 A | 11/1975 | Penfold |
| 4,222,905 A | 9/1980 | Cockrell, Jr. |
| 4,239,659 A | 12/1980 | Murphy |
| 4,246,612 A | 1/1981 | Berry et al. |
| 4,810,410 A | 3/1989 | Diakun et al. |
| 5,114,611 A | 5/1992 | Van Kralingen et al. |
| 5,227,084 A | 7/1993 | Martens et al. |
| 5,458,810 A | 10/1995 | Fredj et al. |
| 5,460,752 A | 10/1995 | Fredj et al. |
| 5,466,802 A | 11/1995 | Panandiker et al. |
| 5,470,507 A | 11/1995 | Fredj et al. |
| 5,574,179 A | 11/1996 | Wahl et al. |
| 5,618,523 A | 4/1997 | Zysman et al. |
| 5,661,118 A | 8/1997 | Cauwet et al. |
| 5,674,832 A | 10/1997 | Keys |
| 5,731,278 A | 3/1998 | Nair et al. |
| 5,756,436 A | 5/1998 | Royce et al. |
| 5,759,990 A | 6/1998 | Wahl et al. |
| 5,776,443 A | 7/1998 | Vinski et al. |
| 5,837,661 A | 11/1998 | Evans et al. |
| 5,877,145 A | 3/1999 | Wahl et al. |
| 5,916,862 A | 6/1999 | Morelli et al. |
| 5,929,022 A | 7/1999 | Velazquez |
| 5,932,203 A | 8/1999 | Coffindaffer et al. |

(Continued)

FOREIGN PATENT DOCUMENTS

| | | |
|---|---|---|
| CN | 102965196 A | 3/2013 |
| EP | 2 111 214 A1 | 10/2009 |

(Continued)

OTHER PUBLICATIONS

PCT/EP2016/065538—International Search Report, dated Jun. 10, 2016.
PCT/EP2016/065538—International Written Opinion, dated Jun. 10, 2016.
PCT/EP2016/065538—International Preliminary Report on Patentability, dated Jan. 2, 2018.
F. Etzweiler, et al., "Eine einfach Methode zur Bestimmung von Dampfdrücken", Berichte der Bunsengesellschaft für physikalische Chemie, Jun. 1984, pp. 578-583, vol. 88, Issue 6. English Abstract only.

*Primary Examiner* — John R Hardee
(74) *Attorney, Agent, or Firm* — Curatolo Sidoti Co., LPA; Salvatore A. Sidoti

(57) ABSTRACT

Encapsulated perfume composition comprising at least one aminoplast core-shell microcapsule dispersed in a suspending medium, the microcapsule comprising a perfume-containing core encapsulated in a shell, said shell comprising a network of cross-linked aminoplast resin, wherein 75-100% of the resin comprises 50-90%, preferably from 60-85%, of a terpolymer and from 10-50%, preferably from 10-25%, of a polymeric stabilizer; the terpolymer comprising:

(a) from 20-35 wt %, preferably 22-30% by weight of moieties derived from at least one triamine, (b) from 30-60 wt %, preferably 40-55% by weight of moieties derived from at least one diamine, (c) from 20-35 wt %, preferably 22-30% by weight of moieties derived from the group consisting of alkylene and alkylenoxy moieties having 1 to 6 methylene units, preferably 1 to 4 methylene units and most preferably 1 methylene unit.

The encapsulated perfume composition is useful for the storage and dissemination of fragrance in various products, such as laundry products and fabric care products.

19 Claims, No Drawings

(56) References Cited

U.S. PATENT DOCUMENTS

| | | |
|---|---|---|
| 5,935,561 A | 8/1999 | Inman et al. |
| 5,968,286 A | 10/1999 | Crudele et al. |
| 6,162,423 A | 12/2000 | Sebag et al. |
| 6,335,315 B1 | 1/2002 | Trinh et al. |
| 7,135,451 B2 | 11/2006 | Corona et al. |
| 7,625,857 B2 | 12/2009 | Ward et al. |
| 7,867,968 B1 | 1/2011 | Aouad |
| 8,119,587 B2 | 2/2012 | Cavin et al. |
| 8,357,651 B2 | 1/2013 | Quellet et al. |
| 8,524,650 B2 | 9/2013 | Denutte et al. |
| 9,358,189 B2 | 6/2016 | Berthier et al. |
| 9,416,339 B2 | 8/2016 | Bianchetti et al. |
| 2003/0060390 A1 | 3/2003 | Demeyere et al. |
| 2003/0126282 A1 | 7/2003 | Sarkar et al. |
| 2004/0204337 A1 | 10/2004 | Corona et al. |
| 2006/0248665 A1* | 11/2006 | Pluyter .......... A61K 8/11 8/406 |
| 2007/0138674 A1 | 6/2007 | Anastasiou et al. |
| 2007/0219111 A1 | 10/2007 | Ward et al. |
| 2008/0096780 A1 | 4/2008 | Veugelers et al. |
| 2009/0226529 A1 | 9/2009 | Quellet et al. |
| 2009/0275494 A1* | 11/2009 | Ferguson .......... B01J 13/22 510/349 |
| 2010/0009893 A1 | 1/2010 | Cavin et al. |
| 2010/0216684 A1* | 8/2010 | Ferguson .......... C11D 3/505 510/337 |
| 2010/0323938 A1 | 12/2010 | Quellet et al. |
| 2011/0152146 A1 | 8/2011 | Denutte et al. |
| 2013/0089591 A1 | 4/2013 | Vautrin et al. |
| 2013/0316937 A1 | 11/2013 | Denutte et al. |
| 2014/0162929 A1 | 6/2014 | Labeque et al. |
| 2014/0201927 A1 | 7/2014 | Bianchetti et al. |
| 2014/0322283 A1 | 10/2014 | Berthier et al. |
| 2016/0243008 A1* | 8/2016 | Berthier .......... A61Q 13/00 |
| 2017/0022459 A1 | 1/2017 | Denutte et al. |

FOREIGN PATENT DOCUMENTS

| | | |
|---|---|---|
| EP | 2 111 214 B1 | 10/2009 |
| EP | 2 545 988 A2 | 1/2013 |
| EP | 2 757 146 A1 | 7/2014 |
| WO | WO 2008/066654 A1 | 6/2006 |
| WO | WO 2008/098387 A1 | 8/2008 |
| WO | WO 2009/100553 A1 | 8/2009 |
| WO | WO 2011/075551 A1 | 6/2011 |
| WO | WO 2013/068255 A1 | 5/2013 |
| WO | WO-2015-140749 A1 | 9/2015 |
| WO | WO-2015/140764 A1 | 9/2015 |

* cited by examiner

MICROCAPSULES

CROSS REFERENCE TO RELATED APPLICATIONS

This application is a national stage application of International Application No. PCT/EP2016/065538, filed 1 Jul. 2016, which claims priority from Great Britain Patent Application No. 1511605.6, filed 2 Jul. 2015, which applications are incorporated herein by reference.

FIELD OF THE INVENTION

This invention is concerned with an encapsulated perfume composition comprising at least one aminoplast core-shell microcapsule dispersed in a suspending medium, and to consumer products containing said compositions.

BACKGROUND OF THE INVENTION

It is known to incorporate encapsulated perfume compositions in consumer products, such as household care, personal care, and fabric care products. Perfume compositions are encapsulated for a variety of reasons. Microcapsules can isolate and protect perfume ingredients from external suspending media, such as consumer product bases, in which they may be incompatible or unstable. They are also used to assist in the deposition of perfume ingredients onto substrates, such as skin, hair, fabrics or hard household surfaces. They can also act as a means of controlling the spatio-temporal release of perfume.

Aminoplast resin is a common encapsulating medium for perfume compositions. Core-shell microcapsules formed from aminoplast resin are generally quite resistant to leakage when dispersed in aqueous suspending media, even in some surfactant-containing media. Furthermore, when incorporated into consumer products, such as laundry detergents or conditioners, they provide perfumery benefits that are unattainable if perfume is incorporated directly into those products.

Fast moving consumer goods companies have come to rely on encapsulated perfume compositions to add perfumery benefits to their products, and they expect that encapsulated perfumes should not leak excessively during storage, and should provide long-lasting perfume performance when deposited on substrates. However, in addition to these requirements, in order for an encapsulated perfume composition to be perceived favourably by customers, it must be possible for customers to easily carry out all operations related to their use, for example they should be easy for a customer to handle, store, transport, and the like. More particularly, they should be compatible with suspending media, including consumer product bases into which they are to be incorporated.

European patent application EP 2111214 discloses a particular type of aminoplast core-shell microcapsule, in which perfume is encapsulated in shells formed of a melamine-formaldehyde resin cross-linked with resorcinol. These encapsulated compositions are characteristically stable and impart desirable perfumery benefits on consumer products. However, applicant found that the use of resorcinol in the preparation of a slurry of aminoplast microcapsules can lead to an undesirable discoloration of the slurry.

There remains a need, therefore, to provide melamine-formaldehyde microcapsules, which are at least comparable in terms of stability and performance as the prior art resorcinol microcapsules referred to hereinabove, but which are not prone to discoloration.

Applicant surprisingly found that in the preparation of aminoplast microcapsules, replacing resorcinol with a diamine cross-linker, it was possible to form aminoplast microcapsules that were at least comparably stable and performant as prior art aminoplast microcapsules, and furthermore, do not exhibit the discoloration issue.

SUMMARY OF THE INVENTION

The invention provides in a first aspect an encapsulated perfume composition comprising at least one aminoplast core-shell microcapsule dispersed in a suspending medium, the microcapsule comprising a perfume-containing core encapsulated in a shell comprising a cross-linked network of an aminoplast resin, wherein the cross-linker is a diamine.

In another aspect, the invention provides a method of preparing an encapsulated perfume composition as hereinabove described, said method comprising the steps of dispersing perfume-containing droplets in an aqueous suspending medium, and encapsulating the droplets in a polymeric shell comprising a network of cross-linked aminoplast resin.

In another aspect, the invention provides the use of a diamine as a cross-linker in a method of forming an encapsulated perfume composition as hereinabove described.

In yet another aspect, the invention provides a consumer product comprising an encapsulated perfume composition as hereinabove described.

In still another aspect of the invention, in the preparation of an encapsulated perfume composition as defined herein, the use of a diamine to reduce, eliminate or prevent discolouration of said composition is provided.

DETAILED DESCRIPTION OF THE INVENTION

The present invention is concerned with encapsulated perfume compositions comprising a novel aminoplast core-shell microcapsule, which is characterized by an aminoplast shell that is formed when an amino-aldehyde pre-condensate, for example a melamine-formaldehyde pre-condensate is caused to undergo a poly-condensation reaction and cross-link with a diamine cross-linker during the encapsulation process.

It is known to co-react melamine, urea and formaldehyde to form melamine-urea-formaldehyde (MUF) resins, although this is not a practical means of producing encapsulated perfume compositions, and to the best knowledge of the applicant, such resins have not been employed to encapsulate complex, multi-component compositions such as perfume compositions.

Furthermore, in the field of microencapsulation, it is known to use urea or derivatives of urea, which are examples of diamines, as formaldehyde scavengers, which mop-up residual formaldehyde after the formation of aminoplast core-shell microcapsules (see for example EP 2545988 A2). In such cases, the diamine is not being employed as a cross-linker, but merely to reduce formaldehyde emissions.

So, whereas post-adding derivatives of urea to an already formed melamine-formaldehyde resin microcapsule is known, and whereas co-reacting urea with melamine and formaldehyde is known, the applicant is not aware of the use of urea, or diamines generally, as a cross-linker that is mixed with an amino-aldehyde pre-condensate, such as melamine-formaldehyde pre-condensate during the encapsulation process to form a cross-linked aminoplast resin.

The novel use of a diamine as a cross-linker led to the surprising advantage that the aminoplast microcapsules formed were colourless, but retained stability and performance characteristics that were comparable with microcapsules made using resorcinol as the sole cross-linking agent. The use of a diamine in this way provides an aminoplast shell that has a novel structure and has advantages over prior art aminoplast capsules.

Accordingly, in a particular embodiment of the present invention there is provided an encapsulated perfume composition comprising at least one aminoplast core-shell microcapsule dispersed in a suspending medium, the microcapsule comprising a perfume-containing core encapsulated in a shell, said shell comprising a network of cross-linked aminoplast resin, wherein 75-100% by weight (wt %) of the cross-linked resin is formed of 50-90 wt %, preferably from 60-85 wt %, of a terpolymer, and 10-50 wt %, preferably from 10-25 wt % of a polymeric stabilizer; and wherein said terpolymer comprises:

(a) from 20-35 wt %, preferably 22-30 wt % of moieties derived from at least one triamine,
(b) from 30-60 wt %, preferably 40-55 wt % of moieties derived from at least one diamine, and
(c) from 20-35 wt %, preferably 22-30 wt % of moieties derived from the group consisting of alkylene and alkylenoxy moieties having 1 to 6 methylene units, preferably 1 to 4 methylene units and most preferably 1 methylene unit.

The cross-linked aminoplast resin is formed when an amino-aldehyde pre-condensate is caused to undergo a poly-condensation reaction to form the resin, and the diamine cross-links with the poly-condensed material to form the network of cross-linked resin.

In a particular embodiment of the invention the cross-linked resin is formed when a mixture comprising amino-aldehyde pre-condensate and a diamine are present in a weight ratio of 40:60 to 65:35, and more particularly 45:55 to 55:45 undergoes a poly-condensation reaction.

The encapsulated perfume compositions according to the invention can be employed as an alternative to resorcinol-based microcapsules described in EP 2111214 to avoid discolouration issues. The encapsulated perfume compositions of the present invention, therefore, are preferably resorcinol-free. Although the use of small amounts of resorcinol, or other aromatic polyols as more fully described below, as a cross-linker is not excluded in the practice of the present invention, the levels used should not be so high as to create discolouration issues.

Examples of suitable aromatic polyols include, but are not limited to phenol, 3,5-dihydroxy toluene, bisphenol A, hydroquinone, xylenol, polyhydroxy naphthalene and polyphenols produced by the degradation of cellulose and humic acids.

The skilled person will be able to determine the threshold usage level of resorcinol or other aromatic polyols using only routine experimentation. However, levels below 6 wt %, more particularly less than 2 wt % based on the weight of the shell are generally acceptable, although the usage levels may vary in response to the pH of the encapsulated perfume composition, or the medium in which it is incorporated. The applicant found in particular that the tolerated levels of aromatic polyols, and particularly resorcinol reduces in response to increased pH, and may in some cases of high pH media drop to less than 1 wt % or even less than 0.25 wt %, based on the weight of the shell.

The encapsulated perfume compositions of the present invention are colourless upon visual inspection. The characteristic absence of colour of the encapsulated perfume composition can be determined objectively using the CIELAB scale developed by the Commission Internationale de l'Eclairage (CIE). The measurement technique is well known in the art, and is more fully described in the examples, herein below. The parameter ΔE is a measure of the distance between colours on the CIELAB scale. For the purpose of the present invention, an encapsulated perfume composition that exhibits a ΔE value of 3 or less, is deemed colourless, and will be perceived by the human eye as white.

Accordingly, in an embodiment of the present invention there is provided an encapsulated perfume composition as defined herein, having a ΔE value on the CIELAB scale of 3 or less.

In an embodiment of the invention, in the preparation of an encapsulated perfume composition defined herein, there is provided the use of a diamine to reduce, eliminate or prevent discolouration, such that composition has a ΔE value on the CIELAB scale of 3 or less.

Amino-aldehyde pre-condensates useful in the preparation of aminoplast resins are well known in the art. Suitable amino-aldehyde pre-condensates include but are not limited to partially methylated mono- and poly-methylol-1,3,5-triamino-2,4,6-triazine pre-condensates, such as those commercially available under the Trade Mark CYMEL (ex Cytec Technology Corp.) or LURACOLL (ex BASF), and/or mono- and polyalkylol-benzoguanamine pre-condensates, and/or mono- and polyalkylol-glycouril pre-condensates. These alkylolated polyamines may be provided in partially alkylated forms, obtained by addition of short chain alcohols having typically 1 to 6 methylene units. These partially alkylated forms are known to be less reactive and therefore more stable during storage. Preferred polyalkylol-polyamines are polymethylol-melamines and polymethylol-1-(3,5-dihydroxy-methylbenzyl)-3,5-triamino-2,4,6-triazine.

A particularly preferred amino-aldehyde pre-condensate is a pre-condensate of melamine-formaldehyde, which can be formed of methylolated melamine formed by the reaction of melamine and formaldehyde, in a manner known per se. Methylolated melamine may also be partially methoxymethylated by the action of methanol on the methylolated melamine.

Diamine cross-linkers useful in the present invention include, but are not limited to poly[N-(2,2-dimethoxy-1-hydroxy)] polyamines, including di-[N-(2,2-dimethoxy-1-hydroxy)] urea, tri-[N-(2,2-dimethoxy-1-hydroxy)] melamin, tetra-[N-(2,2-dimethoxy-1-hydroxy)] glycouryl and di-[N-(2,2-dimethoxy-1-hydroxy)] benzoguanidin.

A particularly suitable diamine is urea.

The cross-linker is an important component of a core-shell microcapsule. It plays an important function in determining the quality of the shell, and therefore the stability and performance of microcapsules. It might be expected that modifying the cross-linker, to replace a polyol such as the exemplary resorcinol, with a diamine such as urea, might affect microcapsule stability and performance. Nevertheless, the applicant surprisingly found that stable and performant microcapsules could be formed, and particularly stable and performant microcapsules could be obtained by selecting the weight ratio of diamine, e.g. urea, to amino-aldehyde pre-condensate, such as melamine formaldehyde pre-condensate. Hence, in a particular embodiment the of the invention, the ratio of amino-aldehyde pre-condensate to diamine is about 0.5 to 1.5, and more particularly about 0.8 to 1.2.

During the preparation of encapsulated perfume compositions it is conventional to employ a polymeric stabilizer. Polymeric stabilizers act as colloid stabilizers and are employed to stabilize the oil-water interface during microcapsule formation. The polymeric stabilizer functions in several ways: It ensures that stable oil-in-water emulsions are formed allowing migration of shell-forming materials, e.g. pre-condensate and cross-linker to the oil-water interface; and it functions essentially as a template around which poly-condensation and cross-linking reactions can take place to form the encapsulating cross-linked aminoplast resin shells. Colloid stabilizers also prevent the formed microcapsules from agglomerating.

Some of the polymeric stabilizer will be washed out of the microcapsules as they form, but some will be retained within the encapsulating shells and become part of the shells.

Particular examples of suitable polymeric stabilizers include acrylic copolymers bearing sulfonate groups, such as those available commercially under the trade mark LUPASOL (ex BASF), such as LUPASOL PA 140 or LUPASOL VFR; copolymers of acrylamide and acrylic acid, copolymers of alkyl acrylates and N-vinylpyrrolidone, such as those available under the trade mark Luviskol (e.g. LUVISKOL K 15, K 30 or K 90 ex BASF); sodium polycarboxylates (ex Polyscience Inc.) or sodium poly(styrene sulfonate) (ex Polyscience Inc.); vinyl and methyl vinyl ether-maleic anhydride copolymers (e.g. AGRIMER™ VEMA™ AN, ex ISP), and ethylene, isobutylene or styrene-maleic anhydride copolymers (e.g. ZEMAC™). Hence the preferred polymer stabilizers are anionic polyelectrolytes.

The invention can be further understood with reference to a method of preparing the encapsulated perfume composition, which method forms another aspect of the present invention.

Generally, encapsulated perfume compositions may be prepared by first forming an oil-in-water emulsion consisting of perfume-containing oil droplets dispersed in an aqueous continuous phase. Thereafter, amino-aldehydepre-condensate is caused to undergo a poly-condensation reaction to form an encapsulating aminoplast resin shell around the perfume-containing droplets, which resin is cross-linked with a diamine.

In a particular embodiment of the present invention there is provided a method of preparing an encapsulated perfume composition as herein described comprising the steps of:
  mixing and dissolving a polymeric stabilizer (e.g., poly(maleic anhydride-co-vinyl methyl ether) in water under moderate shear;
  adjusting the temperature to about 30° C., and more particularly 35±2° C. and the pH to 4.6±2 before adding the amino-aldehyde pre-condensate, diamine cross-linker and perfume;
  emulsifying the mixture, whereby the stirring speed and the geometry of the mixer is selected to obtain a desired average droplet size range and droplet size distribution;
  raising the temperature to an elevated temperature above about 80° C., more particularly above about 85° C., (e.g. to 88° C.±1° C.) over a time period of about 1 hour, and more particularly 75 minutes and maintaining the reaction at this elevated temperature for a sufficient period of time (e.g. about 2 hours) to affect poly-condensation and cross-linking reactions, thereby to form microcapsules;
  adding a formaldehyde scavenger, which may be added over a period of about 10 minutes, while the mixture is still at the elevated temperature (e.g. 88° C.), before cooling the mixture to room temperature;
  optionally, adding a suspending agent, e.g. carbopol to the mixture under stirring to ensure that the microcapsules are stably suspended; and
  optionally adjusting pH, if necessary, to within the range of 6 to 6.6.

If it is desired to obtain microcapsules having a bi-layered shell, when reaching the aforementioned elevated temperature, the reaction temperature is maintained for a period suitable to form a shell (e.g. about 35 minutes), and thereafter the pH is reduced and further amino-aldehyde pre-condensate is added to form the second layer. In particular, the mixture is maintained at the elevated temperature for up to about 2 hours.

The applicant found that the kinetics of the poly-condensation of the amino-aldehyde pre-condensate was relatively fast compared with the cross-linking reaction. Therefore, in order to avoid coagulation of the microcapsules as they form, applicant found that it was advantageous to heat the system to the above-mentioned temperature in order to accelerate the cross-linking reaction. Accordingly, heating the reaction mixture at a constant rate over about 1 hour, and more particularly about 75 minutes to reach the aforementioned elevated temperature, and more particularly a temperature of 88° C.±1° C. is an important process feature. Furthermore, holding the reaction temperature substantially constant at this reaction temperature, that is 88 C.±5° C., in particular at 88 C.±2° C. for at least about 2 hours, and more particularly 2 hours and 15 minutes ±15 minutes, constitutes another important process feature of the invention.

Accordingly, in a particular embodiment of the present invention, there is provided a process of preparing an encapsulated perfume composition as herein described wherein the poly-condensation and cross-linking reactions to form the microcapsules are carried out under a linear and positive temperature gradient over about 1 hour, and more particularly about 75 minutes to reach the elevated temperature, and particularly 88° C.±1° C., and thereafter under a substantially constant temperature that is 88 C.±5° C., in particular at 88 C.±2° C. for at least about 2 hours, and more particularly 2 hours and 15 minutes ±15 minutes.

In an encapsulated perfume composition of the present invention, the microcapsule shells may be formed of a single layer, bi-layer or multi-layer, that is, three or more layers. The layers may be compositionally the same, that is, the amino-aldehyde pre-condensate and cross-linker employed may be the same, or they may be different.

Bi-layer or multi-layer shell microcapsules, by virtue of their thicker shells, exhibit improved leakage stability compared with the single-layer variants. Surprisingly, however, it was found that microcapsules characterized by having bi-layer or multi-layer shells, not only display good leakage stability, even in harshly extractive environments such as consumer product bases containing bleaches or concentrated surfactants, but in addition, when deposited onto a substrate such as fabric, skin, hair or hard household surfaces, they release perfume in a desirable manner as to provide a long-lasting odour benefit.

Microcapsule shell thickness is determined by the amount of shell-forming material employed in their preparation, and the skilled person has the latitude to form microcapsules having a wide range of shell thicknesses. Typically, however, a microcapsule with shell formed with a single layer possess a shell thickness of about 50-250 nm, whereas a microcapsule with a shell comprising two layers has a shell thickness of about 50-500 nm, more particularly more than 250 nm to 500 nm.

In a particular aspect of the invention, the provision of bi-layered or multi-layered capsules is advantageous, if a certain capsule shell thickness is desired. By applying the polymeric material layer-wise, the control about the capsule shell thickness is increased, and the formed shell does exhibit better stability.

In addition, the applicant found that it can become increasingly difficult to build shell thickness above 250 nm in a single step. Without intending to be bound by theory, it is believed that too much shell-forming material present during emulsification can destabilize the emulsion and affect capsule formation. Accordingly, if capsules with shells having a thickness of more than about 250 nm are required, the provision of multi-layered capsules might be preferred.

In a particular aspect of the invention, microcapsules may be coated with a deposition aid. A deposition aid facilitates the adhesion and retention of the microcapsules on a substrate upon which they are applied. Microcapsules may contain up to 25%, and more particularly up to 10% of the deposition aid, based on the total weight of the solid content of microcapsules in an encapsulated perfume composition.

Typically, deposition aids are cationic polymers. Aminoplast microcapsules, typically bear a net negative charge, and the cationic polymer allows partial or complete neutralization of the negative electrical charge borne by the microcapsules, or even converting them into positively-charged microcapsules.

Preferred cationic polymers include cationic cellulose derivatives, such as those available under the Trade Mark UCARE (ex Amerchol) and SOFTCAT SX 1300H (ex Dow Chemicals), polysaccharides, and quaternized gums, such as quaternized guar gums available under the Trade Mark JAGUAR (ex Rhodia), polyethylene imine, such as those available commercially under the Trade Mark LUPASOL (ex BASF), cationic polyacrylates and acrylamides, such as that commercially available under the Registered Mark SALCARE® SC60 (ex BASF), Polyquaternium 6, such as that commercially available under the Trade Mark MERQUAT 100 (ex Lubrizol), Polyquaternium 10, such as that commercially available under the Trade Mark UCARE JR 125 (ex Dow Chemicals), Polyquaternium 11, such as that commercially available under the Trade Mark GAFQUAT 755N (ex Ashland), Polyquaternium 55, such as that commercially available under the Trade Mark STYLEZE W 20 (ex Ashland), quaternized acrylic homopolymers and copolymers, such as that commercially available under the Trade Mark DEPOSILK Q1, (ex Air Products), copolymers of vinylpyrrolidone and quaternized vinylimidazole, such as that commercially available under the Trade Mark LUVIQUAT FC 550 (ex BASF), gelatine, quaternized protein hydrolysates, and quaternized amino silicones.

Other cationic compounds that can be used include the polyquaternium range, all of which have a plurality of quaternary ammonium groups, polymeric species such as diallyl dimethyl ammonium chloride/acrylamide polymers, for example, those available under the Trade Mark MERQUAT (ex Nalco) and copolymers of vinyl pyrrolidone and quaternized dimethyaminoalkyl methacrylate, for example, those available under the Trade Mark GAFQUAT HS 50 and HS 100 (ex ISP).

Encapsulated perfume compositions of the present invention are prepared in the form of aqueous slurry, having typically 20 to 50% solids content, and more typically 30 to 45% solid content, wherein the term "solids content" refers to the combined weight of the microcapsule core and shell material expressed as a percentage of the total weight of the slurry.

The volume average diameter D 50 of the microcapsules may range between 1 micrometer to 100 micrometers, or more, depending on the shear applied to the system during microcapsule formation. The selection of the most appropriate microcapsule size range and size distribution depends on the application envisioned.

In the case where the microcapsules are to be used in laundry products, it has been found that microcapsules having size ranging from 1 to 60 micrometers, preferably from 2 to 50 micrometers, more preferably from 5 to 30 micrometers offer optimal performance in terms of deposition and olfactive impact when rubbed with low to moderate shear stress.

In case of hair care application, it has been found that microcapsules having size ranging from 1 to 20 micrometers, preferably from 2 to 15 micrometers, more preferably from 4 to 10 micrometers offer optimal performance in terms of deposition and olfactive impact when combed.

The particle size distribution is measured using the technique of laser diffraction, using a Mastersizer 2000 supplied by Malvern. The technique is based on the principle that the light from a coherent source, in this case the laser beam, will scatter as particles pass through the beam, with the angle of the scattered light being directly related to the size of the particles. A decrease in particle size results in a logarithmic increase in the observed scattering angle. The observed scattering intensity is also dependent on particle size and diminishes relative to the particle's cross-sectional area. Large particles therefore scatter light at narrow angles with high intensity, whereas small particles scatter at wider angles but with low intensity. Detectors are used to measure the scattered light pattern produced over a wide range of angles and, hence, determine the particle size distribution of the sample using an appropriate optical model.

For the measurement of the particle size, the sample was placed in the Malvern Hydro2000 SM module, supplied with the Mastersizer 2000, for the measurement of wet dispersions. The supplied software was used to transform the measured scattered light pattern into the particle size distribution. The optical model parameters used were 1.47 and 0 for the refractive index and absorption index, respectively. Sample measurement was taken over a period of five seconds using 5000 measurement snaps.

The slurry may contain formulation aids, such as stabilizing and viscosity control hydrocolloids, biocides, and additional formaldehyde scavengers.

Typically, hydrocolloids are used to improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful for the sake of the present invention encompass: polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid)copolymer, poly(alkyleneoxide), poly(vinylmethylether), poly(vinylether-co-maleic anhydride), and the like, as well as poly-(ethyleneimine), poly((meth)acrylamide), poly (alkyleneoxide-co-dimethylsiloxane), poly(amino dimethylsiloxane), and the like, and their quartenized forms.

Preferably, Carbopol ETD 2561, a lightly crosslinked polyacrylic acid polymer, is used. Preferably, the suspending agent is added to the slurry in a sufficient quantity to obtain a final viscosity in the range of 100 mPa·s to 3500 mPa·s, more preferably from 250 mPa·s to 2500 mPa·s Typical formaldehyde scavengers comprise compounds capable of binding free formaldehyde in aqueous media, such as sodium sulfite, melamine, glycine, and carbohydrazine. However, when the microcapsules are aimed to be used in products having low pH, such as fabric care conditioners, formaldehyde scavengers are preferably selected from beta diketones, such as beta-ketoesters, or from 1,3-diols, such as propylene glycol. Preferred beta-ketoesters comprise alkyl-malonates, alkyl aceto acetates and polyvinyl alcohol aceto acetates.

The encapsulated perfume compositions of the present invention are further characterized in that microcapsules have a nominal shell to core mass ratio in the range from 0.1 to 25%, preferably from 1 to 20% and most preferably from 5 to 15%.

In the practice of the present invention it is possible to load the microcapsules with between 20 and 50 wt % of perfume ingredients, more particularly between 30 and 40 wt %, and still more particularly between 35 and 40 wt %, based on the total weight of the slurry.

A comprehensive list of perfume ingredients that may be encapsulated in accordance with the present invention may be found in the perfumery literature, for example "Perfume & Flavor Chemicals", S. Arctander (Allured Publishing, 1994), as well as later editions of this work, which are herein incorporated by reference.

However, the applicant has found that by employing perfume ingredient selection criteria set forth herein below, it is possible to influence both the permeability of the microcapsule shell and the rate of diffusion of the perfume ingredients through the shell.

More specifically, the applicant has found that a parameter of perfume ingredient selection, which is the electron density distribution within a perfume ingredient, as reflected by the temperature-independent integral of the molecular iso-surface having electron density equal to $$0.002 e/a_0^3$$

wherein
e is the dimension-less electron charge and
$a_0$ is the Bohr radius of the hydrogen atom ($a_0 = 5.2917720859 \times 10^{-11}$ m).

Employing Molecular Operating Environment chemical computational software (Version 2009, ex Chemical Computing Group, Canada, or later versions thereof, and optionally using the DDASSL RECON software plug-in (Rensselaer Polytechnic Institute, 2001-2003, or later versions thereof)), the value of this integral is given by the so-called RECON_VOLTAE quantum chemically derived descriptor. In particular, it was surprisingly found that the leakage of perfume ingredients through a microcapsule shell is considerably suppressed when the value of the molecular iso-surface integral of ingredients exceeds a certain value, more fully described herein below.

RECON VOLTAE is a parameter describing or expressing the topography of a molecule iso-surface that encloses a molecular space having an electron density is equal to $0.002 e/a_0^3$.

In the encapsulated perfume compositions described herein below, the concentration of any encapsulated perfume ingredients (wt %) is expressed relative to the total amount of perfume ingredients encapsulated and not to the total material encapsulated. For example, although it is preferred that only perfume ingredients are encapsulated, it is contemplated that in addition to perfume ingredients, other non-perfumery ingredients or excipients may be encapsulated such as solvents or diluents, which may be beneficial in reducing the amount of perfume composition that might leak from the cores. For example, certain perfume ingredients may be provided as solutions or are diluted in suitable solvents, such as triethyl citrate "TEC". In such cases, only the amount of perfume ingredient is counted in the wt % calculation and not the solvent or diluent used to dissolve or dilute the perfume ingredient.

Such solvents or diluents are hydrophobic materials that are miscible in the perfume ingredients, and which have little or no odour in the quantities employed. Solvents commonly employed have high C log P values, for example greater than 6 and even greater than 10. Solvents include triglyceride oil, mono and diglycerides, mineral oil, silicone oil, diethyl phthalate, poly (alpha-olefins), castor oil and isopropyl myristate.

The cores of core-shell microcapsules may also contain commonly employed adjuvants. The term "adjuvants" refers to ingredients that may affect the performance of a composition, other than its hedonic performance. For example, an adjuvant may be an ingredient that acts as an aid to processing a perfume composition or consumer product containing said composition, or it may improve handling or storage of a perfume composition or consumer product. It might also be an ingredient that provides additional benefits such as imparting colour or texture. It might also be an ingredient that imparts light resistance or chemical stability to one or more ingredients contained in a perfume composition or consumer product. A detailed description of the nature and type of adjuvants commonly used in perfume compositions or consumer products cannot be exhaustive, but such ingredients are well known to a person skilled in the art. Examples of adjuvants include surfactants and emulsifiers; viscosity and rheology modifiers; thickening and gelling agents; preservative materials; pigments, dyestuffs and colouring matters; extenders, fillers and reinforcing agents; stabilizers against the detrimental effects of heat and light, bulking agents, acidulants, buffering agents and antioxidants. A more detailed discussion of such solvents, diluents or adjuvants may be found in perfumery monographs such as the Arctander reference mentioned hereinabove.

Furthermore, in encapsulated perfume compositions it is preferred if they are comprised of at least 3 perfume ingredients, more particularly at least 5, still more particularly at least 7 and more particularly still at least 9 perfume ingredients having known RECON_VOLTAE values larger than the threshold values referred to below.

It is preferred if in the practice of the present invention, perfume compositions to be encapsulated contain perfume ingredients having known RECON_VOLTAE values larger than about 1200 Bohr$^3$, more particularly larger than about 1540 Bohr$^3$, and still more particularly larger than about 1750 Bohr$^3$.

As used herein, the term "known" as it is used in relation to the RECON_VOLTAE values, or any of the other physico-chemical parameters related to the perfume ingredients described herein, means the values are known to a formulator of a perfume composition, or can be calculated in accordance with the teaching provided herein.

Preferably, more than 70 wt %, in particular more than 80 wt %, and more particularly more than 90 wt % of the perfume ingredients encapsulated have known RECON_VOLTAE values larger than about 1200 Bohr$^3$.

More particularly, more than 30 wt %, more than 35 wt %, more than 40 wt % of the perfume ingredients encapsulated have known RECON_VOLTAE values larger than about 1540 Bohr$^3$.

Encapsulated perfume compositions containing such a distribution of encapsulated perfume ingredients are particularly suitable for incorporation into aggressive (or extractive) media. These media include fabric softening or conditioning products, and particularly those containing quaternized ester surfactants (so-called "esterquats") and non-ionic surfactants. They are also usefully employed in powdered or granulated detergents, and liquid detergent compositions, and particular those formats designed as unit dosage forms contained in pouches or pods, and often referred to in the art as "liquid tabs". A fuller discussion of these ingredients and formulations is provided herein below.

They are particularly suitable for use in fabric softening or conditioning products containing unstructured surfactants. The term "unstructured surfactants" is known to persons skilled in the art. It refers to surfactant-containing compositions in which the surfactants tend to be present in the form of micelles. Micellar surfactants are particularly efficient in extracting encapsulated perfume ingredients from microcapsules.

Unstructured surfactants are to be contrasted with "structured surfactants". Structured surfactants compositions contain water, surfactant, and optionally other dissolved matter, which together form a mesophase, or a dispersion of a mesophase in a continuous aqueous medium. Surfactants and water interact to form phases that are neither liquids nor crystals; these are usually termed "liquid crystal phases," or alternatively "mesomorphic phases" or "mesophases." Because surfactants are highly organised in such compositions, they tend not to be particularly extractive towards encapsulated perfume ingredients.

Unstructured surfactants can usually be distinguished over structure surfactants upon visual inspection because the former tend to be transparent, or substantially so, whereas the latter, because of their structure, tend to appear as opaque, turbid or pearlescent.

Encapsulated perfume compositions in which more than 70 wt %, more than 80 wt %, more than 90 wt % of the perfume ingredients encapsulated have known RECON_VOLTAE values larger than about 1750 Bohr$^3$ form further embodiments of the present invention. Encapsulated perfume compositions containing such a distribution of encapsulated perfume ingredients are particularly suitable for incorporation into very aggressive media, such as those found in shampoos, hair conditioners and other personal cleansing compositions that may contain high levels of anionic, non-ionic and/or zwitterionic surfactants. A fuller discussion of these ingredients and formulations containing them is provided herein below.

By formulating perfume compositions in accordance with the known RECON_VOLTAE values set out herein, it is possible to form encapsulated perfume compositions that are less prone to leakage or extraction into surrounding suspending media, and particularly those highly extractive media referred to herein.

Without wishing to be bound by theory, it is believed that the electron density distribution of a perfume ingredient, as reflected by its RECON_VOLTAE value, influences the way the ingredient diffuses through the shell. In particular, the diffusion of ingredients having RECON_VOLTAE values above the threshold values recited hereinabove, e.g. above about 1200, is delayed, or even suppressed, relative to perfume ingredients having RECON_VOLTAE values below the given threshold value. It follows from the above that in order to provide encapsulated perfume compositions having desirable long-term stability in consumer products, particularly those that are considered aggressive or extractive media, such as those found in personal cleansing compositions and laundry detergent bases, while still delivering perfume at a desired release rate once deposited on a substrate, and particularly a dry substrate, the encapsulated perfume composition should contain a certain amount of perfume ingredients having known RECON_VOLTAE values below the aforementioned 1200 Bohr$^3$ threshold. These sub-threshold perfume ingredients will diffuse more readily from core-shell microcapsules.

Being in possession of the knowledge of the RECON_VOLTAE parameter, and the relationship of RECON_VOLTAE to both performance and stability of encapsulated perfume compositions, the skilled person is able to create a variety of perfumes for encapsulation by balancing the relative amounts of both sub- and super-threshold perfume ingredients, designed to be both stable and performant when used in more or less extractive consumer product bases.

Thus, an encapsulated perfume composition as defined hereinabove, additionally comprising encapsulated perfume ingredients having RECON_VOLTAE values below 1200 Bohr$^3$, forms another embodiment of the present invention.

In a particular embodiment an encapsulated perfume composition is characterized by a distribution of perfume ingredients having known RECON_VOLTAE values, wherein 70 wt % or more, 80 wt % or more, 90 wt % or more of the perfume ingredients have known RECON_VOLTAE values larger than 1200 Bohr$^3$ and 0.1 to 30 wt %, more particularly from 1 to 20 wt % and more particularly still from 1 to 10 wt % of perfume ingredients having known RECON_VOLTAE values below 1200 Bohr$^3$.

In another particular embodiment an encapsulated perfume composition is characterized by a distribution of perfume ingredients having known RECON_VOLTAE values, wherein: 30 wt % or more, 35 wt % or more, 40 wt % or more of perfume ingredients have known RECON_VOLTAE values larger than 1540 Bohr$^3$; and 30 wt % or more, 40 wt % or more, 50 wt % or more of the perfume ingredients have known RECON_VOLTAE values from 1200 Bohr$^3$ to 1540 Bohr$^3$; and from 0.1 to 30 wt %, from 1 to 20 wt %, from 1 to 10 wt % of the perfume ingredients have known RECON_VOLTAE values below 1200 Bohr$^3$.

In another particular embodiment an encapsulated perfume composition is characterized by a distribution of perfume ingredients having known RECON_VOLTAE values, wherein: from 0.5 to 30 wt %, from 1 to 25 wt %, from 5 to 20 wt % of the perfume ingredients have known RECON_VOLTAE values above 1750 Bohr$^3$; and 20 to 60 wt %, 25 to 55 wt %, 30 to 50 wt % of the perfume ingredients having known RECON_VOLTAE values from 1540 Bohr$^3$ to 1750 Bohr$^3$; and 5 to 50 wt %, more particularly 10 to 40 wt %, 15 to 30 wt % of the perfume ingredients have known RECON_VOLTAE values from 1200 Bohr$^3$ to 1540 Bohr$^3$; and from 0.1 to 30 wt %, from 1 to 20 wt %, from 1 to 10 wt % of perfume ingredients have known RECON_VOLTAE values below 1200 Bohr$^3$.

In yet another particular embodiment the encapsulated perfume composition is characterized by a distribution of perfume ingredients having known RECON_VOLTAE values, wherein 70 wt % or more, 80 wt % or more, 90 wt % or more of perfume ingredients have known RECON_VOLTAE values larger than 1750 Bohr$^3$; and from 0.1 to 30 wt %, from 1 to 20 wt %, from 1 to 10 wt % of the perfume ingredients have known RECON_VOLTAE values below 1750 Bohr$^3$.

In encapsulated perfume compositions described herein, it is preferred if the weight average of known RECON_VOLTAE values of the encapsulated perfume ingredients should be larger than 1540 Bohr$^3$ and more particularly larger than 1750 Bohr$^3$.

The weight average of known RECON_VOLTAE values is defined here as the weighed algebraic mean of the ingredient known RECON_VOLTAE values divided by the number of ingredients:

$$<\text{RECON\_VOLTAE}>_{perfume} \equiv 1/n \sum_n (\%_i)(\text{RECON\_VOLTAE}_i)$$

wherein n is the number of ingredients i, $\%_i$ the weight percentage of ingredient i and RECON_VOLTAE$_i$, the RECON_VOLTAE value of ingredient i.

Particularly stable and performant encapsulated perfume compositions can be prepared, when the selection of perfume ingredients is made on the basis of both the RECON_VOLTAE parameter as described hereinabove, and according to a perfume ingredient's equilibrium headspace-capsule partition coefficient "Kcaps".

The equilibrium headspace-capsule partition coefficient is defined as the headspace concentration (HS$_i^c$) of a perfume ingredient i in equilibrium with a microcapsule containing an encapsulated perfume composition P comprising perfume ingredient i at a given concentration divided by the headspace concentration (HS$_i^P$) in equilibrium with free perfume P comprising same concentration of ingredient i.

$$Kcaps_i = \frac{HS_i^c}{HS_i^P}$$

The headspace concentration in equilibrium with a microcapsule can be measured using techniques well known to a person skilled in the art. In a typical procedure, a known concentration of microcapsules is transferred to a vial VC, which is closed with a septum and allowed to equilibrate at 25° C., and a known amount of free perfume is transferred to a vial VP containing a strip of blotter paper on which the perfume is deposited with a syringe. The vial is closed with a septum and allowed to equilibrate at 25° C. Headspace aliquots are then taken from both vials and the headspace concentration profiles are determined quantitatively using methods known in the art, such as headspace capillary gas chromatography, headspace gas chromatography ion mobility spectrometry, gas spectroscopy and the like.

Kcaps may be determined experimentally, or it can be calculated for an ingredient using techniques known in the art. In particular, the effect of perfume ingredients on microcapsule stability can be predicted from QSAR analysis using MOE software.

As the person skilled in the art will appreciate, QSAR methods, in the context of the present invention, assume that performance of a perfume ingredient is correlated with its chemical structure and that as a consequence activity can be modeled as a function of calculable physiochemical attributes. Such a model for performance prediction can then be used to screen the palette of known perfume ingredients, or indeed libraries of other molecules for useful candidate ingredients.

Using QSAR analysis of a representative sample of perfume ingredients in the present invention resulted in the identification of a physicochemical parameter ($\log_{10}$ Kcaps) contributing to the effect of perfume ingredients on the stability of microcapules.

$\log_{10}$Kcaps was calculated by constructing a Quantitative Structure Activity Relationship, by performing a linear regression of molecular descriptors available within computational chemistry perfume MOE (Molecular Operation Environment, version 2013.08.01, purchased from Chemical Computing Group, Corporate Headquarters, 1010 Sherbrooke St. W, Suite 910, Montreal, Canada H3A 2R7, optionally using the DDASSL RECON software plug-in (Rensselaer Polytechnic Institute, 2001-2003, or later versions thereof)). QSAR analysis was carried out using a total of 75 perfume ingredients selected for the analysis on the basis of them being a representative set of perfume ingredients that had been used in encapsulated perfume compositions.

The resulting QSAR equation is given below:

$\log_{10}$Kcaps=−0.613884945931533+ 0.367145678964078 Average_EO_Neg+ 0.154423533060832 E_sol+1.72305610065098 MACCS(136)+0.0650007063247245 PEO-E_VSA+3−1.6045990231291 PEOE_VSA_F-POS+12.0572868318683 RA_ 2D_pEP10− 1082.58386145862 RA_nEP2− 0.0382420195399682 RECON_Del(K)NA3+ 53.5822360317755 RECON_FEP9− 2.50813850930136 RECON_FPIP8+ 5.73871249195905RECON_SIKA10+ 0.0400054462330909 kS_tsC.

The definition the molecular descriptors used in above equation can be found in MOE manual version 2013.08.01 (edited by Molecular Operation Environment, Chemical Computing Group, Corporate Headquarters, 1010 Sherbrooke St. W, Suite 910, Montreal, Canada H3A 2R7), which is hereby incorporated by reference.

Calculated $\log_{10}$ Kcaps values of some perfume ingredients are provided in the Tables below.

Perfume ingredients that are particularly useful in encapsulated perfume compositions according to the present invention may be grouped according to their respective RECON_VOLTAE values and their calculated $\log_{10}$ Kcaps values.

Thus, GROUP 1 perfume ingredients have RECON_VOLTAE values larger than 1200 Bohr$^3$ and calculated $\log_{10}$Kcaps which are greater than −3, where the term $\log_{10}$ refers to the decimal logarithm. Perfume ingredients of GROUP 1 include but are not limited to:

| Perfumery ingredient | RECON_VOLTAE (Bohr$^3$) | LogKcaps |
|---|---|---|
| HEDIONE (methyl 3-oxo-2-pentylcyclopentaneacetate) | 1784 | −2.4 |
| ALLYL CYCLOHEXYL PROPIONATE (allyl 3-cyclohexylpropanoate) | 1606 | −2.0 |

-continued

| Perfumery ingredient | RECON_VOLTAE (Bohr$^3$) | LogKcaps |
|---|---|---|
| AGRUMEX (2-(tert-butyl)cyclohexyl acetate) | 1678 | −1.9 |
| DIMETHYL BENZYL CARBINYL ACETATE (2-methyl-1-phenylpropan-2-yl acetate) | 1506 | −2.4 |
| IRISONE ALPHA ((E)-4-(2,6,6-trimethylcyclohex-2-en-1-yl)but-3-en-2-one) | 1676 | −1.8 |
| ISO E SUPER (1-(2,3,8,8-tetramethyl-1,2,3,4,5,6,7,8-octahydronaphthalen-2-yl)ethanone) | 2024 | −1.4 |
| ISORALDEINE 70 ((E)-3-methyl-4-(2,6,6-trimethylcyclohex-2-en-1-yl)but-3-en-2-one) | 1806 | −2.0 |
| NECTARYL (2-(2-(4-methylcyclohex-3-en-1-yl)propyl)cyclopentanone) | 1822 | −1.9 |
| BOISAMBRENE FORTE ((ethoxymethoxy)cyclododecane) | 2063 | −2.0 |
| BOISIRIS ((1S,2R,5R)-2-ethoxy-2,6,6-trimethyl-9-methylenebicyclo[3.3.1]nonane) | 1914 | −1.0 |
| JASMACYCLENE ((3aR,6S,7aS)-3a,4,5,6,7,7a-hexahydro-1H-4,7-methanoinden-6-yl acetate) | 1418 | −1.7 |
| FLOROCYCLENE ((3aR,6S,7aS)-3a,4,5,6,7,7a-hexahydro-1H-4,7-methanoinden-6-yl propionate) | 1549 | −1.6 |
| HEXYL SALICYLATE (hexyl 2-hydroxybenzoate) | 1685 | −1.6 |
| DIPENTENE (1-methyl-4-(prop-1-en-2-yl)cyclohex-1-ene) | 1203 | −0.1 |
| TETRAHYDRO LINALOOL (3,7-dimethyloctan-3-ol) | 1449 | −2.2 |
| AMYL SALICYLATE (pentyl 2-hydroxybenzoate) | 1556 | −1.4 |
| ALDEHYDE C 12 MNA PURE (2-methylundecanal) | 1661 | −2.3 |
| BUTYL CYCLOHEXYL ACETATE PARA (4-(tert-butyl)cyclohexyl acetate) | 1682 | −2.7 |
| DAMASCONE DELTA ((E)-1-(2,6,6-trimethylcyclohex-3-en-1-yl)but-2-en-1-one) | 1654 | −1.3 |
| DIMETHYL BENZYL CARBINYL BUTYRATE (2-methyl-1-phenylpropan-2-yl butyrate) | 1767 | −1.6 |
| EUCALYPTOL ((1s,4s)-1,3,3-trimethyl-2-oxabicyclo[2.2.2]octane) | 1278 | −1.0 |
| FRUTONILE (2-methyldecanenitrile) | 1597 | −1.9 |
| HEXYL CINNAMIC ALDEHYDE ((E)-2-benzylideneoctanal) | 1778 | −2.5 |
| IONONE BETA ((E)-4-(2,6,6-trimethylcyclohex-1-en-1-yl)but-3-en-2-one) | 1670 | −1.6 |
| TERPINYL ACETATE (2-(4-methylcyclohex-3-en-1-yl)propan-2-yl acetate) | 1590 | −2.0 |
| UNDECAVERTOL ((E)-4-methyldec-3-en-5-ol) | 1531 | −2.1 |
| LINALOOL (3,7-dimethylocta-1,6-dien-3-ol) | 1367 | −2.3 |
| GARDOCYCLENE ((3aR,6S,7aS)-3a,4,5,6,7,7a-hexahydro-1H-4,7-methanoinden-6-yl isobutyrate) | 1677 | −1.5 |
| IRISONE ((E)-4-(2,6,6-trimethylcyclohex-2-en-1-yl)but-3-en-2-one) | 1676 | −1.8 |
| LILIAL (3-(4-(tert-butyl)phenyl)-2-methylpropanal) | 1738 | −2.0 |
| LINALYL ACETATE (3,7-dimethylocta-1,6-dien-3-yl acetate) | 1653 | −1.5 |
| GERANIOL ((E)-3,7-dimethylocta-2,6-dien-1-ol) | 1357 | −2.0 |
| ALLYL OENANTHATE (allyl heptanoate) | 1436 | −2.5 |
| PETALIA (2-cyclohexylidene-2-(o-tolyl)acetonitrile) | 1753 | −1.4 |
| NEOBERGAMATE FORTE (2-methyl-6-methyleneoct-7-en-2-yl acetate) | 1650 | −1.4 |
| ISONONYL ACETATE (3,5,5-trimethylhexyl acetate) | 1632 | −1.0 |
| FRESKOMENTHE (2-(sec-butyl)cyclohexanone) | 1313 | −1.6 |
| ORIVONE (4-(tert-pentyl)cyclohexanone) | 1474 | −2.1 |
| NONADYL (6,8-dimethylnonan-2-ol) | 1579 | −1.8 |
| METHYL PAMPLEMOUSSE (6,6-dimethoxy-2,5,5-trimethylhex-2-ene) | 1632 | −1.9 |
| ETHYL CAPRYLATE (ethyl octanoate) | 1462 | −1.5 |

-continued

| Perfumery ingredient | RECON_VOLTAE (Bohr$^3$) | LogKcaps |
|---|---|---|
| AMBER CORE (1-((2-(tert-butyl)cyclohexyl)oxy)butan-2-ol) | 1972 | −2.3 |
| CASHMERAN (1,1,2,3,3-pentamethyl-2,3,6,7-tetrahydro-1H-inden-4(5H)-one) | 1772 | −1.9 |
| CITRONELLOL (3,7-dimethyloct-6-en-1-ol) | 1392 | −2.4 |
| DAMASCENONE ((E)-1-(2,6,6-trimethylcyclohexa-1,3-dien-1-yl)but-2-en-1-one) | 1608 | −1.5 |
| ETHYL SAFRANATE (ethyl 2,6,6-trimethylcyclohexa-1,3-diene-1-carboxylate) | 1579 | −2.0 |
| EUCALYPTOL ((1s,4s)-1,3,3-trimethyl-2-oxabicyclo[2.2.2]octane) | 1278 | −1.0 |
| PEONILE (2-cyclohexylidene-2-phenylacetonitrile) | 1633 | −0.9 |
| DELPHONE (2-pentylcyclopentanone) | 1313 | −1.9 |
| SILVIAL (3-(4-isobutylphenyl)-2-methylpropanal) | 1700 | −2.5 |
| TETRAHYDRO MYRCENOL (2,6-dimethyloctan-2-ol) | 1449 | −2.1 |
| CITRONELLYL PROPIONATE (3,7-dimethyloct-6-en-1-yl propionate) | 1808 | −2.0 |
| CYCLOHEXYL SALICYLATE (cyclohexyl 2-hydroxybenzoate) | 1610 | −2.2 |
| ETHYL CAPROATE (ethyl hexanoate) | 1203 | −1.4 |
| CORANOL (4-cyclohexyl-2-methylbutan-2-ol) | 1486 | −2.7 |
| BORNYL ACETATE ((2S,4S)-1,7,7-trimethylbicyclo[2.2.1]heptan-2-yl acetate) | 1631 | −1.8 |
| ALDEHYDE C 10 DECYLIC (decanal) | 1403 | −2.9 |
| ALDEHYDE C 110 UNDECYLIC (undecanal) | 1533 | −2.8 |
| ALDEHYDE MANDARINE 10%/TEC ((E)-dodec-2-enal) | 1615 | −2.7 |
| AMBERMAX (1,3,4,5,6,7-hexahydro-.beta.,1,1,5,5-pentamethyl-2H-2,4a-Methanonaphthalene-8-ethanol) | 2275 | −2.8 |
| BELAMBRE ((1R,2S,4R)-2'-isopropyl-1,7,7-trimethylspiro[bicyclo[2.2.1]heptane-2,4'-[1,3]dioxane]) | 2112 | −1.6 |
| CITRONELLYL NITRILE (3,7-dimethyloct-6-enenitrile) | 1429 | −1.6 |
| FLORHYDRAL (3-(3-isopropylphenyl)butanal) | 1568 | −2.7 |
| GERANYL ACETATE SYNTHETIC ((E)-3,7-dimethylocta-2,6-dien-1-yl acetate) | 1643 | −2.4 |
| HABANOLIDE ((E)-oxacyclohexadec-12-en-2-one) | 1978 | −2.6 |
| HEXYL ISOBUTYRATE (hexyl isobutyrate) | 1460 | −1.0 |
| MYRALDENE (4-(4-methylpent-3-en-1-yl)cyclohex-3-enecarbaldehyde) | 1613 | −2.2 |
| TRIDECENE-2-NITRILE ((E)-tridec-2-enenitrile) | 1818 | −1.5 |
| ROSACETOL (2,2,2-trichloro-1-phenylethyl acetate) | 1731 | −1.5 |
| CITRONELLYL ACETATE (3,7-dimethyloct-6-en-1-yl acetate) | 1678 | −1.7 |
| ETHYL LINALOOL ((E)-3,7-dimethylnona-1,6-dien-3-ol) | 1497 | −2.1 |
| DIPENTENE (1-methyl-4-(prop-1-en-2-yl)cyclohex-1-ene) | 1203 | −0.1 |
| GERANYL ISOBUTYRATE ((E)-3,7-dimethylocta-2,6-dien-1-yl isobutyrate) | 1901 | −1.2 |
| ISOPROPYL METHYL-2-BUTYRATE (isopropyl 2-methyl butanoate) | 1212 | −1.1 |
| RADJANOL SUPER ((E)-2-ethyl-4-(2,2,3-trimethylcyclopent-3-en-1-yl)but-2-en-1-ol) | 1829 | −2.3 |
| TERPINOLENE (1-methyl-4-(propan-2-ylidene)cyclohex-1-ene) | 1204 | −0.1 |
| ETHYL LINALYL ACETATE ((Z)-3,7-dimethylnona-1,6-dien-3-yl acetate) | 1783 | −1.1 |
| SERENOLIDE (2-(1-(3,3-dimethylcyclohexyl)ethoxy)-2-methylpropyl cyclopropanecarboxylate) | 2429 | −2.0 |
| CITRAL ((E)-3,7-dimethylocta-2,6-dienal) | 1311 | −1.8 |
| DIMETHYL OCTENONE (4,7-dimethyloct-6-en-3-one) | 1360 | −0.8 |
| GALBANONE PURE (1-(3,3-dimethylcyclohex-1-en-1-yl)pent-4-en-1-one) | 1663 | −1.9 |

-continued

| Perfumery ingredient | RECON_VOLTAE (Bohr$^3$) | LogKcaps |
|---|---|---|
| KOAVONE ((Z)-3,4,5,6,6-pentamethylhept-3-en-2-one) | 1675 | −1.6 |
| NEROLIDYLE ((Z)-3,7,11-trimethyldodeca-1,6,10-trien-3-yl acetate) | 2257 | −2.3 |
| ADOXAL (2,6,10-trimethylundec-9-enal) | 1878 | −2.5 |
| MENTHOL NATURAL (2-isopropyl-5-methylcyclohexanol) | 1357 | −2.1 |
| ALDEHYDE C 12 LAURIC (dodecanal) | 1662 | −2.9 |
| CITRONELLAL (3,7-dimethyloct-6-enal) | 1363 | −2.4 |
| COSMONE ((Z)-3-methylcyclotetradec-5-enone) | 1924 | −2.5 |
| CYCLAMEN ALDEHYDE (3-(4-isopropylphenyl)-2-methylpropanal) | 1567 | −1.6 |
| DIMETHYL BENZYL CARBINOL (2-methyl-1-phenylpropan-2-ol) | 1223 | −2.4 |
| FLORALOZONE (3-(4-ethylphenyl)-2,2-dimethylpropanal) | 1608 | −1.9 |
| HERBANATE ((2S)-ethyl 3-isopropylbicyclo[2.2.1]hept-5-ene-2-carboxylate) | 1629 | −0.7 |
| LEMONILE ((2E,6Z)-3,7-dimethylnona-2,6-dienenitrile) | 1515 | −1.5 |
| DIMETOL (2,6-dimethylheptan-2-ol) | 1320 | −2.0 |
| PIVAROSE (2,2-dimethyl-2-pheylethyl propanoate) | 1665 | −2.5 |
| PRECYCLEMONE B (1-methyl-4-(4-methylpent-3-en-1-yl)cyclohex-3-enecarbaldehyde) | 1783 | −2.2 |
| CITRONELLYL ACETATE (3,7-dimethyloct-6-en-1-yl acetate) | 1678 | −1.7 |
| ALDEHYDE C 11 UNDECYLENIC (undec-10-enal) | 1498 | −2.9 |
| ETHYL OENANTHATE (ethyl heptanoate) | 1333 | −1.5 |
| KARANAL (5-(sec-butyl)-2-(2,4-dimethylcyclohex-3-en-1-yl)-5-methyl-1,3-dioxane) | 2242 | −1.4 |
| NERYL ACETATE HC ((Z)-3,7-dimethylocta-2,6-dien-1-yl acetate) | 1643 | −2.4 |
| THIBETOLIDE (oxacyclohexadecan-2-one) | 2017 | −2.2 |
| FLOROPAL (2,4,6-trimethyl-4-phenyl-1,3-dioxane) | 1596 | −1.1 |
| GIVESCONE (ethyl 2-ethyl-6,6-dimethylcyclohex-2-enecarboxylate) | 1754 | −1.5 |
| TERPINENE GAMMA (1-methyl-4-propan-2-ylcyclohexa-1,4-diene) | 1205 | −0.4 |
| FIXOLIDE (1-(3,5,5,6,8,8-hexamethyl-5,6,7,8-tetrahydronaphthalen-2-yl)ethanone) | 2207 | −2.2 |
| CITRAL LEMAROME N ((E)-3,7-dimethylocta-2,6-dienal) | 1311 | −2.1 |
| METHYL CEDRYL KETONE (1-((1S,8aS)-1,4,4,6-tetramethyl-2,3,3a,4,5,8-hexahydro-1H-5,8a-methanoazulen-7-yl)ethanone) | 2076 | −1.9 |
| PARADISAMIDE (2-ethyl-N-methyl-N-(m-tolyl)butanamide) | 1790 | −3.0 |
| RASPBERRY KETONE (N112) (4-(4-hydroxyphenyl)butan-2-one) | 1243 | −2.4 |
| ROSYRANE SUPER (4-methylene-2-phenyltetrahydro-2H-pyran) | 1353 | −1.8 |
| NEOFOLIONE ((E)-methyl non-2-enoate) | 1418 | −2.1 |
| APHERMATE (1-(3,3-dimethylcyclohexyl)ethyl formate) | 1549 | −1.9 |
| CARYOPHYLLENE ((Z)-4,11,11-trimethyl-8-methylenebicyclo[7.2.0]undec-4-ene) | 1809 | −1.0 |
| STEMONE ((E)-5-methylheptan-3-one oxime) | 1250 | −1.7 |
| EBANOL ((E)-3-methyl-5-(2,2,3-trimethylcyclopent-3-en-1-yl)pent-4-en-2-ol) | 1832 | −2.5 |
| CYCLOMYRAL (8,8-dimethyl-1,2,3,4,5,6,7,8-octahydronaphthalene-2-carbaldehyde) | 1610 | −2.4 |
| FENCHYL ACETATE ((2S)-1,3,3-trimethylbicyclo[2.2.1]heptan-2-yl acetate) | 1628 | −2.2 |
| JASMONE CIS ((Z)-3-methyl-2-(pent-2-en-1-yl)cyclopent-2-enone) | 1379 | −1.7 |
| METHYL NONYL KETONE EXTRA (undecan-2-one) | 1532 | −1.8 |

| Perfumery ingredient | RECON_VOLTAE (Bohr$^3$) | LogKcaps |
|---|---|---|
| SYLKOLIDE ((E)-2-((3,5-dimethylhex-3-en-2-yl)oxy)-2-methylpropyl cyclopropanecarboxylate) | 2177 | −1.9 |
| MELONAL (2,6-dimethylhept-5-enal) | 1229 | −2.0 |
| BUTYL BUTYRO LACTATE (1-butoxy-1-oxopropan-2-yl butyrate) | 1680 | −0.1 |
| ALDEHYDE ISO C 11 ((E)-undec-9-enal) | 1491 | −3.0 |
| DAMASCENONE GIV ((E)-1-(2,6,6-trimethylcyclohexa-1,3-dien-1-yl)but-2-en-1-one) | 1608 | −1.5 |
| ROSALVA (dec-9-en-1-ol) | 1397 | −2.6 |
| VIRIDINE ((2,2-dimethoxyethyl)benzene) | 1281 | −2.7 |
| FRUITATE ((3aS,4S,7R,7aS)-ethyl octahydro-1H-4,7-methanoindene-3a-carboxylate) | 1617 | −1.1 |
| CITRONELLYL FORMATE (3,7-dimethyloct-6-en-1-yl formate) | 1544 | −1.9 |
| EUCALYPTOL ((1s,4s)-1,3,3-trimethyl-2-oxabicyclo[2.2.2]octane) | 1278 | −1.0 |
| IRONE ALPHA ((E)-4-(2,5,6,6-tetramethylcyclohex-2-en-1-yl)but-3-en-2-one) | 1800 | −1.5 |
| MENTHONE (2-isopropyl-5-methylcyclohexanone) | 1312 | −1.4 |
| HEXENYL-3-CIS BUTYRATE ((Z)-hex-3-en-1-yl butyrate) | 1421 | −1.2 |
| ALDEHYDE C 11 MOA (2-methyldecanal) | 1530 | −2.6 |
| CLONAL (dodecanenitrile) | 1723 | −1.0 |
| DAMASCONE ALPHA ((E)-1-(2,6,6-trimethylcyclohex-2-en-1-yl)but-2-en-1-one) | 1657 | −1.1 |
| DECENAL-4-TRANS ((E)-dec-4-enal) | 1363 | −2.8 |
| DUPICAL ((E)-4-((3aS,7aS)-hexahydro-1H-4,7-methanoinden-5(6H)-ylidene)butanal) | 1607 | −2.5 |
| FENCHYL ALCOHOL ((1S,2R,4R)-1,3,3-trimethylbicyclo[2.2.1]heptan-2-ol) | 1345 | −2.0 |
| INDOFLOR (4,4a,5,9b-tetrahydroindeno[1,2-d][1,3]dioxine) | 1245 | −2.7 |
| MALTYL ISOBUTYRATE (2-methyl-4-oxo-4H-pyran-3-yl isobutyrate) | 1398 | −0.1 |
| METHYL OCTYNE CARBONATE (methyl non-2-ynoate) | 1376 | −1.8 |
| PELARGENE (2-methyl-4-methylene-6-phenyltetrahydro-2H-pyran) | 1480 | −1.5 |
| PYRALONE (6-(sec-butyl)quinoline) | 1466 | −1.8 |
| SUPER MUGUET ((E)-6-ethyl-3-methyloct-6-en-1-ol) | 1522 | −2.7 |
| VELOUTONE (2,2,5-trimethyl-5-pentylcyclopentanone) | 1778 | −1.9 |
| RHUBAFURANE (2,2,5-trimethyl-5-pentylcyclopentanone) | 1434 | −1.9 |
| SPIROGALBANONE (1-(spiro[4.5]dec-6-en-7-yl)pent-4-en-1-one) | 1850 | −2.0 |
| DIHYDRO ANETHOLE (propanedioic acid 1-(1-(3,3-dimethylcyclohexyl)ethyl) 3-ethyl ester) | 1219 | −1.7 |
| ZINARINE (2-(2,4-dimethylcyclohexyl)pyridine) | 1557 | −2.1 |
| BIGARYL (8-(sec-butyl)-5,6,7,8-tetrahydroquinoline) | 1563 | −2.0 |
| CASSYRANE (5-tert-butyl-2-methyl-5-propyl-2H-furan) | 1624 | −1.6 |
| MANZANATE (ethyl 2-methylpentanoate) | 1202 | −1.4 |
| NONENAL-6-CIS ((Z)-non-6-enal) | 1234 | −2.5 |
| ALLYL AMYL GLYCOLATE (allyl 2-(isopentyloxy)acetate) | 1495 | −2.2 |
| DIHYDRO JASMONE (3-methyl-2-pentylcyclopent-2-enone) | 1409 | −1.7 |
| ISOCYCLOCITRAL (2,4,6-trimethylcyclohex-3-enecarbaldehyde) | 1266 | −1.8 |
| LEAF ACETAL ((Z)-1-(1-ethoxyethoxy)hex-3-ene) | 1457 | −0.7 |
| CYCLOGALBANATE (allyl 2-(cyclohexyloxy)acetate) | 1546 | −2.4 |
| LIFFAROME GIV ((Z)-hex-3-en-1-yl methyl carbonate) | 1218 | −1.5 |
| CITRATHAL R ((Z)-1,1-diethoxy-3,7-dimethylocta-2,6-diene) | 1933 | −1.1 |

-continued

| Perfumery ingredient | RECON_VOLTAE (Bohr$^3$) | LogKcaps |
|---|---|---|
| ROSYFOLIA ((1-methyl-2-(5-methylhex-4-en-2-yl)cyclopropyl)-methanol) | 1685 | −1.0 |
| (3-(4-isobutyl-2-methylphenyl)propanal) | 1700 | −2.5 |

When encapsulated in the amounts referred to hereinabove microcapsules containing perfume ingredients of GROUP 1 exhibit good resistance to leakage when suspended in mildly extractive media, such as those encountered in fabric softener or conditioning compositions, and particularly those compositions containing structured surfactants.

Those encapsulated perfume compositions described hereinabove containing perfume ingredients characterized by a RECON_VOLTAE value larger than about 1200 Bohr$^3$, wherein those ingredients are additionally characterized by having a $\log_{10}$ Kcaps greater than −3 (i.e. GROUP 1 ingredients) form additional embodiments of the present invention. Furthermore, fabric softener or conditioning compositions, particularly those containing structured surfactants, containing said encapsulated perfume compositions form further embodiments of the present invention.

A second group of perfume ingredients, so called GROUP 2 ingredients, have RECON_VOLTAE values larger than 1540 Bohr$^3$ and $\log_{10}$ Kcaps greater than −3. Perfume ingredients of GROUP 2 include but are not limited to:

| Perfumery ingredient | RECON_VOLTAE (Bohr$^3$) | LogKcaps |
|---|---|---|
| HEDIONE (methyl 3-oxo-2-pentylcyclopentaneacetate) | 1784 | −2.4 |
| ALLYL CYCLOHEXYL PROPIONATE (allyl 3-cyclohexylpropanoate) | 1606 | −2.0 |
| AGRUMEX (2-(tert-butyl)cyclohexyl acetate) | 1678 | −1.9 |
| IRISONE ALPHA ((E)-4-(2,6,6-trimethylcyclohex-2-en-1-yl)but-3-en-2-one) | 1676 | −1.8 |
| ISO E SUPER (1-(2,3,8,8-tetramethyl-1,2,3,4,5,6,7,8-octahydronaphthalen-2-yl)ethanone) | 2024 | −1.4 |
| ISORALDEINE 70 ((E)-3-methyl-4-(2,6,6-trimethylcyclohex-2-en-1-yl)but-3-en-2-one) | 1806 | −2.0 |
| NECTARYL (2-(2-(4-methylcyclohex-3-en-1-yl)propyl)cyclopentanone) | 1822 | −1.9 |
| BOISAMBRENE FORTE ((ethoxymethoxy)cyclododecane) | 2063 | −2.0 |
| BOISIRIS ((1S,2R,5R)-2-ethoxy-2,6,6-trimethyl-9-methylenebicyclo[3.3.1]nonane) | 1914 | −1.0 |
| FLOROCYCLENE ((3aR,6S,7aS)-3a,4,5,6,7,7a-hexahydro-1H-4,7-methanoinden-6-yl propionate) | 1549 | −1.6 |
| HEXYL SALICYLATE (hexyl 2-hydroxybenzoate) | 1685 | −1.6 |
| ALDEHYDE C 12 MNA PURE (2-methylundecanal) | 1661 | −2.3 |
| BUTYL CYCLOHEXYL ACETATE PARA (4-(tert-butyl)cyclohexyl acetate) | 1682 | −2.7 |
| DAMASCONE DELTA ((E)-1-(2,6,6-trimethylcyclohex-3-en-1-yl)but-2-en-1-one) | 1654 | −1.3 |
| DIMETHYL BENZYL CARBINYL BUTYRATE (2-methyl-1-phenylpropan-2-yl butyrate) | 1767 | −1.6 |
| HEXYL CINNAMIC ALDEHYDE ((E)-2-benzylideneoctanal) | 1778 | −2.5 |
| IONONE BETA ((E)-4-(2,6,6-trimethylcyclohex-1-en-1-yl)but-3-en-2-one) | 1670 | −1.6 |
| TERPINYL ACETATE (2-(4-methylcyclohex-3-en-1-yl)propan-2-yl acetate) | 1590 | −2.0 |
| GARDOCYCLENE ((3aR,6S,7aS)-3a,4,5,6,7,7a-hexahydro-1H-4,7-methanoinden-6-yl isobutyrate) | 1677 | −1.5 |
| IRISONE PURE ((E)-4-(2,6,6-trimethylcyclohex-2-en-1-yl)but-3-en-2-one) | 1676 | −1.8 |
| LILIAL (3-(4-(tert-butyl)phenyl)-2-methylpropanal) | 1738 | −2.0 |
| LINALYL ACETATE SYNTHETIC (3,7-dimethylocta-1,6-dien-3-yl acetate) | 1653 | −1.5 |
| PETALIA (2-cyclohexylidene-2-(o-tolyl)acetonitrile) | 1753 | −1.4 |

| Perfumery ingredient | RECON_VOLTAE (Bohr³) | LogKcaps |
|---|---|---|
| NEOBERGAMATE FORTE (2-methyl-6-methyleneoct-7-en-2-yl acetate) | 1650 | −1.4 |
| ISONONYL ACETATE PURE (3,5,5-trimethylhexyl acetate) | 1632 | −1.0 |
| NONADYL (6,8-dimethylnonan-2-ol) | 1579 | −1.8 |
| METHYL PAMPLEMOUSSE (6,6-dimethoxy-2,5,5-trimethylhex-2-ene) | 1632 | −1.9 |
| AMBER CORE (1-((2-(tert-butyl)cyclohexyl)oxy)butan-2-ol) | 1972 | −2.3 |
| CASHMERAN (1,1,2,3,3-pentamethyl-2,3,6,7-tetrahydro-1H-inden-4(5H)-one) | 1772 | −1.9 |
| DAMASCENONE ((E)-1-(2,6,6-trimethylcyclohexa-1,3-dien-1-yl)but-2-en-1-one) | 1608 | −1.5 |
| ETHYL SAFRANATE (ethyl 2,6,6-trimethylcyclohexa-1,3-diene-1-carboxylate) | 1579 | −2.0 |
| PEONILE (2-cyclohexylidene-2-phenylacetonitrile) | 1633 | −0.9 |
| SILVIAL (3-(4-isobutylphenyl)-2-methylpropanal) | 1700 | −2.5 |
| CITRONELLYL PROPIONATE (3,7-dimethyloct-6-en-1-yl propionate) | 1808 | −2.0 |
| CYCLOHEXYL SALICYLATE (cyclohexyl 2-hydroxybenzoate) | 1610 | −2.2 |
| BORNYL ACETATE ((2S,4S)-1,7,7-trimethylbicyclo[2.2.1]heptan-2-yl acetate) | 1631 | −1.8 |
| ALDEHYDE MANDARINE ((E)-dodec-2-enal) | 1615 | −2.7 |
| AMBERMAX (1,3,4,5,6,7-hexahydro-.beta.,1,1,5,5-pentamethyl-2H-2,4a-Methanonaphthalene-8-ethanol) | 2275 | −2.8 |
| BELAMBRE 50%/IPM ((1R,2S,4R)-2'-isopropyl-1,7,7-trimethylspiro[bicyclo[2.2.1]heptane-2,4'-[1,3]dioxane]) | 2112 | −1.6 |
| FLORHYDRAL (3-(3-isopropylphenyl)butanal) | 1568 | −2.7 |
| GERANYL ACETATE SYNTHETIC ((E)-3,7-dimethylocta-2,6-dien-1-yl acetate) | 1643 | −2.4 |
| HABANOLIDE ((E)-oxacyclohexadec-12-en-2-one) | 1978 | −2.6 |
| MYRALDENE (4-(4-methylpent-3-en-1-yl)cyclohex-3-enecarbaldehyde) | 1613 | −2.2 |
| TRIDECENE-2-NITRILE ((E)-tridec-2-enenitrile) | 1818 | −1.5 |
| ROSACETOL (2,2,2-trichloro-1-phenylethyl acetate) | 1731 | −1.5 |
| CITRONELLYL ACETATE (3,7-dimethyloct-6-en-1-yl acetate) | 1678 | −1.7 |
| GERANYL ISOBUTYRATE ((E)-3,7-dimethylocta-2,6-dien-1-yl isobutyrate) | 1901 | −1.2 |
| RADJANOL SUPER ((E)-2-ethyl-4-(2,2,3-trimethylcyclopent-3-en-1-yl)but-2-en-1-ol) | 1829 | −2.3 |
| ETHYL LINALYL ACETATE ((Z)-3,7-dimethylnona-1,6-dien-3-yl acetate) | 1783 | −1.1 |
| SERENOLIDE (2-(1-(3,3-dimethylcyclohexyl)ethoxy)-2-methylpropyl cyclopropanecarboxylate) | 2429 | −2.0 |
| GALBANONE PURE (1-(3,3-dimethylcyclohex-1-en-1-yl)pent-4-en-1-one) | 1663 | −1.9 |
| KOAVONE ((Z)-3,4,5,6,6-pentamethylhept-3-en-2-one) | 1675 | −1.6 |
| NEROLIDYLE ((Z)-3,7,11-trimethyldodeca-1,6,10-trien-3-yl acetate) | 2257 | −2.3 |
| ADOXAL (2,6,10-trimethylundec-9-enal) | 1878 | −2.5 |
| ALDEHYDE C 12 LAURIC (dodecanal) | 1662 | −2.9 |
| COSMONE ((Z)-3-methylcyclotetradec-5-enone) | 1924 | −2.5 |
| CYCLAMEN ALDEHYDE (3-(4-isopropylphenyl)-2-methylpropanal) | 1567 | −1.6 |
| FLORALOZONE (3-(4-ethylphenyl)-2,2-dimethylpropanal) | 1608 | −1.9 |
| HERBANATE ((2S)-ethyl 3-isopropylbicyclo[2.2.1]hept-5-ene-2-carboxylate) | 1629 | −0.7 |

-continued

| Perfumery ingredient | RECON_VOLTAE (Bohr$^3$) | LogKcaps |
|---|---|---|
| PIVAROSE (2,2-dimethyl-2-pheylethyl propanoate) | 1665 | −2.5 |
| PRECYCLEMONE B (1-methyl-4-(4-methylpent-3-en-1-yl)cyclohex-3-enecarbaldehyde) | 1783 | −2.2 |
| CITRONELLYL ACETATE (3,7-dimethyloct-6-en-1-yl acetate) | 1678 | −1.7 |
| KARANAL (5-(sec-butyl)-2-(2,4-dimethylcyclohex-3-en-1-yl)-5-methyl-1,3-dioxane) | 2242 | −1.4 |
| NERYL ACETATE HC ((Z)-3,7-dimethylocta-2,6-dien-1-yl acetate) | 1643 | −2.4 |
| THIBETOLIDE (oxacyclohexadecan-2-one) | 2017 | −2.2 |
| FLOROPAL (2,4,6-trimethyl-4-phenyl-1,3-dioxane) | 1596 | −1.1 |
| GIVESCONE (ethyl 2-ethyl-6,6-dimethylcyclohex-2-enecarboxylate) | 1754 | −1.5 |
| FIXOLIDE (1-(3,5,5,6,8,8-hexamethyl-5,6,7,8-tetrahydronaphthalen-2-yl)ethanone) | 2207 | −2.2 |
| METHYL CEDRYL KETONE (1-((1S,8aS)-1,4,4,6-tetramethyl-2,3,3a,4,5,8-hexahydro-1H-5,8a-methanoazulen-7-yl)ethanone) | 2076 | −1.9 |
| PARADISAMIDE (2-ethyl-N-methyl-N-(m-tolyl)butanamide) | 1790 | −3.0 |
| CARYOPHYLLENE ((Z)-4,11,11-trimethyl-8-methylenebicyclo[7.2.0]undec-4-ene) | 1809 | −1.0 |
| EBANOL ((E)-3-methyl-5-(2,2,3-trimethylcyclopent-3-en-1-yl)pent-4-en-2-ol) | 1832 | −2.5 |
| CYCLOMYRAL (8,8-dimethyl-1,2,3,4,5,6,7,8-octahydronaphthalene-2-carbaldehyde) | 1610 | −2.4 |
| FENCHYL ACETATE ((2S)-1,3,3-trimethylbicyclo[2.2.1]heptan-2-yl acetate) | 1628 | −2.2 |
| SYLKOLIDE ((E)-2-((3,5-dimethylhex-3-en-2-yl)oxy)-2-methylpropyl cyclopropanecarboxylate) | 2177 | −1.9 |
| BUTYL BUTYRO LACTATE (1-butoxy-1-oxopropan-2-yl butyrate) | 1680 | −0.1 |
| DAMASCENONE GIV ((E)-1-(2,6,6-trimethylcyclohexa-1,3-dien-1-yl)but-2-en-1-one) | 1608 | −1.5 |
| FRUITATE ((3aS,4S,7R,7aS)-ethyl octahydro-1H-4,7-methanoindene-3a-carboxylate) | 1617 | −1.1 |
| IRONE ALPHA ((E)-4-(2,5,6,6-tetramethylcyclohex-2-en-1-yl)but-3-en-2-one) | 1800 | −1.5 |
| CLONAL (dodecanenitrile) | 1723 | −1.0 |
| DAMASCONE ALPHA ((E)-1-(2,6,6-trimethylcyclohex-2-en-1-yl)but-2-en-1-one) | 1657 | −1.1 |
| DUPICAL ((E)-4-((3aS,7aS)-hexahydro-1H-4,7-methanoinden-5(6H)-ylidene)butanal) | 1607 | −2.5 |
| VELOUTONE (2,2,5-trimethyl-5-pentylcyclopentanone) | 1778 | −1.9 |
| SPIROGALBANONE (1-(spiro[4.5]dec-6-en-7-yl)pent-4-en-1-one) | 1850 | −2.0 |
| ZINARINE (2-(2,4-dimethylcyclohexyl)pyridine) | 1557 | −2.1 |
| BIGARYL (8-(sec-butyl)-5,6,7,8-tetrahydroquinoline) | 1563 | −2.0 |
| CASSYRANE (5-tert-butyl-2-methyl-5-propyl-2H-furan) | 1624 | −1.6 |
| CITRATHAL R ((Z)-1,1-diethoxy-3,7-dimethylocta-2,6-diene) | 1933 | −1.1 |
| ROSYFOLIA ((1-methyl-2-(5-methylhex-4-en-2-yl)cyclopropyl)-methanol) | 1685 | −1.0 |
| (3-(4-isobutyl-2-methylphenyl)propanal) | 1700 | −2.5 |

When employed in encapsulated perfume compositions in the amounts referred to hereinabove in accordance with the present invention, microcapsules containing GROUP 2 ingredients exhibit good resistance to leakage when suspended in harshly extractive media, such as solid and liquid laundry care detergents, and particularly those formats that are designed as unit dosage forms contained in pouches or pods, and often referred to in the art as "liquid tabs", further discussion of which is provided herein below.

Those encapsulated perfume compositions described hereinabove containing perfume ingredients characterized by a RECON_VOLTAE value larger than about 1540 Bohr$^3$, wherein those ingredients are additionally characterized by having a $\log_{10}$ Kcaps greater than −3 (i.e. GROUP 2 ingredients) form additional embodiments of the present invention. A GROUP 3 of perfume ingredients is characterized by ingredients having RECON_VOLTAE values larger than 1750 Bohr$^3$ and $\log_{10}$ Kcaps greater than −3. Perfume ingredients of GROUP 3 include but are not limited to:

| Perfumery ingredient | RECON_VOLTAE (Bohr$^3$) | LogKcaps |
|---|---|---|
| ADOXAL (2,6,10-trimethylundec-9-enal) | 1878 | −2.5 |
| AMBER CORE (1-((2-(tert-butyl)cyclohexyl)oxy)butan-2-ol) | 1972 | −2.3 |
| AMBERMAX (1,3,4,5,6,7-hexahydro-.beta.,1,1,5,5-pentamethyl-2H-2,4a-Methanonaphthalene-8-ethanol) | 2275 | −2.8 |
| AMBROCENIDE ((4aR,5R,7aS,9R)-Octahydro-2,2,5,8,8,9a-hexamethyl-4H-4a,9-methanoazuleno[5,6-d]-1,3-dioxole) | 2339 | −2.1 |
| BELAMBRE ((1R,2S,4R)-2'-isopropyl-1,7,7-trimethylspiro[bicyclo[2.2.1]heptane-2,4'-[1,3]dioxane]) | 2112 | −1.6 |
| BOISAMBRENE FORTE ((ethoxymethoxy)cyclododecane) | 2063 | −2.0 |
| BOISIRIS ((1S,2R,5R)-2-ethoxy-2,6,6-trimethyl-9-methylenebicyclo[3.3.1]nonane) | 1914 | −1.0 |
| CARYOPHYLLENE ((Z)-4,11,11-trimethyl-8-methylenebicyclo[7.2.0]undec-4-ene) | 1809 | −1.0 |
| CASHMERAN (1,1,2,3,3-pentamethyl-2,3,6,7-tetrahydro-1H-inden-4(5H)-one) | 1772 | −1.9 |
| CITRONELLYL PROPIONATE (3,7-dimethyloct-6-en-1-yl propionate) | 1808 | −2.0 |
| COSMONE ((Z)-3-methylcyclotetradec-5-enone) | 1924 | −2.5 |
| DIMETHYL BENZYL CARBINYL BUTYRATE (2-methyl-1-phenylpropan-2-yl butyrate) | 1767 | −1.6 |
| EBANOL ((E)-3-methyl-5-(2,2,3-trimethylcyclopent-3-en-1-yl)pent-4-en-2-ol) | 1832 | −2.5 |
| ETHYL LINALYL ACETATE ((Z)-3,7-dimethylnona-1,6-dien-3-yl acetate) | 1783 | −1.1 |
| FIXOLIDE (1-(3,5,5,6,8,8-hexamethyl-5,6,7,8-tetrahydronaphthalen-2-yl)ethanone) | 2207 | −2.2 |
| GERANYL ISOBUTYRATE ((E)-3,7-dimethylocta-2,6-dien-1-yl isobutyrate) | 1901 | −1.2 |
| GIVESCONE (ethyl 2-ethyl-6,6-dimethylcyclohex-2-enecarboxylate) | 1754 | −1.5 |
| HABANOLIDE ((E)-oxacyclohexadec-12-en-2-one) | 1978 | −2.6 |
| HEDIONE (methyl 3-oxo-2-pentylcyclopentaneacetate) | 1784 | −2.4 |
| HEXYL CINNAMIC ALDEHYDE ((E)-2-benzylideneoctanal) | 1778 | −2.5 |
| IRONE ALPHA ((E)-4-(2,5,6,6-tetramethylcyclohex-2-en-1-yl)but-3-en-2-one) | 1800 | −1.5 |
| ISO E SUPER (1-(2,3,8,8-tetramethyl-1,2,3,4,5,6,7,8-octahydronaphthalen-2-yl)ethanone) | 2024 | −1.4 |
| ISORALDEINE 70 ((E)-3-methyl-4-(2,6,6-trimethylcyclohex-2-en-1-yl)but-3-en-2-one) | 1806 | −2.0 |
| KARANAL (5-(sec-butyl)-2-(2,4-dimethylcyclohex-3-en-1-yl)-5-methyl-1,3-dioxane) | 2242 | −1.4 |
| METHYL CEDRYL KETONE (1-((1S,8aS)-1,4,4,6-tetramethyl-2,3,3a,4,5,8-hexahydro-1H-5,8a-methanoazulen-7-yl)ethanone) | 2076 | −1.9 |
| NECTARYL (2-(2-(4-methylcyclohex-3-en-1-yl)propyl)cyclopentanone) | 1822 | −1.9 |
| NEROLIDYLE ((Z)-3,7,11-trimethyldodeca-1,6,10-trien-3-yl acetate) | 2257 | −2.3 |
| PARADISAMIDE (2-ethyl-N-methyl-N-(m-tolyl)butanamide) | 1790 | −3.0 |

-continued

| Perfumery ingredient | RECON_VOLTAE (Bohr$^3$) | LogKcaps |
|---|---|---|
| PETALIA (2-cyclohexylidene-2-(o-tolyl)acetonitrile) | 1753 | −1.4 |
| PRECYCLEMONE B (1-methyl-4-(4-methylpent-3-en-1-yl)cyclohex-3-enecarbaldehyde) | 1783 | −2.2 |
| RADJANOL SUPER ((E)-2-ethyl-4-(2,2,3-trimethylcyclopent-3-en-1-yl)but-2-en-1-ol) | 1829 | −2.3 |
| SERENOLIDE (2-(1-(3,3-dimethylcyclohexyl)ethoxy)-2-methylpropyl cyclopropanecarboxylate) | 2429 | −2.0 |
| SYLKOLIDE ((E)-2-((3,5-dimethylhex-3-en-2-yl)oxy)-2-methylpropyl cyclopropanecarboxylate) | 2177 | −1.9 |
| THIBETOLIDE (oxacyclohexadecan-2-one) | 2017 | −2.2 |
| TRIDECENE-2-NITRILE ((E)-tridec-2-enenitrile) | 1818 | −2.2 |
| VELOUTONE (2,2,5-trimethyl-5-pentylcyclopentanone) | 1778 | −1.9 |
| SPIROGALBANONE (1-(spiro[4.5]dec-6-en-7-yl)pent-4-en-1-one) | 1850 | −2.0 |
| CITRATHAL R ((Z)-1,1-diethoxy-3,7-dimethylocta-2,6-diene) | 1933 | −1.1 |

When said ingredients are employed in encapsulated perfume compositions in the amounts referred to hereinabove in accordance with the present invention, microcapsules containing the perfume ingredients of GROUP 3 exhibit good resistance to leakage when suspended in harshly extractive media, such as encountered in shampoos, hair conditioners and other personal cleansing compositions.

Those encapsulated perfume compositions described hereinabove containing perfume ingredients characterized by a RECON_VOLTAE value larger than about 1200 Bohr$^3$, wherein those ingredients are additionally characterized by having a $\log_{10}$ K caps greater than −3 (i.e. GROUP 3 ingredients) form additional embodiments of the present invention. Furthermore, personal cleansing compositions, including shampoos, containing said encapsulated perfume compositions form still further embodiments of the present invention.

A particular challenge that faces formulators of encapsulated perfume compositions is to strike an acceptable balance between microcapsule stability (i.e. the resistance to leakage of perfume ingredients from the cores of microcapsules) and performance, that is, the ability of a microcapsule to release perfume over time at a desired rate. Typically, if microcapsules are very stable during storage in extractive bases, then they tend not to release their core contents other than in response to quite high mechanical forces. When such microcapsules are deposited on substrates, such as fabric, hair or skin, a perfume impression may only be noticeable with vigorous rubbing of the treated substrate. Such microcapsules are said to possess "post-rub" performance, but the pre-rub odour impression is weak or non-existent.

The provision encapsulated perfume compositions comprising stable microcapsules, and particularly microcapsules that are stable in aggressive or extractive media that also exhibit acceptable pre-rub odour impression is challenging.

The present invention articulates another physicochemical parameter that correlates well with pre-rub odour impression of perfume ingredients encapsulated in core shell microcapsules.

The intrinsic Pre-Rub Odour Contribution ("PROC") of a perfume ingredient is given by the concentration (wt %) of a perfume ingredient to be encapsulated, multiplied by its standard Odour Value ($OV_i$), and by its equilibrium headspace-capsule partition coefficient "Kcaps". Hence for each perfume ingredient i, a Pre-Rub Odour Contribution is defined by $PROC_i = OV_i[\log_{10} Kcaps_i + 3]$ Furthermore, the partial Pre-Rub Odour Contribution (pPROC) of an ingredient is defined as its concentration (wt %) in the perfume multiplied by its standard Odour Value ($OV_i$) and by its equilibrium headspace-capsule partition coefficient Kcaps. Hence for each perfume ingredient i, a partial Pre-Rub Odour Contribution is defined by $pPROC_i = c_i OV_i [\log_{10} Kcaps_i + 3]$ Finally, the total Pre-Rub Odour Contribution (tPROC) is the sum of the partial Pre-Rub Odour Contribution (pPROC) over all ingredients in an encapsulated perfume composition. The standard Odour Value ($OV_i$) is defined as the ratio of the standard equilibrium headspace concentration of the ingredient to the Odour Detection Threshold of this ingredient.

The term "standard equilibrium headspace concentration" used hereinabove refers to the concentration of a perfume ingredient in equilibrium with its condensed form (that is, its solid or liquid form) at a temperature of 25° C. and under a pressure of 1 atmosphere. It can be measured by using any of the quantitative headspace analysis techniques known in the art, see for example Mueller and Lamparsky in Perfumes: Art, Science and Technology, Chapter 6 "The Measurement of Odors" at pages 176-179 (Elsevier 1991). The term Odour Detection Threshold (ODT,) used herein above refers to the average concentration above which a perfume ingredient i can be perceived by a panellist and can be measured by olfactometry, as described, for example in Mueller and Lamparsky (op. cit).

The equilibrium headspace concentration may be measured as follows: 500 mg of the test compound is added to a headspace container which is then sealed. The container is then incubated at constant 25° C. until the compound reached equilibrium between the gas and the liquid phase. A defined volume of this saturated headspace (usually 0.5-1lt) is trapped on a micro filter using Porapak Q as sorbent. After filter extraction with an appropriate solvent (usually 30-100

µl methyl tert. butyl ether), an aliquot of the extract is analyzed by gas chromatography (GC). Quantification is performed by the external standard calibration method. The concentration in the original headspace can be calculated (in terms of µg/l) from the headspace volume sucked through the micro filter and the aliquot of the filter extract injected into the gas chromatograph. The final headspace concentration value of a given test compound is obtained as the mean value of three independent measurements. Further information of the technique hereinabove described may be found in the article of Etzweiler, F.; Senn E. and Neuner-Jehle N., *Ber. Bunsen-Ges. Phys. Chem.* 1984, 88, 578-583, which is hereby incorporated by reference.

The Odour Detection Threshold ($ODT_i$) may be measured by using an olfactometer. The following steps can be carried out and the odour thresholds for each compounds listed in Table hereinbelow.

The olfactometer functions on the principle of a linear dilution of an odorant in a carrier gas. The quantity of odorant displaced depends on its vapour pressure and the carrier gas flow. A constant flow of nitrogen, regulated by a flow regulator, carries the odorant from a sample container to a mixing chamber. There, the carrier gas-odour mixture is diluted with odourless air. From the mixing chamber one part of the diluted odorous air is allowed to flow via a fused silica capillary to the sniffing funnel. The flow rate through the capillary, which determines the dosage of odorous air from the mixing chamber into the sniffing funnel, depends on the opening the valve which can be regulated via PC from 1 to 256 ml in binary steps. The final dilution of the odorous air sample occurs in the glass funnel by flushing them permanently with odourless air at a flow rate of 8 lt/min. Forced-choice triangle presentation is achieved by a special automated channel setting device where only one position of a switch the odorant delivering capillary enters in the sniffing funnel, whereas in two other positions the capillary is positioned outside the funnel and where the effluent is sucked away. After each trial the channel setting is changed automatically and in a random order. The concentration is calculated from the odorants vapour pressure and from the dilution ratios that were applied in the olfactometer, assuming that vapour pressure saturation is achieved in the sample generator. As a control the concentration is determined analytically by sampling a known volume from the capillary effluent into a headspace filter and by subsequent gas chromatographic quantitation of the odourant in the desorption solution.

Each panellist (panel of 15 persons) starts sniffing at the olfactometer at a concentration level at which it perceives the odorant at medium intensity. After three correct answers in three consecutive trials (or four correct answers of five trials) at the same level, stimulus concentration is decreased by a factor of two to the next lower level, and so on, until the panellist has reached its threshold level. The final threshold value of a given odorant is obtained as the mean value of all individual threshold levels.

Encapsulated perfume compositions of the present invention displaying good pre-rub performance may be prepared by selecting perfume ingredients on the basis of their PROC values, such that the total Pre-Rub Odour Contribution of the perfume ingredients encapsulated in the composition is be between about $0.5 \times 10^6$ and $1.0 \times 10^7$, more particularly between $1 \times 10^6$ and $8 \times 10^6$ and more particularly still between $1.5 \times 10^6$ and $6 \times 10^6$.

Still further, in order to obtain encapsulated perfume compositions having optimal performance in terms of stability with respect to leakage, particularly in highly extractive/aggressive media and performance, in particular pre-rub performance, the perfume ingredients may be selected on the basis of their PROC values, such that the total Pre-Rub Odour Contribution of the perfume ingredients encapsulated in the composition should be between about $0.5 \times 10^6$ and $1 \times 10^7$, more particularly between $1 \times 10^6$ and $8 \times 10^6$ and more particularly still between $1.5 \times 10^6$ and $6 \times 10^6$, and the distribution of perfume ingredient RECON_VOLTAE and $\log_{10}$ Kcaps values are within the ranges as disclosed hereinabove.

A GROUP 4 of perfume ingredients, and their respective PROC values is listed in the Table below. It is preferred that encapsulated perfume compositions having high total PROC values are composed of the GROUP 4 ingredients specified herein below, although having regard to the teaching of the present invention, the skilled person may easily calculate the PROC values of other perfume ingredients not listed, and use them in encapsulated perfume compositions of the present invention. GROUP 4 perfumery ingredients include but are not limited to:

| Perfumery ingredient | PROC |
| --- | --- |
| MANZANATE (ethyl 2-methylpentanoate) | 99577526 |
| DAMASCONE DELTA ((E)-1-(2,6,6-trimethylcyclohex-3-en-1-yl)but-2-en-1-one) | 65924274 |
| DAMASCENONE ((E)-1-(2,6,6-trimethylcyclohexa-1,3-dien-1-yl)but-2-en-1-one) | 33149935 |
| EUCALYPTOL ((1s,4s)-1,3,3-trimethyl-2-oxabicyclo[2.2.2]octane) | 20085069 |
| ETHYL CAPROATE (ethyl hexanoate) | 16063000 |
| NONENAL-6-CIS ((Z)-non-6-enal) | 14610000 |
| ALDEHYDE C 12 MNA (2-methylundecanal) | 6849504 |
| GALBANONE PURE (1-(3,3-dimethylcyclohex-1-en-1-yl)pent-4-en-1-one) | 4793532 |
| BIGARYL (8-(sec-butyl)-5,6,7,8-tetrahydroquinoline) | 4223123 |
| MELONAL (2,6-dimethylhept-5-enal) | 3633579 |
| DAMASCONE ALPHA ((E)-1-(2,6,6-trimethylcyclohex-2-en-1-yl)but-2-en-1-one) | 1869529 |
| ROSYRANE SUPER (4-methylene-2-phenyltetrahydro-2H-pyran) | 1841920 |
| PELARGENE (2-methyl-4-methylene-6-phenyltetrahydro-2H-pyran) | 1768363 |
| SPIROGALBANONE (1-(spiro[4.5]dec-6-en-7-yl)pent-4-en-1-one) | 1489842 |
| ETHYL SAFRANATE (ethyl 2,6,6-trimethylcyclohexa-1,3-diene-1-carboxylate) | 1446690 |
| DECENAL-4-TRANS ((E)-dec-4-enal) | 1068978 |
| CASSYRANE (5-tert-butyl-2-methyl-5-propyl-2H-furan) | 911423 |
| DELPHONE (2-pentylcyclopentanone) | 771798 |
| TERPINOLENE (1-methyl-4-(propan-2-ylidene)cyclohex-1-ene) | 672048 |
| IONONE BETA ((E)-4-(2,6,6-trimethylcyclohex-1-en-1-yl)but-3-en-2-one) | 668147 |

-continued

| Perfumery ingredient | PROC |
|---|---|
| ETHYL OENANTHATE (ethyl heptanoate) | 467433 |
| ALLYL AMYL GLYCOLATE (allyl 2-(isopentyloxy)acetate) | 448677 |
| LINALOOL (3,7-dimethylocta-1,6-dien-3-ol) | 405669 |
| ISOCYCLOCITRAL (2,4,6-trimethylcyclohex-3-enecarbaldehyde) | 362665 |
| ISOPROPYL METHYL-2-BUTYRATE (isopropyl 2-methyl butanoate) | 320608 |
| FLORHYDRAL (3-(3-isopropylphenyl)butanal) | 294597 |
| DIMETOL (2,6-dimethylheptan-2-ol) | 294170 |
| ROSYFOLIA (3-(4-isobutyl-2-methylphenyl)propanal) | 279858 |
| 3-(4-isobutyl-2-methylphenyl)propanal (3-(4-isobutyl-2-methylphenyl)propanal) | 279536 |
| METHYL OCTYNE CARBONATE (methyl non-2-ynoate) | 270258 |
| JASMACYCLENE ((3aR,6S,7aS)-3a,4,5,6,7,7a-hexahydro-1H-4,7-methanoinden-6-yl acetate) | 259747 |
| CYCLOGALBANATE (allyl 2-(cyclohexyloxy)acetate) | 220660 |
| FLOROPAL (2,4,6-trimethyl-4-phenyl-1,3-dioxane) | 215929 |
| DIPENTENE (1-methyl-4-(prop-1-en-2-yl)cyclohex-1-ene) | 189713 |
| FRUITATE ((3aS,4S,7R,7aS)-ethyl octahydro-1H-4,7-methanoindene-3a-carboxylate) | 176891 |
| METHYL PAMPLEMOUSSE (6,6-dimethoxy-2,5,5-trimethylhex-2-ene) | 151438 |
| IRISONE PURE ((E)-4-(2,6,6-trimethylcyclohex-2-en-1-yl)but-3-en-2-one) | 143717 |
| IRISONE ALPHA ((E)-4-(2,6,6-trimethylcyclohex-2-en-1-yl)but-3-en-2-one) | 143714 |
| LIFFAROME ((Z)-hex-3-en-1-yl methyl carbonate) | 141869 |
| CASHMERAN (1,1,2,3,3-pentamethyl-2,3,6,7-tetrahydro-1H-inden-4(5H)-one) | 141286 |
| TETRAHYDRO LINALOOL (3,7-dimethyloctan-3-ol) | 140812 |
| CITRONELLAL (3,7-dimethyloct-6-enal) | 126286 |
| ETHYL LINALOOL ((E)-3,7-dimethylnona-1,6-dien-3-ol) | 122602 |
| LEMONILE ((2E,6Z)-3,7-dimethylnona-2,6-dienenitrile) | 112447 |
| RHUBAFURAN (2,4-dimethyl-4-phenyltetrahydrofuran) | 109862 |
| FLOROCYCLENE ((3aR,6S,7aS)-3a,4,5,6,7,7a-hexahydro-1H-4,7-methanoinden-6-yl propionate) | 109419 |
| EBANOL ((E)-3-methyl-5-(2,2,3-trimethylcyclopent-3-en-1-yl)pent-4-en-2-ol) | 106853 |
| HEXENYL-3-CIS BUTYRATE ((Z)-hex-3-en-1-yl butyrate) | 97634 |
| ISORALDEINE 70 ((E)-3-methyl-4-(2,6,6-trimethylcyclohex-2-en-1-yl)but-3-en-2-one) | 83954 |
| MENTHONE (2-isopropyl-5-methylcyclohexanone) | 83516 |
| ETHYL CAPRYLATE (ethyl octanoate) | 81140 |
| GIVESCONE (ethyl 2-ethyl-6,6-dimethylcyclohex-2-enecarboxylate) | 76022 |
| CITRONELLYL NITRILE (3,7-dimethyloct-6-enenitrile) | 71124 |
| JASMONE CIS ((Z)-3-methyl-2-(pent-2-en-1-yl)cyclopent-2-enone) | 66032 |
| FENCHYL ALCOHOL ((1S,2R,4R)-1,3,3-trimethylbicyclo[2.2.1]heptan-2-ol) | 65384 |
| RADJANOL SUPER ((E)-2-ethyl-4-(2,2,3-trimethylcyclopent-3-en-1-yl)but-2-en-1-ol) | 64782 |
| UNDECAVERTOL ((E)-4-methyldec-3-en-5-ol) | 61799 |
| DUPICAL ((E)-4-((3aS,7aS)-hexahydro-1H-4,7-methanoinden-5(6H)-ylidene)butanal) | 60602 |
| BOISAMBRENE FORTE ((ethoxymethoxy)cyclododecane) | 59050 |
| ALDEHYDE C 11 MOA (2-methyldecanal) | 58883 |
| ISO E SUPER (1-(2,3,8,8-tetramethyl-1,2,3,4,5,6,7,8-octahydronaphthalen-2-yl)ethanone) | 52929 |
| DIMETHYL OCTENONE (4,7-dimethyloct-6-en-3-one) | 51879 |
| TERPINENE GAMMA (1-methyl-4-propan-2-ylcyclohexa-1,4-diene) | 51728 |
| FRESKOMENTHE (2-(sec-butyl)cyclohexanone) | 49849 |
| HEDIONE (methyl 3-oxo-2-pentylcyclopentaneacetate) | 47438 |
| CLONAL (dodecanenitrile) | 46090 |
| GARDOCYCLENE ((3aR,6S,7aS)-3a,4,5,6,7,7a-hexahydro-1H-4,7-methanoinden-6-yl isobutyrate) | 42816 |
| HERBANATE ((2S)-ethyl 3-isopropylbicyclo[2.2.1]hept-5-ene-2-carboxylate) | 38513 |
| LILIAL (3-(4-(tert-butyl)phenyl)-2-methylpropanal) | 32603 |
| SYLKOLIDE ((E)-2-((3,5-dimethylhex-3-en-2-yl)oxy)-2-methylpropyl cyclopropanecarboxylate) | 32277 |
| GERANIOL ((E)-3,7-dimethylocta-2,6-dien-1-ol) | 32071 |
| KOAVONE ((Z)-3,4,5,6,6-pentamethylhept-3-en-2-one) | 31805 |
| ROSACETOL (2,2,2-trichloro-1-phenylethyl acetate) | 31559 |
| CYCLAMEN ALDEHYDE (3-(4-isopropylphenyl)-2-methylpropanal) | 31268 |
| ALLYL CYCLOHEXYL PROPIONATE (allyl 3-cyclohexylpropanoate) | 29587 |
| BELAMBRE 50%/IPM ((1R,2S,4R)-2'-isopropyl-1,7,7-trimethylspiro[bicyclo[2.2.1]heptane-2,4'-[1,3]dioxane]) | 27187 |
| NONADYL (6,8-dimethylnonan-2-ol) | 26158 |
| FRUTONILE (2-methyldecanenitrile) | 24822 |
| TRIDECENE-2-NITRILE ((E)-tridec-2-enenitrile) | 24181 |
| PYRALONE (6-(sec-butyl)quinoline) | 23864 |
| STEMONE ((E)-5-methylheptan-3-one oxime) | 22947 |
| CITRAL LEMAROME N ((E)-3,7-dimethylocta-2,6-dienal) | 20039 |

-continued

| Perfumery ingredient | PROC |
|---|---|
| METHYL CEDRYL KETONE (1-((1S,8aS)-1,4,4,6-tetramethyl-2,3,3a,4,5,8-hexahydro-1H-5,8a-methanoazulen-7-yl)ethanone) | 19783 |
| ALDEHYDE C 110 UNDECYLIC (undecanal) | 18200 |
| SILVIAL (3-(4-isobutylphenyl)-2-methylpropanal) | 16666 |
| ALDEHYDE C 11 UNDECYLENIC (undec-10-enal) | 15988 |
| CITRONELLOL (3,7-dimethyloct-6-en-1-ol) | 15832 |
| ROSALVA (dec-9-en-1-ol) | 14982 |
| VELOUTONE (2,2,5-trimethyl-5-pentylcyclopentanone) | 14571 |
| MYRALDENE (4-(4-methylpent-3-en-1-yl)cyclohex-3-enecarbaldehyde) | 13927 |
| AMYL SALICYLATE (pentyl 2-hydroxybenzoate) | 13880 |
| TETRAHYDRO MYRCENOL (2,6-dimethyloctan-2-ol) | 13764 |
| BOISIRIS ((1S,2R,5R)-2-ethoxy-2,6,6-trimethyl-9-methylenebicyclo[3.3.1]nonane) | 13558 |
| NECTARYL (2-(2-(4-methylcyclohex-3-en-1-yl)propyl)cyclopentanone) | 13091 |
| METHYL NONYL KETONE EXTRA (undecan-2-one) | 11831 |
| PETALIA (2-cyclohexylidene-2-(o-tolyl)acetonitrile) | 10949 |
| FLORALOZONE (3-(4-ethylphenyl)-2,2-dimethylpropanal) | 10053 |
| PEONILE (2-cyclohexylidene-2-phenylacetonitrile) | 9995 |
| AGRUMEX (2-(tert-butyl)cyclohexyl acetate) | 9864 |
| IRONE ALPHA ((E)-4-(2,5,6,6-tetramethylcyclohex-2-en-1-yl)but-3-en-2-one) | 9686 |
| ORIVONE (4-(tert-pentyl)cyclohexanone) | 9146 |
| NEOBERGAMATE FORTE (2-methyl-6-methyleneoct-7-en-2-yl acetate) | 8351 |
| ISONONYL ACETATE (3,5,5-trimethylhexyl acetate) | 7732 |
| ALLYL OENANTHATE (allyl heptanoate) | 7580 |
| DIMETHYL BENZYL CARBINYL ACETATE (2-methyl-1-phenylpropan-2-yl acetate) | 7061 |
| COSMONE ((Z)-3-methylcyclotetradec-5-enone) | 6460 |
| SERENOLIDE (2-(1-(3,3-dimethylcyclohexyl)ethoxy)-2-methylpropyl cyclopropanecarboxylate) | 5947 |
| RASPBERRY KETONE (N112) (4-(4-hydroxyphenyl)butan-2-one) | 5860 |
| ETHYL LINALYL ACETATE ((Z)-3,7-dimethylnona-1,6-dien-3-yl acetate) | 5526 |
| DIMETHYL BENZYL CARBINYL BUTYRATE (2-methyl-1-phenylpropan-2-yl butyrate) | 5269 |
| MALTYL ISOBUTYRATE (2-methyl-4-oxo-4H-pyran-3-yl isobutyrate) | 5209 |
| HEXYL SALICYLATE (hexyl 2-hydroxybenzoate) | 4862 |
| AMBER CORE (1-((2-(tert-butyl)cyclohexyl)oxy)butan-2-ol) | 4356 |
| PRECYCLEMONE B (1-methyl-4-(4-methylpent-3-en-1-yl)cyclohex-3-enecarbaldehyde) | 4350 |
| HEXYL ISOBUTYRATE (hexyl isobutyrate) | 4190 |
| ADOXAL (2,6,10-trimethylundec-9-enal) | 3827 |
| THIBETOLIDE (oxacyclohexadecan-2-one) | 3525 |
| NEOFOLIONE ((E)-methyl non-2-enoate) | 3459 |
| TERPINYL ACETATE (2-(4-methylcyclohex-3-en-1-yl)propan-2-yl acetate) | 3429 |
| FENCHYL ACETATE ((2S)-1,3,3-trimethylbicyclo[2.2.1]heptan-2-yl acetate) | 3166 |
| SUPER MUGUET ((E)-6-ethyl-3-methyloct-6-en-1-ol) | 2813 |
| KARANAL (5-(sec-butyl)-2-(2,4-dimethylcyclohex-3-en-1-yl)-5-methyl-1,3-dioxane) | 2751 |
| CITRONELLYL PROPIONATE (3,7-dimethyloct-6-en-1-yl propionate) | 2710 |
| LINALYL ACETATE SYNTHETIC (3,7-dimethylocta-1,6-dien-3-yl acetate) | 2676 |
| BUTYL CYCLOHEXYL ACETATE PARA (4-(tert-butyl)cyclohexyl acetate) | 2526 |
| CYCLOHEXYL SALICYLATE (cyclohexyl 2-hydroxybenzoate) | 2454 |
| ALDEHYDE C 12 LAURIC (dodecanal) | 2369 |
| APHERMATE (1-(3,3-dimethylcyclohexyl)ethyl formate) | 2320 |
| GERANYL ISOBUTYRATE ((E)-3,7-dimethylocta-2,6-dien-1-yl isobutyrate) | 1972 |
| CITRONELLYL ACETATE (3,7-dimethyloct-6-en-1-yl acetate) | 1744 |
| ALDEHYDE MANDARINE ((E)-dodec-2-enal) | 1675 |
| BORNYL ACETATE ((2S,4S)-1,7,7-trimethylbicyclo[2.2.1]heptan-2-yl acetate) | 1498 |
| VIRIDINE ((2,2-dimethoxyethyl)benzene) | 1437 |
| CITRONELLYL FORMATE (3,7-dimethyloct-6-en-1-yl formate) | 1414 |
| PIVAROSE (2,2-dimethyl-2-pheylethyl propanoate) | 1206 |
| MENTHOL NATURAL (2-isopropyl-5-methylcyclohexanol) | 1177 |
| AMBERMAX (1,3,4,5,6,7-hexahydro-.beta.,1,1,5,5-pentamethyl-2H-2,4a-Methanonaphthalene-8-ethanol) | 1066 |
| BUTYL BUTYRO LACTATE (1-butoxy-1-oxopropan-2-yl butyrate) | 999 |
| CITRATHAL R ((Z)-1,1-diethoxy-3,7-dimethylocta-2,6-diene) | 995 |
| HABANOLIDE ((E)-oxacyclohexadec-12-en-2-one) | 991 |
| INDOFLOR (4,4a,5,9b-tetrahydroindeno[1,2-d][1,3]dioxine) | 830 |
| CORANOL (4-cyclohexyl-2-methylbutan-2-ol) | 740 |
| CARYOPHYLLENE ((Z)-4,11,11-trimethyl-8-methylenebicyclo[7.2.0]undec-4-ene) | 609 |
| GERANYL ACETATE ((E)-3,7-dimethylocta-2,6-dien-1-yl acetate) | 593 |
| PARADISAMIDE (2-ethyl-N-methyl-N-(m-tolyl)butanamide) | 550 |

-continued

| Perfumery ingredient | PROC |
|---|---|
| FIXOLIDE (1-(3,5,5,6,8,8-hexamethyl-5,6,7,8-tetrahydronaphthalen-2-yl)ethanone) | 550 |
| NERYL ACETATE HC ((Z)-3,7-dimethylocta-2,6-dien-1-yl acetate) | 472 |
| DIMETHYL BENZYL CARBINOL (2-methyl-1-phenylpropan-2-ol) | 264 |
| HEXYL CINNAMIC ALDEHYDE ((E)-2-benzylideneoctanal) | 192 |
| NEROLIDYLE ((Z)-3,7,11-trimethyldodeca-1,6,10-trien-3-yl acetate) | 175 |

It is preferred that an encapsulated perfume composition of the present invention contains at least 3, more particularly at least 5, still more particularly at least 7, and more particularly still, at least 9 GROUP 4 perfume ingredients.

Those encapsulated perfume compositions described hereinabove additionally comprising GROUP 4 ingredients, and in particular at least 3, more particularly at least 5, still more particularly at least 7, and more particularly still, at least 9 GROUP 4 perfume ingredients represent additional aspects of the present invention.

Furthermore, fabric softener or conditioning compositions, particularly those containing structured surfactants; or solid or liquid laundry detergent compositions, and particularly those formats designed as unit dosage forms contained in pouches or pods, and often referred to in the art as "liquid tabs"; or harshly extractive media, including personal care cleansing compositions, such as shampoos, containing encapsulated perfume compositions described herein comprising GROUP 4 ingredients, form further embodiments of the present invention.

Where trivial names or trade names are used in relation to the specific perfume ingredients recited above, the applicant includes within the ambit of the invention not only proprietary perfume ingredients but also the corresponding generic ingredient. The skilled person will be entirely familiar with the correspondence between trade names, trivial names and more conventional nomenclature, such as IUPAC nomenclature, or the skilled person can easily find such correspondence in perfumery text books or other references such as the website thegoodscentscompany.com.

In a particular embodiment of the present invention, an encapsulated perfume composition is characterized in that the total Pre-Rub Odour Contribution of the encapsulated perfume ingredients is between $0.5 \times 10^6$ and $1.0 \times 10^7$, more particularly between $1 \times 10^6$ and $8 \times 10^6$ and more particularly still, between $1.5 \times 10^6$ and $6 \times 10^6$; and the distribution of RECON_VOLTAE values of encapsulated perfume ingredients is such that 70 wt % or more, 80 wt % or more, 90 wt % or more of the perfume ingredients have known RECON_VOLTAE values larger than 1200 Bohr$^3$; and from 0.1 to 30 wt %, from 1 to 20 wt %, from 1 to 10 wt % of perfume ingredients having known RECON_VOLTAE values below 1200 Bohr$^3$.

In another particular embodiment, an encapsulated perfume composition is characterized in that the total Pre-Rub Odour Contribution of the encapsulated perfume ingredients is between $0.5 \times 10^6$ and $1.0 \times 10^7$, more particularly between $1 \times 10^6$ and $8 \times 10^6$ and more particularly still between $1.5 \times 10^6$ and $6 \times 10^6$, and more particularly still between $1.5 \times 10^6$ and $6 \times 10^6$; and the distribution of known RECON_VOLTAE values of encapsulated perfume ingredients is such that 30 wt % or more, 35 wt % or more, 40 wt % or more of the perfume ingredients have known RECON_VOLTAE values larger than 1540 Bohr$^3$; and 30 wt % or more, 40 wt % or more, 50 wt % or more of the perfume ingredients have known RECON_VOLTAE values from 1200 Bohr$^3$ to 1540 Bohr$^3$; and from 0.1 to 30 wt %, from 1 to 20 wt %, from 1 to 10 wt % of perfume ingredients have known RECON_VOLTAE values below 1200 Bohr$^3$.

In another particular embodiment an encapsulated perfume composition contains encapsulated perfume ingredients characterized by a total Pre-Rub Odour Contribution between $0.5 \times 10^6$ and $1.0 \times 10^7$, more particularly $1 \times 10^6$ and $8 \times 10^6$ and more particularly still $1.5 \times 10^6$ and $6 \times 10^6$; and the distribution of known RECON_VOLTAE values of encapsulated perfume ingredients is such that from 0.5 to 30, from 1 to 25 wt %, from 5 to 20 wt % of at least one perfume ingredient have known RECON_VOLTAE values above 1750 Bohr$^3$; and 20 to 60 wt %, 25 to 55 wt %, 30 to 50 wt % of the perfume ingredients have known RECON_VOLTAE values from 1540 Bohr$^3$ to 1750 Bohr$^3$; and 5 to 50 wt %, 10 to 40 wt %, 15 to 30 wt % of the perfume ingredients have known RECON_VOLTAE values from 1200 Bohr$^3$ to 1540 Bohr$^3$ ; and from 0.1 to 30 wt %, from 1 to 20 wt %, from 1 to 10 wt % of perfume ingredients have known RECON_VOLTAE values below 1200 Bohr$^3$.

In another particular embodiment an encapsulated perfume composition contains encapsulated perfume ingredients characterized by a total Pre-Rub Odour Contribution between $0.5 \times 10^6$ and $1.0 \times 10^7$, more particularly between $1 \times 10^6$ and $8 \times 10^6$ and more particularly still between $1.5 \times 10^6$ and $6 \times 10^6$; and the distribution of known RECON_VOLTAE values of encapsulated perfume ingredients is such that 70 wt % or more, 80 wt % or more, 90 wt % or more of the perfume ingredients have known RECON_VOLTAE values larger than 1750 Bohr$^3$; and from 0.1 to 30 wt %, from 1 to 20 wt %, from 1 to 10 wt % of the perfume ingredients have RECON_VOLTAE values below 1750 Bohr$^3$.

RECON VOLTAE and $\log_{10}$ Kcaps values for other perfume ingredients, one or more of which may be employed in encapsulated perfume compositions according to the present invention, are set forth in the following table.

| Ingredient (NAME (IUPAC name)) | RECON_VOLTAE | Log Kcaps |
|---|---|---|
| ACETAL CD ((2-benzyl-1,3-dioxolan-4-yl)methanol) | 1387 | −4.0 |
| ACETAL E ((2-(1-ethoxyethoxy)ethyl)benzene) | 1531 | −1.1 |
| ACETAL R ((2-(1-propoxyethoxy)ethyl)benzene) | 1661 | −1.2 |
| ACETANISOLE (1-(4-methoxyphenyl)ethanone) | 1114 | −2.3 |
| ACETATE PA (allyl 2-phenoxyacetate) | 1407 | −3.5 |
| ACETOIN (3-hydroxybutan-2-one) | 690 | −1.4 |
| ACETOPHENONE (acetophenone) | 923 | −1.5 |

-continued

| Ingredient (NAME (IUPAC name)) | RECON_VOLTAE | Log Kcaps |
|---|---|---|
| ACETYL CARYOPHYLLENE ((Z)-4,11,11-trimethyl-8-methylenebicyclo[7.2.0]undec-4-ene) | 2092 | −1.0 |
| ACETYL ISOEUGENOL CRYSTALS ((E)-2-methoxy-4-(prop-1-en-1-yl)phenyl acetate) | 1526 | −2.8 |
| AGARBOIS (N-ethyl-N-(m-tolyl)propionamide) | 1537 | −3.0 |
| ALCOHOL C 10 DECYLIC (decan-1-ol) | 1432 | −2.7 |
| ALCOHOL C 12 LAURIC (dodecan-1-ol) | 1690 | −2.5 |
| ALCOHOL C 13 OXO (tridecan-1-ol) | 1819 | −2.4 |
| ALCOHOL C 6 HEXYLIC (hexan-1-ol) | 915 | −2.9 |
| ALCOHOL C 8 OCTYLIC (octan-1-ol) | 1173 | −3.0 |
| ALCOHOL C 9 NONYLIC (nonan-1-ol) | 1302 | −3.0 |
| ALDEHYDE C 6 HEXYLIC FOOD GRADE (hexan-1-ol) | 885 | −2.8 |
| ALDEHYDE C 7 HEPTYLIC (heptanal) | 1016 | −2.7 |
| ALDEHYDE C 8 OCTYLIC FOOD GRADE (octanal) | 1145 | −2.7 |
| ALDEHYDE C 9 ISONONYLIC (3,5,5-trimethylhexanal) | 1317 | −2.5 |
| ALDEHYDE C 9 NONYLIC FOOD GRADE (nonanal) | 1274 | −2.8 |
| ALICATE (2,6-dimethylheptan-4-yl acetate) | 1605 | −1.8 |
| ALLYL CAPROATE (allyl hexanoate) | 1307 | −1.8 |
| AMBERKETAL (3,8,8,11a-tetramethyldodecahydro-1H-3,5a-epoxynaphtho[2,1-c]oxepine) | 2339 | −4.0 |
| AMBRETTOLIDE ((Z)-oxacycloheptadec-10-en-2-one) | 2108 | −5.0 |
| AMBRINOL (2,5,5-trimethyl-1,2,3,4,4a,5,6,7-octahydronaphthalen-2-ol) | 1651 | −2.3 |
| AMBROCENIDE ((4aR,5R,7aS,9R)-Octahydro-2,2,5,8,8,9a-hexamethyl-4H-4a,9-methanoazuleno[5,6-d]-1,3-dioxole) | 2339 | −2.1 |
| AMBROFIX (3a,6,6,9a-tetramethyldodecahydronaphtho[2,1-b]furan) | 2039 | −2.0 |
| AMBROXAN (3a,6,6,9a-tetramethyl-2,4,5,5a,7,8,9,9b-octahydro-1H-benzo[e][1]benzofuran) | 2039 | −2.0 |
| AMYL ACETATE (pentyl acetate) | 1075 | −1.2 |
| AMYL BENZOATE (pentyl benzoate) | 1494 | −1.2 |
| AMYL BUTYRATE (pentyl butanoate) | 1333 | −1.6 |
| AMYL CINNAMIC ALDEHYDE ((Z)-2-benzylideneheptanal) | 1649 | −2.8 |
| AMYL PHENYL ACETATE (pentyl 2-phenylacetate) | 1623 | −2.9 |
| AMYL VINYL CARBINOL (oct-1-en-3-ol) | 1149 | −2.9 |
| ANAPEAR ((E)-methyl octa-4,7-dienoate) | 1257 | −2.8 |
| ANATOLYL (phenethyl 2-methylbutanoate) | 1625 | −2.1 |
| ANETHOLE ((E)-1-methoxy-4-(prop-1-en-1-yl)benzene) | 1175 | −1.7 |
| ANISYL ACETATE (4-methoxybenzyl acetate) | 1309 | −3.6 |
| ANISYL ALCOHOL ((4-methoxyphenyl)methanol) | 1021 | −4.0 |
| ANTHER ((2-(isopentyloxy)ethyl)benzene) | 1597 | −1.3 |
| AUBEPINE PARA CRESOL (4-methoxybenzaldehyde) | 981 | −2.1 |
| AZARBRE (3,5-diethyl-2,5-dimethylcyclohex-2-enone) | 1591 | −1.5 |
| BENZALDEHYDE (benzaldehyde) | 790 | −0.9 |
| BENZOPHENONE (benzophenone) | 1347 | −1.5 |
| BENZYL ACETATE (benzyl acetate) | 1118 | −1.6 |
| BENZYL ACETONE (4-phenylbutan-2-one) | 1180 | −1.8 |
| BENZYL ALCOHOL (phenylmethanol) | 831 | −2.6 |
| BENZYL BENZOATE (benzyl benzoate) | 1539 | −3.6 |
| BENZYL BUTYRATE (benzyl butanoate) | 1378 | −1.7 |
| BENZYL CINNAMATE (benzyl 3-phenylprop-2-enoate) | 1748 | −2.5 |
| BENZYL FORMATE (benzyl formate) | 984 | −2.0 |
| BENZYL ISOBUTYRATE (benzyl isobutanoate) | 1374 | −1.4 |
| BENZYL ISOVALERATE (benzyl 3-methylbutanoate) | 1510 | −1.4 |
| BENZYL METHYL ETHER ((methoxymethyl)benzene) | 960 | −2.2 |
| BENZYL PHENYL ACETATE (benzyl 2-phenylacetate) | 1669 | −5.2 |
| BENZYL PROPIONATE (benzyl propionate) | 1249 | −1.6 |
| BENZYL SALICYLATE (benzyl 2-hydroxybenzoate) | 1601 | −5.0 |
| BICYCLO NONALACTONE (octahydro-2H-chromen-2-one) | 1160 | −2.6 |
| BIGARADE OXIDE ((4aS,6R,7S,8aR)-3,3,6,7-tetramethyl-2,4,4a,5,6,7,8,8a-octahydrochromene) | 1610 | −1.2 |
| BISABOLENE ((E)-1-methyl-4-(6-methylhepta-2,5-dien-2-yl)cyclohex-1-ene) | 1804 | −0.8 |
| BORNEOL CRYSTALS ((1S,2S,4S)-1,7,7-trimethylbicyclo[2.2.1]heptan-2-ol) | 1345 | −2.0 |
| BOURGEONAL (3-(4-(tert-butyl)phenyl)propanal) | 1609 | −3.2 |
| BUCCOXIME ((1R,5S,E)-1,5-dimethylbicyclo[3.2.1]octan-8-one oxime) | 1402 | −2.3 |
| BUTYL ISOBUTYRATE, ISO-(2-methylpropyl 2-methylpropanoate) | 1202 | −1.7 |
| BUTYL QUINOLINE SECONDARY (6-(sec-butyl)quinoline) | 1466 | −1.8 |
| CALMODE (1,2,4-trimethoxy-5-propylbenzene) | 1602 | −3.3 |
| CALONE 1951 (7-methyl-2H-benzo[b][1,4]dioxepin-3(4H)-one) | 1228 | −0.9 |
| CALYPSONE (6-methoxy-2,6-dimethyloctanal) | 1596 | −2.5 |
| CAMPHENE ((1S,4R)-2,2-dimethyl-3-methylenebicyclo[2.2.1]heptane) | 1202 | −0.3 |
| CAMPHOR ((1S,4S)-1,7,7-trimethylbicyclo[2.2.1]heptan-2-one) | 1301 | −1.9 |

| Ingredient (NAME (IUPAC name)) | RECON_VOLTAE | Log Kcaps |
|---|---|---|
| CANTHOXAL (3-(4-methoxyphenyl)-2-methylpropanal) | 1372 | −3.3 |
| CARAMEL LACTONE (3-hydroxy-4,5-dimethylfuran-2(5H)-one) | 885 | −3.5 |
| CARVACROL (5-isopropyl-2-methylphenol) | 1217 | −2.0 |
| CARVONE LAEVO (2-methyl-5-(prop-1-en-2-yl)cyclohex-2-enone) | 1249 | −1.2 |
| CASSIONE (4-(1-3-benzodioxol-5-yl)-2-butanone) | 1360 | −2.8 |
| CELERY KETONE (3-methyl-5-propylcyclohex-2-enone) | 1262 | −1.4 |
| CENTIFOLYL (2-phenylethyl 2,2-dimethylpropanoate) | 1665 | −2.0 |
| CEPIONATE (methyl 2-(3-oxo-2-pentylcyclopentyl)acetate) | 1784 | −2.4 |
| CETALOX (3a,6,6,9a-tetramethyl-2,4,5,5a,7,8,9,9b-octahydro-1H-benzo[e][1]benzofuran) | 2039 | −2.1 |
| CETONAL (2-methyl-4-(2,6,6-trimethylcyclohex-2-en-1-yl)butanal) | 1825 | −2.6 |
| CETONE ALPHA ((E)-3-methyl-4-(2,6,6-trimethylcyclohex-2-en-1-yl)but-3-en-2-one) | 1782 | −1.6 |
| CETONE V ((E)-1-(2,6,6-trimethylcyclohex-2-en-1-yl)hepta-1,6-dien-3-one) | 2028 | −3.3 |
| CINNAMALVA ((E)-3-phenylprop-2-en-1-yl acetate) | 1075 | −2.0 |
| CINNAMIC ALCOHOL ((E)-3-phenylprop-2-en-1-ol) | 1048 | −2.4 |
| CINNAMIC ALDEHYDE ((2E)-3-phenylprop-2-enal) | 1001 | −2.0 |
| CINNAMYL ACETATE ((E)-3-phenylprop-2-en-1-yl acetate) | 1334 | −1.7 |
| CINNAMYL CINNAMATE (3-phenylprop-2-enyl 3-phenylprop-2-enoate) | 1967 | −3.2 |
| CITRAL DIMETHYL ACETAL ((E)-1,1-dimethoxy-3,7-dimethylocta-2,6-diene) | 1680 | −1.9 |
| CITRONELLYL ISOBUTYRATE (3,7-dimethyloct-6-en-1-yl isobutanoate) | 1936 | −1.3 |
| CITRONELLYL OXYACETALDEHYDE (2-((3,7-dimethyloct-6-en-1-yl)oxy)acetaldehyde) | 1679 | −3.4 |
| CIVETTONE ((Z)-cycloheptadec-9-enone) | 2180 | −2.5 |
| CLARITONE (2,4,4,7-tetramethyloct-6-en-3-one) | 1658 | −0.9 |
| CONIFERAN (2-(tert-pentyl)cyclohexyl acetate) | 1807 | −1.9 |
| CORPS CASSIS (2-(2-mercaptopropan-2-yl)-5-methylcyclohexanone) | 1483 | −2.2 |
| CORPS PAMPLEMOUSSE PURE ((4S)-4,7,7-trimethyl-6-thiabicyclo[3.2.1]octane) | 1374 | 0.1 |
| CORYLONE DRIED (2-hydroxy-3-methylcyclopent-2-enone) | 822 | −2.8 |
| COUMARIN (2H-chromen-2-one) | 985 | −1.9 |
| CREOSOL (2-methoxy-4-methylphenol) | 1021 | −2.6 |
| CRESOL PARA (p-cresol) | 830 | −1.8 |
| CRESYL ACETATE PARA (p-tolyl acetate) | 1115 | −2.2 |
| CRESYL CAPRYLATE PARA (p-tolyl octanoate) | 1892 | −2.6 |
| CRESYL ISOBUTYRATE PARA (p-tolyl isobutanoate) | 1374 | −1.9 |
| CRESYL METHYL ETHER PARA (1-methoxy-4-methylbenzene) | 959 | −1.8 |
| CRESYL PHENYL ACETATE PARA (p-tolyl 2-phenylacetate) | 1666 | −4.9 |
| CUMIN NITRILE (4-isopropylbenzonitrile) | 1246 | −1.2 |
| CUMINIC ALDEHYDE (4-isopropylbenzaldehyde) | 1177 | −1.0 |
| CUMINYL ALCOHOL ((4-isopropylphenyl)methanol) | 1217 | −2.8 |
| CYCLAL C (2,4-dimethylcyclohex-3-enecarbaldehyde) | 1138 | −1.9 |
| CYCLEMONE A (8,8-dimethyl-1,2,3,4,5,6,7,8-octahydronaphthalene-2-carbaldehyde) | 1610 | −2.4 |
| CYCLOHEXAL (4-(4-hydroxy-4-methylpentyl)cyclohex-3-enecarbaldehyde) | 1719 | −3.7 |
| CYCLOHEXYL ETHYL ACETATE (2-cyclohexylethyl acetate) | 1371 | −1.9 |
| CYCLOMETHYLENE CITRONELLOL (3-(4-methylcyclohex-3-en-1-yl)butan-1-ol) | 1425 | −1.9 |
| CYDRANE (hexyl 2-methylbutanoate) | 1588 | −0.5 |
| CYMENE PARA (1-methyl-4-propan-2-ylbenzene) | 1155 | −0.6 |
| CYPRISATE (methyl 1,4-dimethylcyclohexanecarboxylate) | 2826 | −2.0 |
| DAMASCONE BETA ((E)-1-(2,6,6-trimethylcyclohex-1-en-1-yl)but-2-en-1-one) | 1655 | −1.3 |
| DECADIENAL ((2E,4E)-deca-2,4-dienal) | 1309 | −2.2 |
| DECALACTONE DELTA (6-pentyltetrahydro-2H-pyran-2-one) | 1378 | −3.2 |
| DECALACTONE GAMMA (5-hexyloxolan-2-one) | 1386 | −3.7 |
| DECANONITRILE (decanenitrile) | 1464 | −1.5 |
| DECATONE (6-isopropyloctahydronaphthalen-2(1H)-one) | 1610 | −2.2 |
| DECEN-1-AL, CIS-4-((Z)-dec-4-enal) | 1363 | −2.8 |
| DECENAL-2-TRANS ((E)-dec-2-enal) | 1356 | −2.1 |
| DECENAL-9 (9-decenal) | 1369 | −3.3 |
| DELTA-3 CARENE ((1S,6S)-3,7,7-trimethylbicyclo[4.1.0]hept-3-ene) | 1200 | −1.0 |
| DIETHYL MALONATE (diethyl propanedioate) | 1152 | −1.4 |
| DIHEXYL FUMARATE (dihexyl-but-2-enedioate) | 2263 | −1.7 |
| DIHYDRO AMBRATE (2-(sec-butyl)-1-vinylcyclohexyl acetate) | 1865 | −2.4 |

| Ingredient (NAME (IUPAC name)) | RECON_VOLTAE | Log Kcaps |
|---|---|---|
| DIHYDRO EUGENOL (2-methoxy-4-propylphenol) | 1281 | −2.5 |
| DIHYDRO FARNESAL ((Z)-3,7,11-trimethyldodeca-6,10-dienal) | 1967 | −4.0 |
| DIHYDRO IONONE BETA (4-(2,6,6-trimethylcyclohex-1-en-1-yl)butan-2-one) | 1695 | −1.5 |
| DIHYDRO LINALOOL (3,7-dimethyloct-6-en-3-ol) | 1403 | −2.0 |
| DIHYDRO MYRCENOL (2,6-dimethyloct-7-en-2-ol) | 1410 | −2.8 |
| DIHYDRO MYRCENYL ACETATE (2,6-dimethyloct-7-en-2-yl acetate) | 1695 | −2.3 |
| DIHYDRO TERPINEOL (2-(4-methylcyclohexyl)propan-2-ol) | 1356 | −2.0 |
| DIHYDRO TERPINYL ACETATE (2-(4-methylcyclohexyl)propan-2-yl acetate) | 1639 | −1.5 |
| DIMETHYL ANTHRANILATE (methyl 2-(methylamino)benzoate) | 1206 | −3.0 |
| DIMETHYL HYDROQUINONE CRYSTALS (1,4-dimethoxybenzene) | 1022 | −2.9 |
| DIMETHYL PHENYL ETHYL CARBINOL (2-methyl-4-phenylbutan-2-ol) | 1352 | −2.2 |
| DIMYRCETOL (2,6-dimethyloct-7-en-2-ol) | 2969 | −1.9 |
| DIPHENYL METHANE (diphenylmethane) | 1320 | −1.4 |
| DIPHENYL OXIDE (oxydibenzene) | 1260 | −1.2 |
| DISPIRONE (7,9-dimethylspiro[5.5]undecan-3-one) | 1648 | −2.4 |
| DODECALACTONE DELTA (6-heptyltetrahydro-2H-pyran-2-one) | 1636 | −3.4 |
| DODECALACTONE GAMMA (5-octyloxolan-2-one) | 1644 | −3.9 |
| ESTRAGOLE (1-allyl-4-methoxybenzene) | 1180 | −1.7 |
| ETHYL 2,4-DECADIENOATE ((2E,4Z)-ethyl deca-2,4-dienoate) | 1625 | −1.5 |
| ETHYL ACETATE (ethyl acetate) | 685 | −0.7 |
| ETHYL ACETO ACETATE (ethyl 3-oxobutanoate) | 964 | −1.0 |
| ETHYL AMYL KETONE (octan-3-one) | 1146 | −1.3 |
| ETHYL BENZOATE (ethyl benzoate) | 1106 | −1.7 |
| ETHYL BUTYRATE (ethyl butanoate) | 945 | −1.2 |
| ETHYL CINNAMATE (ethyl 3-phenylprop-2-enoate) | 1317 | −1.0 |
| ETHYL ISOAMYL KETONE (6-methylheptan-3-one) | 1149 | −1.2 |
| ETHYL ISOBUTYRATE (ethyl 2-methylpropionate) | 940 | −0.8 |
| ETHYL ISOVALERATE (ethyl 3-methylbutanoate) | 1077 | −1.3 |
| ETHYL LAITONE (8-ethyl-1-oxaspiro[4.5]decan-2-one) | 1429 | −2.2 |
| ETHYL MALTOL (2-ethyl-3-hydroxy-4H-pyran-4-one) | 985 | −3.7 |
| ETHYL METHYL-2-BUTYRATE (ethyl 2-methylbutanoate) | 1069 | −0.6 |
| ETHYL PELARGONATE (ethyl nonanoate) | 1591 | −2.4 |
| ETHYL PHENYL ACETATE (ethyl 2-phenylacetate) | 1236 | −2.6 |
| ETHYL PHENYL GLYCIDATE (ethyl 3-phenyloxirane-2-carboxylate) | 1347 | −1.9 |
| ETHYL PROPIONATE (ethyl propionate) | 816 | −2.0 |
| ETHYL SALICYLATE (ethyl 2-hydroxybenzoate) | 1168 | −1.2 |
| ETHYL VANILLIN (3-ethoxy-4-hydroxybenzaldehyde) | 1168 | −2.2 |
| ETHYL-2 DIMETHYL-3,5 PYRAZINE (2-ethyl-3,5-dimethylpyrazine) | 1100 | −2.4 |
| ETHYLENE BRASSYLATE (1,4-dioxacycloheptadecane-5,17-dione) | 2096 | −3.0 |
| EUGENOL PURE (4-allyl-2-methoxyphenol) | 1242 | −2.8 |
| EUGENYL ACETATE (4-allyl-2-methoxyphenyl acetate) | 1527 | −3.5 |
| EVERNYL (methyl 2,4-dihydroxy-3,6-dimethylbenzoate) | 1362 | −3.6 |
| FARNESENE ((E)-7,11-dimethyl-3-methylenedodeca-1,6,10-triene) | 1863 | −2.2 |
| FARNESOL ((2E,6Z)-3,7,11-trimethyldodeca-2,6,10-trien-1-ol) | 1962 | −4.5 |
| FENCHONE ALPHA (1,3,3-trimethylbicyclo[2.2.1]heptan-2-one) | 1301 | −1.6 |
| FENNALDEHYDE (3-(4-methoxyphenyl)-2-methylpropanal) | 1372 | −3.3 |
| FLEURANIL (3-(4-ethylphenyl)-2,2-dimethylpropanenitrile) | 1674 | −1.7 |
| FLORALYM (2,6-dimethyloct-7-en-2-ol) | 1410 | −2.8 |
| FLORAMAT (2-(tert-butyl)cyclohexyl ethyl carbonate) | 1863 | −0.5 |
| FLORIDILE ((E)-undec-9-enenitrile) | 1560 | −2.8 |
| FLOROL (2-isobutyl-4-methyltetrahydro-2H-pyran-4-ol) | 1432 | −2.5 |
| FLOROSA (tetrahydro-4-methyl-2-(2-methylpropyl)-2H-pyran-4-ol) | 1432 | −2.5 |
| FLORYMOSS ((Z)-1-(cyclooct-3-en-1-yl)propan-1-ol) | 1451 | −2.9 |
| FOLENOX (4,4,8,8-tetramethyloctahydro-4a,7-methanonaphtho[1,8a-b]oxirene) | 1865 | −1.5 |
| FOLIONE (methyl oct-2-ynoate) | 1246 | −1.7 |
| FOLROSIA (4-isopropylcyclohexanol) | 1229 | −2.3 |
| FRAISTONE (ethyl 2-(2,4-dimethyl-1,3-dioxolan-2-yl)acetate) | 1440 | −3.1 |
| FRESCILE (3-methyldodecanenitrile) | 1859 | −1.9 |
| FRUCTONE (ethyl 2-(2-methyl-1,3-dioxolan-2-yl)acetate) | 1307 | −3.3 |
| GALAXOLIDE (4,6,6,7,8,8-hexamethyl-1,3,4,6,7,8-hexahydrocyclopenta[g]isochromene) | 2160 | −4.3 |
| GARDAMIDE (N,2-dimethyl-N-phenylbutanamide) | 1534 | −2.5 |
| GARDENOL (1-phenylethyl acetate) | 1246 | −1.7 |

-continued

| Ingredient (NAME (IUPAC name)) | RECON_VOLTAE | Log Kcaps |
|---|---|---|
| GEORGYWOOD (1-(1,2,8,8-tetramethyl-1,2,3,4,5,6,7,8-octahydronaphthalen-2-yl)ethanone) | 2037 | −1.3 |
| GERANODYLE (2-(2-hydroxypropan-2-yl)-5-methylcyclohexanol) | 1420 | −4.0 |
| GERANYL ACETONE ((E)-6,10-dimethylundeca-5,9-dien-2-one) | 1705 | −1.1 |
| GERANYL CROTONATE ((E)-3,7-dimethylocta-2,6-dien-1-yl but-2-enoate) | 1862 | −2.3 |
| GERANYL FORMATE ((E)-3,7-dimethylocta-2,6-dien-1-yl formate) | 1510 | −1.6 |
| GERANYL PHENYL ACETATE ((E)-3,7-dimethylocta-2,6-dien-1-yl 2-phenylacetate) | 2194 | −3.8 |
| GERANYL PROPIONATE ((E)-3,7-dimethylocta-2,6-dien-1-yl propionate) | 1773 | −1.6 |
| GLYCOLIERRAL (2-(8-isopropyl-6-methylbicyclo[2.2.2]oct-5-en-2-yl)-1,3-dioxolane) | 1854 | −1.6 |
| GRISALVA (3a-ethyl-6,6,9a-trimethyldodecahydronaphtho[1,2-c]furan) | 2203 | −2.6 |
| GRISAMBROL B (ethyl picolinate) | 1076 | −2.4 |
| GUAIACOL (2-methoxyphenol) | 893 | −2.9 |
| GUAIYL ACETATE (2-(3,8-dimethyl-1,2,3,4,5,6,7,8-octahydroazulen-5-yl)propan-2-yl acetate) | 2161 | −1.9 |
| GYRANE (2-butyl-4,6-dimethyl-3,6-dihydro-2H-pyran) | 1446 | −2.1 |
| HELIOTROPINE (benzo[d][1,3]dioxole-5-carbaldehyde) | 971 | −1.4 |
| HELVETOLIDE (2-(1-(3,3-dimethylcyclohexyl)ethoxy)-2-methylpropyl propionate) | 2388 | −3.1 |
| HEPTALACTONE GAMMA (5-propyloxolan-2-one) | 996 | −2.2 |
| HERBAVERT (3-ethoxy-1,1,5-trimethylcyclohexane) | 1520 | −1.4 |
| HERBOXANE (2-butyl-4,4,6-trimethyl-1,3-dioxane) | 1562 | −3.7 |
| HERCOLYN D (methyl 7-isopropyl-1,4a-dimethyl-1,2,3,4,4a,4b,5,6,7,8,10,10a-dodecahydrophenanthrene-1-carboxylate) | 2656 | −5.0 |
| HEXENAL-2-TRANS (E-hex-2-enal) | 841 | −1.7 |
| HEXENOL-2-TRANS ((E)-hex-2-en-1-ol) | 886 | −2.5 |
| HEXENOL-3-CIS ((Z)-hex-3-en-1-ol) | 876 | −2.5 |
| HEXENYL ACETATE CIS (cis-hex-3-enyl acetate) | 1165 | −1.4 |
| HEXENYL HEXENOATE CIS-3 ((Z)-(Z)-hex-3-en-1-yl hex-3-enoate) | 1644 | −3.4 |
| HEXENYL-3-CIS ACETATE ((Z)-hex-3-en-1-yl acetate) | 1162 | −1.4 |
| HEXENYL-3-CIS BENZOATE ((Z)-hex-3-en-1-yl benzoate) | 1584 | −2.4 |
| HEXENYL-3-CIS FORMATE ((Z)-hex-3-en-1-yl formate) | 1029 | −1.9 |
| HEXENYL-3-CIS ISOBUTYRATE ((Z)-hex-3-en-1-yl isobutanoate) | 1420 | −0.7 |
| HEXENYL-3-CIS METHYL-2-BUTYRATE ((Z)-hept-3-en-1-yl 2-methyl butanoate) | 1549 | −1.5 |
| HEXENYL-3-CIS PROPIONATE ((Z)-hex-3-en-1-yl propionate) | 1292 | −1.2 |
| HEXENYL-3-CIS SALICYLATE ((Z)-hex-3-en-1-yl 2-hydroxybenzoate) | 1646 | −3.5 |
| HEXENYL-3-CIS TIGLATE ((E)-(Z)-hex-3-en-1-yl 2-methylbut-2-enoate) | 1505 | −1.8 |
| HEXENYL-3-TRANS ACETATE ((E)-hex-3-enyl] acetate) | 1162 | −1.5 |
| HEXYL ACETATE (hexyl acetate) | 1202 | −1.2 |
| HEXYL BENZOATE (hexyl benzoate) | 1623 | −1.4 |
| HEXYL BUTYRATE (hexyl butanoate) | 1462 | −1.8 |
| HEXYL PROPIONATE (hexyl propionate) | 1333 | −1.5 |
| HOMOFURONOL (2-ethyl-4-hydroxy-5-methylfuran-3(2H)-one) | 1025 | −3.6 |
| HYDRATROPIC ALDEHYDE (2-phenylpropanal) | 1048 | −2.4 |
| HYDROXYCITRONELLAL DIMETHYL ACETAL (8,8-dimethoxy-2,6-dimethyloctan-2-ol) | 1831 | −3.0 |
| HYDROXYCITRONELLAL (7-hydroxy-3,7-dimethyloctanal) | 1472 | −4.2 |
| IRISANTHEME ((E)-3-methyl-4-(2,6,6-trimethylcyclohex-2-en-1-yl)but-3-en-2-one) | 1806 | −1.7 |
| IRIVAL ((E)-non-2-enenitrile) | 1301 | −1.4 |
| ISO CYCLO GERANIOL ((2,4,6-trimethylcyclohex-3-en-1-yl)methanol) | 1295 | −1.6 |
| ISOAMYL ACETATE (isopentyl acetate) | 1075 | −1.2 |
| ISOAMYL BUTYRATE (isopentyl butanoate) | 1335 | −0.5 |
| ISOAMYL PROPIONATE (isopentyl propionate) | 1206 | −1.1 |
| ISOBUTYL BENZOATE (2-methylpropyl benzoate) | 1368 | −1.4 |
| ISOBUTYL ISOBUTYRATE (2-methylpropyl 2-methylpropanoate) | 1202 | −1.7 |
| ISOBUTYL METHOXY PYRAZINE (2-methylpropyl 3-methoxypyrazine) | 1311 | −2.2 |
| ISOBUTYL PHENYLACETATE (2-methylpropyl 2-phenylacetate) | 1497 | −2.0 |
| ISOBUTYL QUINOLINE-2 (6-butan-2-yl-quinoline) | 1473 | −1.6 |
| ISOBUTYL SALICYLATE (isobutyl 2-hydroxybenzoate) | 1430 | −1.6 |
| ISOEUGENOL ((E)-2-methoxy-4-(prop-1-en-1-yl)phenol) | 1238 | −2.5 |
| ISOJASMONE T (2-hexylcyclopent-2-enone) | 1411 | −2.0 |

-continued

| Ingredient (NAME (IUPAC name)) | RECON_VOLTAE | Log Kcaps |
|---|---|---|
| ISOLONGIFOLANONE (2,2,7,7-tetramethyltricyclo[6.2.1.01,6]undecan-5-one) | 1900 | −1.5 |
| ISOMENTHONE DL (2-isopropyl-5-methylcyclohexanone) | 1315 | −1.5 |
| ISONONANOL (3,5,5-trimethylhexan-1-ol) | 1345 | −2.4 |
| ISOPENTYRATE (4-methylpent-4-en-2-yl isobutanoate) | 1434 | −1.2 |
| ISOPROPYL QUINOLINE (6-isopropylquinoline) | 1336 | −1.7 |
| ISOPULEGOL (5-methyl-2-(prop-1-en-2-yl)cyclohexanol) | 1315 | −2.3 |
| ISORALDEINE CETONE ALPHA ((E)-3-methyl-4-(2,6,6-trimethylcyclohex-2-en-1-yl)but-3-en-2-one) | 1806 | −1.6 |
| JASMAL (3-pentyltetrahydro-2H-pyran-4-yl acetate) | 1709 | −4.3 |
| JASMATONE (2-hexylcyclopentanone) | 1439 | −2.2 |
| JASMIN LACTONE DELTA ((Z)-6-(pent-2-en-1-yl)tetrahydro-2H-pyran-2-one) | 1343 | −2.4 |
| JASMIN LACTONE GAMMA ((Z)-5-(hex-3-en-1-yl)-5-methyloxolan-2-one) | 1472 | −2.4 |
| JASMOLACTONE ((E)-6-(pent-3-en-1-yl)tetrahydro-2H-pyran-2-one) | 1341 | −2.5 |
| JASMONYL (3-butyl-5-methyltetrahydro-2H-pyran-4-yl acetate) | 1708 | −3.1 |
| JASMOPYRANE (3-pentyltetrahydro-2H-pyran-4-yl acetate) | 1709 | −3.0 |
| JAVANOL ((1-methyl-2-((1,2,2-trimethylbicyclo[3.1.0]hexan-3-yl)methyl)cyclopropyl)methanol) | 1930 | −3.0 |
| KEFARENE (1-(4-methoxy-2,2,6,6-tetramethylcyclohex-3-en-1-yl)ethanone) | 1807 | −2.0 |
| KEPHALIS (4-(1-ethoxyvinyl)-3,3,5,5-tetramethylcyclohexanone) | 1936 | −2.4 |
| KOHINOOL (3,4,5,6,6-pentamethylheptan-2-ol) | 1751 | −2.1 |
| LABIENONE ((E)-2,4,4,7-tetramethylnona-6,8-dien-3-one) | 1748 | −1.4 |
| LABIENOXIME ((3E,6E)-2,4,4,7-tetramethylnona-6,8-dien-3-one oxime) | 1850 | −4.0 |
| LACTOSCATONE (2,8,8-trimethyloctahydro-1H-4a,2-(epoxymethano)naphthalen-10-one) | 1804 | −2.6 |
| LAITONE (8-isopropyl-1-oxaspiro[4.5]decan-2-one) | 1561 | −2.2 |
| LIMETOL (2,2,6-trimethyl-6-vinyltetrahydro-2H-pyran) | 1332 | −1.3 |
| LINALOOL OXIDE (2-(5-methyl-5-vinyltetrahydrofuran-2-yl)propan-2-ol) | 1395 | −2.5 |
| LINALYL CINNAMATE (3,7-dimethylocta-1,6-dien-3-yl 3-phenylprop-2-enoate) | 2286 | −2.2 |
| LINALYL FORMATE (3,7-dimethylocta-1,6-dien-3-yl formate) | 1520 | −2.0 |
| LINALYL ISOBUTYRATE (3,7-dimethylocta-1,6-dien-3-yl isobutanoate) | 1911 | −1.4 |
| LINALYL PROPIONATE (3,7-dimethylocta-1,6-dien-3-yl propionate) | 1783 | −1.9 |
| LINDENOL (2-(4-methylcyclohex-3-en-1-yl)propan-2-ol) | 1307 | −1.7 |
| LONGIFOLENE STD ((3R,3aR,8R,8aS)-4,4,8-trimethyl-9-methylenedecahydro-3,8-methanoazulene) | 1799 | −1.0 |
| MACEAL (bicyclo[2.2.2]oct-5-ene-2-carboxaldehyde) | 1573 | −3.0 |
| MAGNOLAN (2,4-dimethyl-4,4a,5,9b-tetrahydroindeno[1,2-d][1,3]dioxine) | 1509 | −3.0 |
| MAHONIAL ((4E)-9-hydroxy-5,9-dimethyl-4-decenal) | 1685 | −3.5 |
| MAJANTOL (2,2-dimethyl-3-(m-tolyl)propan-1-ol) | 1507 | −2.4 |
| MALTOL (3-hydroxy-2-methyl-4H-pyran-4-one) | 854 | −3.9 |
| MARENIL (2-(4-(tert-butyl)phenyl)acetonitrile) | 1542 | −2.1 |
| MAYOL ((4-isopropylcyclohexyl)methanol) | 1345 | −2.7 |
| MEFRANAL (3-methyl-5-phenylpentanal) | 1443 | −2.7 |
| MEFROSOL (3-methyl-5-phenylpentan-1-ol) | 1471 | −3.5 |
| MELOZONE (tricyclo[5.2.1.02,6]decane-3-carbaldehyde) | 1260 | −1.9 |
| MENTHANYL ACETATE (2-(4-methylcyclohexyl)propan-2-yl acetate) | 1639 | −1.5 |
| METAMBRATE (2-(sec-butyl)-1-methylcyclohexyl acetate) | 1772 | −1.7 |
| METHOXY MELONAL (6-methoxy-2,6-dimethylheptanal) | 1468 | −2.5 |
| METHOXY PHENYL BUTANONE (4-(4-methoxyphenyl)butan-2-one) | 1372 | −2.6 |
| METHYL ACETOPHENONE (1-(p-tolyl)ethanone) | 1051 | −1.4 |
| METHYL AMYL KETONE (heptan-2-one) | 1015 | −1.0 |
| METHYL ANTHRANILATE (methyl 2-aminobenzoate) | 1077 | −4.0 |
| METHYL BENZOATE (methyl benzoate) | 981 | −2.3 |
| METHYL CAMOMILLE (butyl 2-methylpentanoate) | 1460 | −0.2 |
| METHYL CINNAMATE (methyl 3-phenylprop-2-enoate) | 1192 | −1.6 |
| METHYL CINNAMIC ALDEHYDE ((Z)-2-methyl-3-phenylacrylaldehyde) | 1132 | −1.9 |
| METHYL CRESOTATE PARA (methyl 2-hydroxy-5-methylbenzoate) | 1172 | −2.3 |
| METHYL DECALACTONE GAMMA (5-hexyl-5-methyloxolan-2-one) | 1517 | −2.5 |
| METHYL DIANTILIS (2-ethoxy-4-(methoxymethyl)phenol) | 1338 | −3.3 |
| METHYL DIHYDRO ISOJASMONATE (methyl 3-oxo-2- | 1784 | −1.8 |

-continued

| Ingredient (NAME (IUPAC name)) | RECON_VOLTAE | Log Kcaps |
|---|---|---|
| pentylcyclopentaneacetate) | | |
| METHYL DIPHENYL ETHER (2-methoxy-1,1'-biphenyl) | 1386 | −1.9 |
| METHYL EPI JASMONATE ((Z)-methyl 2-(3-oxo-2-(pent-2-en-1-yl)cyclopentyl)acetate) | 1742 | −2.1 |
| METHYL GEOSMIN (4,4,8a-trimethyldecahydronaphthalen-4a-ol) | 1738 | −2.8 |
| METHYL HEPTENONE PURE (6-methylhept-5-en-2-one) | 1101 | −0.6 |
| METHYL HEXYL KETONE (octan-2-one) | 1144 | −1.2 |
| METHYL ISO EUGENOL ((E)-1,2-dimethoxy-4-(prop-1-en-1-yl)benzene) | 1366 | −3.0 |
| METHYL LAITONE (8-methyl-1-oxaspiro[4.5]decan-2-one) | 1299 | −2.0 |
| METHYL LINOLEATE ((9E,12E)-methyl octadeca-9,12-dienoate) | 2546 | −2.9 |
| METHYL METHYL BUTYRATE (methyl 2-methylbutanoate) | 944 | −2.2 |
| METHYL PARA-CRESOL (1-methoxy-4-methylbenzene) | 959 | −2.0 |
| METHYL PHENYL ACETATE (methyl 2-phenylacetate) | 1111 | −2.4 |
| METHYL QUINOLINE PARA (6-methylquinoline) | 1078 | −1.8 |
| METHYL SALICYLATE (methyl 2-hydroxybenzoate) | 1043 | −2.0 |
| METHYL TUBERATE PURE (4-methyl-5-pentyldihydrofuran-2(3H)-one) | 1385 | −2.6 |
| METHYL-2 BUTANOL-1 FR (2-methylbutan-1-ol) | 789 | −1.9 |
| METHYL-2-PENTENOIC ACID, 2-((E)-2-methylpent-2-enoic acid) | 903 | −1.6 |
| METHYL-3 METHOXY-3 BUTANOL (3-methoxy-3-methylbutan-1-ol) | 981 | −3.0 |
| METHYLOCTYLACETALDEHYDE MOA (2-methyl-decanal) | 1530 | −2.6 |
| MOXALONE (1a,3,3,4,6,6-hexamethyl-1a,2,3,4,5,6,7,7a-octahydronaphtho[2,3-b]oxirene) | 1992 | −2.8 |
| MUSCENONE ((Z)-3-methylcyclopentadec-5-enone) | 2053 | −2.5 |
| MUSCONE (3-methylcyclopentadecanone) | 2095 | −2.5 |
| MUSK C14 (1,4-dioxocyclohexadecane-5,16-dione) | 1967 | −3.0 |
| MUSK R1 (1,7-dioxacycloheptadecan-8-one) | 2065 | −2.9 |
| MYRALDYL ACETATE ((4-(4-methylpent-3-en-1-yl)cyclohex-3-en-1-yl)methyl acetate) | 1928 | −1.6 |
| MYRCENE 90 (7-methyl-3-methyleneocta-1,6-diene) | 1259 | −0.4 |
| MYROXIDE (2,2-dimethyl-3-(3-methylpenta-2,4-dienyl)oxirane) | 1282 | −0.9 |
| MYSTIKAL (2-methylundecanoic acid) | 1722 | −5.0 |
| NEOCASPIRENE (10-isopropyl-2,7-dimethyl-1-oxaspiro[4.5]deca-3,6-diene) | 1715 | −1.4 |
| NEROL C (3,7-dimethyl-2,6-octadien-1-ol) | 1363 | −2.1 |
| NEROLEX ((Z)-3,7-dimethylocta-2,6-dien-1-ol) | 1357 | −2.2 |
| NEROLIDOL ((E)-3,7,11-trimethyldodeca-1,6,10-trien-3-ol) | 1971 | −4.5 |
| NEROLINE (2-ethoxynaphthalene) | 1294 | −1.1 |
| NEROLIONE (1-(3-methylbenzofuran-2-yl)ethanone) | 1251 | −1.7 |
| NIRVANOLIDE ((E)-13-methyloxacyclopentadec-10-en-2-one) | 1981 | −1.8 |
| NONADIENAL ((2E,6Z)-nona-2,6-dienal) | 1187 | −1.9 |
| NONADIENOL-2,6 ((2E,6Z)-nona-2,6-dien-1-ol) | 1234 | −2.5 |
| NONADIENYL ACETATE ((2E,6Z)-nona-2,6-dien-1-yl acetate) | 1520 | −2.4 |
| NONANYL ACETATE (nonanyl acetate) | 1632 | −1.7 |
| NONENOL-6-CIS ((Z)-non-6-en-1-ol) | 1263 | −2.8 |
| NOOTKATONE CRYSTALS (4,4a-dimethyl-6-(prop-1-en-2-yl)-4,4a,5,6,7,8-hexahydronaphthalen-2(3H)-one) | 1848 | −2.5 |
| NOPYL ACETATE (2-(6,6-dimethylbicyclo[3.1.1]hept-2-en-2-yl)ethyl acetate) | 1669 | −2.1 |
| OCIMENE ((E)-3,7-dimethylocta-1,3,6-triene) | 1253 | −0.7 |
| OCTALACTONE DELTA (6-propyltetrahydro-2H-pyran-2-one) | 1119 | −2.8 |
| OCTALACTONE GAMMA (5-butyloxolan-2-one) | 1128 | −3.4 |
| OCTENOL (oct-1-en-3-ol) | 1149 | −2.9 |
| OCTENYL ACETATE (oct-1-en-3-yl acetate) | 1436 | −1.8 |
| OKOUMAL (2,4-dimethyl-2-(5,5,8,8-tetramethyl-5,6,7,8-tetrahydronaphthalen-2-yl)-1,3-dioxolane) | 2422 | −2.6 |
| ONCIDAL ((E)-2,6,10-trimethylundeca-5,9-dienal) | 1833 | −2.8 |
| OPALAL (7-isopropyl-8,8-dimethyl-6,10-dioxaspiro[4.5]decane) | 1831 | −3.0 |
| ORANGER CRYSTALS (1-(2-naphtalenyl)-ethanone) | 1262 | −2.0 |
| ORCINYL 3 (3-methoxy-5-methylphenol) | 1021 | −3.0 |
| OSYROL (7-methoxy-3,7-dimethyloctan-2-ol) | 1643 | −3.2 |
| OXANE (2-methyl-4-propyl-1,3-oxathiane) | 1264 | −1.8 |
| OXYOCTALINE FORMATE (2,4a,5,8a-tetramethyl-1,2,3,4,4a,7,8,8a-octahydronaphthalen-1-yl formate) | 1974 | −2.1 |
| PANDANOL ((2-methoxyethyl)benzene) | 1081 | −1.9 |
| PARMAVERT (1,1-dimethoxynon-2-yne) | 1547 | −1.9 |
| PEACH PURE (5-heptyldihydrofuran-2(3H)-one) | 1515 | −3.9 |
| PELARGOL (3,7-dimethyloctan-1-ol) | 1438 | −2.3 |

-continued

| Ingredient (NAME (IUPAC name)) | RECON_VOLTAE | Log Kcaps |
|---|---|---|
| PEOMOSA (2-(o-tolyl)ethanol) | 1078 | −2.4 |
| PEPPERWOOD (3,7-dimethylocta-1,6-dien-3-yl dimethylcarbamate) | 1941 | −2.6 |
| PERANAT (2-methylpentyl 2-methylpentanoate) | 1719 | −0.9 |
| PETIOLE ((2-isopropoxyethyl)benzene) | 1347 | −1.5 |
| PHARAONE (2-cyclohexylhepta-1,6-dien-3-one) | 1629 | −2.3 |
| PHENOXANOL (3-methyl-5-phenylpentan-1-ol) | 1471 | −2.5 |
| PHENOXY ACETALDEHYDE (2-phenoxyacetaldehyde) | 987 | −2.9 |
| PHENOXY ETHYL ALCOHOL (2-phenoxyethanol) | 1007 | −2.9 |
| PHENOXY ETHYL ISOBUTYRATE (2-(phenoxy)ethyl 2-methylpropionate) | 1553 | −4.3 |
| PHENYL ACETALDEHYDE (2-phenyl-ethanal) | 919 | −2.5 |
| PHENYL ACETIC ACID PURE (2-phenylacetic acid) | 981 | −2.5 |
| PHENYL ETHYL ACETATE (2-phenethyl acetate) | 1237 | −1.8 |
| PHENYL ETHYL ALCOHOL (2-phenylethanol) | 951 | −2.4 |
| PHENYL ETHYL CINNAMATE (2-phenethyl 3-phenylprop-2-enoate) | 1870 | −2.9 |
| PHENYL ETHYL FORMATE (2-phenethyl formate) | 1105 | −2.1 |
| PHENYL ETHYL ISOBUTYRATE (2-phenethyl isobutanoate) | 1496 | −2.7 |
| PHENYL ETHYL ISOVALERATE (2-phenethyl 3-methylbutanoate) | 1625 | −2.2 |
| PHENYL ETHYL PHENYLACETATE (2-phenethyl 2-phenylacetate) | 1788 | −4.0 |
| PHENYL ETHYL SALICYLATE CRYSTALS (2-phenethyl 2-hydroxybenzoate) | 1721 | −5.0 |
| PHENYL PROPIONIC ALDEHYDE (3-phenylpropanal) | 1052 | −2.6 |
| PHENYL PROPYL ACETATE (3-phenylpropyl acetate) | 1367 | −1.7 |
| PHENYL PROPYL ALCOHOL (3-phenylpropan-1-ol) | 1081 | −2.3 |
| PINENE ALPHA (2,6,6-trimethylbicyclo[3.1.1]hept-2-ene) | 1196 | −0.7 |
| PINENE BETA (6,6-dimethyl-2-methylenebicyclo[3.1.1]heptane) | 1204 | −0.8 |
| PINO ACETALDEHYDE (3-(6,6-dimethylbicyclo[3.1.1]hept-2-en-2-yl)propanal) | 1483 | −4.0 |
| PIVACYCLENE ((3aR,6S,7aS)-3a,4,5,6,7,7a-hexahydro-1H-4,7-methanoinden-6-yl pivalate) | 1851 | −1.8 |
| PLICATONE ((4aS,8aR)-7-methyloctahydro-1,4-methanonaphthalen-6(2H)-one) | 1390 | −1.7 |
| POIRENATE (ethyl 2-cyclohexylpropionate) | 1499 | −1.3 |
| POMAROSE ((2E,5E)-5,6,7-trimethylocta-2,5-dien-4-one) | 1443 | −0.9 |
| PRECARONE ((1S,4R,6S)-4,7,7-trimethyl-4-(3-methylbut-2-en-1-yl)bicyclo[4.1.0]heptan-3-one) | 1887 | −3.3 |
| PRENYL ACETATE (3-methylbut-2-en-1-yl acetate) | 1039 | −2.2 |
| PROPYL DIANTILIS (2-ethoxy-4-(isopropoxymethyl)phenol) | 1606 | −2.0 |
| PRUNOLIDE (5-pentyldihydrofuran-2(3H)-one) | 1257 | −3.7 |
| QUINTONE (2-pentylcyclopentanone) | 1313 | −1.9 |
| RESEDAL (2-(cyclohexylmethyl)-4,4,6-trimethyl-1,3-dioxane) | 1726 | −1.4 |
| RHUBOFIX ((2R,8aS)-3',6-dimethyl-3,4,4a,5,8,8a-hexahydro-1H-spiro[1,4-methanonaphthalene-2,2'-oxirane]) | 1571 | −1.2 |
| RHUBOFLOR ((4aR,8aS,E)-6-ethylideneoctahydro-2H-5,8-methanochromene) | 1400 | −1.7 |
| ROSANTOLENE (1-(ethoxymethyl)-2-methoxybenzene) | 1277 | −2.2 |
| ROSAPHEN (2-methyl-5-phenylpentan-1-ol) | 1471 | −2.5 |
| ROSE OXIDE (4-methyl-2-(2-methylprop-1-en-1-yl)tetrahydro-2H-pyran) | 1320 | −2.4 |
| ROSSITOL (3-isobutyl-1-methylcyclohexanol) | 1489 | −2.3 |
| SAFRALEINE (2,3,3-trimethyl-2,3-dihydro-1H-inden-1-one) | 1390 | −1.8 |
| SAFRANAL (2,6,6-trimethylcyclohexa-1,3-dienecarbaldehyde) | 1263 | −2.4 |
| SANDELA CONCENTRATED (3-((1R,2S,4R,6R)-5,5,6-trimethylbicyclo[2.2.1]heptan-2-yl)cyclohexanol) | 1989 | −2.8 |
| SCENTENAL ((3aR,4R,6S,7R,7aR)-6-methoxyoctahydro-1H-4,7-methanoindene-1-carbaldehyde) | 1453 | −3.2 |
| SCLARENE (4,5,6,7,8,9,10,11,12,13-decahydrocyclododeca[d]oxazole) | 1680 | −1.7 |
| SHISOLIA (4-vinylcyclohex-1-enecarbaldehyde) | 1103 | −1.9 |
| SKATOLE (3-methyl-1H-indole) | 998 | −3.9 |
| SPIRAMBRENE (2',2',3,7,7-pentamethylspiro[bicyclo[4.1.0]heptane-2,5'-[1,3]dioxane]) | 2037 | −2.9 |
| STRAWBERRY PURE (ethyl methyl phenyl glycidate) | 1481 | −2.0 |
| STYRALLYL ACETATE (1-phenylethyl acetate) | 1246 | −2.0 |
| STYRALLYL PROPIONATE (1-phenylethyl propionate) | 1377 | −1.6 |
| SUPERFIX (1,1,3-trimethyl-3-phenyl-2,3-dihydro-1H-indene) | 1959 | −1.9 |
| SYRINGA ALDEHYDE (2-(p-tolyl)acetaldehyde) | 1046 | −3.0 |
| SYVERTAL (2-(heptan-3-yl)-1,3-dioxolane) | 1428 | −3.0 |
| TANAISONE ((Z)-1-(cyclooct-3-en-1-yl)ethanone) | 1275 | −1.4 |
| TANGERINOL ((E)-6,10-dimethylundeca-5,9-dien-2-yl acetate) | 2033 | −1.8 |
| TERPINENE ALPHA (1-methyl-4-propan-2-ylcyclohexa-1,3-diene) | 1194 | −0.5 |

-continued

| Ingredient (NAME (IUPAC name)) | RECON_VOLTAE | Log Kcaps |
|---|---|---|
| TERPINEOL PURE (2-(4-methylcyclohex-3-en-1-yl)propan-2-ol) | 1307 | −2.0 |
| TETRAHYDRO CITRAL (3,7-dimethyloctanal) | 1409 | −2.4 |
| TETRAHYDRO LINALYL ACETATE (3,7-dimethyloctan-3-yl acetate) | 1733 | −1.9 |
| THIOGERANIOL ((E)-3,7-dimethylocta-2,6-diene-1-thiol) | 1458 | −1.1 |
| THYMOL CRYSTALS (2-isopropyl-5-methylphenol) | 1217 | −1.8 |
| TIMBEROL (1-(2,2,6-trimethylcyclohexyl)hexan-3-ol) | 2040 | −2.1 |
| TOLYL ALDEHYDE PARA (4-methylbenzaldehyde) | 918 | −0.7 |
| TOSCANOL (1-(cyclopropylmethyl)-4-methoxybenzene) | 1261 | −1.9 |
| TRICYCLAL (2,4-dimethylcyclohex-3-enecarbaldehyde) | 1138 | −1.7 |
| TRIDECENAL-2-TRANS ((E)-tridec-2-enal) | 1744 | −2.5 |
| TRIFERNAL (3-phenylbutanal) | 1178 | −2.2 |
| TRIMOFIX O (1-((2E,5Z,9Z)-2,7,8-trimethylcyclododeca-2,5,9-trien-1-yl)ethanone) | 2093 | −3.0 |
| TROPIONAL (3-(benzo[d][1,3]dioxol-5-yl)-2-methylpropanal) | 1361 | −2.6 |
| ULTRAVANIL (2-ethoxy-4-methylphenol) | 1146 | −2.3 |
| UNDECALACTONE DELTA (6-hexyltetrahydro-2H-pyran-2-one) | 1507 | −3.3 |
| UNDECATRIENE ((3E,5Z)-undeca-1,3,5-triene) | 1379 | −0.8 |
| UNDECENE 2 NITRILE ((E)-undec-2-enenitrile) | 1559 | −1.5 |
| VALEROLACTONE GAMMA (5-methyloxolan-2-one) | 740 | −2.3 |
| VANILLIN (4-hydroxy-3-methoxybenzaldehyde) | 1043 | −3.1 |
| VANITROPE ((E)-2-ethoxy-5-(prop-1-en-1-yl)phenol) | 1363 | −1.9 |
| VELVIONE ((Z)-cyclohexadec-5-enone) | 2050 | −1.7 |
| VERDALIA ((3aS,4R,6S,7R,7aR)-6-methoxy-3a,4,5,6,7,7a-hexahydro-1H-4,7-methanoindene) | 1267 | −2.1 |
| VERDOL (2-(tert-butyl)cyclohexanol) | 1395 | −2.5 |
| VERNALDEHYDE (1-methyl-4-(4-methylpentyl)cyclohex-3-enecarbaldehyde) | 1826 | −2.3 |
| VERTOFIX COEUR (1-((1S,8aS)-1,4,4,6-tetramethyl-2,3,3a,4,5,8-hexahydro-1H-5,8a-methanoazulen-7-yl)ethanone) | 2094 | −1.9 |
| VETIKOL ACETATE/CORPS RHUBARB (4-methyl-4-phenylpentan-2-yl acetate) | 1803 | −2.4 |
| VETYNAL ((2R,5R,8S)-4,4,8-trimethyltricyclo[6.3.1.02,5]dodecan-1-yl acetate) | 2192 | −3.7 |
| VIOLET NITRILE ((2E,6Z)-nona-2,6-dienenitrile) | 1261 | −1.6 |
| VIOLIFF (undec-10-enenitrile) | 1400 | −1.5 |
| YARA YARA (2-methoxynaphthalene) | 1169 | −1.8 |

In another aspect of the present invention, there is provided a consumer product comprising an encapsulated perfume composition as herein defined.

The amount of encapsulated perfume composition incorporated in consumer products according to the present invention may vary according to the particular application in which it is employed and on the perfume loading in the encapsulated perfume compositions. For detergent applications for example, one may employ encapsulated perfume composition in amounts from 0.01 to 3% by weight of perfume composition based on the total weight of the detergent.

The encapsulated perfume compositions according to the present invention may be employed in all manner of household care, laundry care and personal care products, including cosmetics. Representative examples of the products include but are not limited to all purpose household cleaners, dishwashing liquids and powders, laundry detergent compositions and fabric conditioners, scent-boosters used in laundry applications, body washes, soaps, shampoos, hair conditioners, skin care creams, and the like.

The formulations and ingredients of household, laundry and personal care products, as well as cosmetics in which encapsulated perfume compositions of the present invention may be employed are generally known to those skilled in the art. Reference may be made to the following works which are incorporated herein by reference:

Formulating Detergents and Personal Care Products: A guide to Product Development, by L Ho Tan Tai, ISBN 1-893997-10-3 published by the AOCS Press. Also to Volume 67 of the Surfactant Science Series Liquid Detergents ISBN 0-8247-9391-9 (Marcel Dekker Inc), as well as to the following patents or patent applications: Fabric softener and conditioner ingredients and formulations are disclosed in U.S. Pat. Nos. 6,335,315; 5,674,832; 5,759,990; 5,877,145; 5,574,179; laundry detergent ingredients and formulations are disclosed in U.S. Pat. Nos. 5,929,022; 5,916,862; 5,731,278; 5,470,507; 5,466,802; 5,460,752; and 5,458,810; and personal care product ingredients and formulations, in particular shampoos and hair conditioner formulations and ingredients are described in U.S. Pat. Nos. 6,162,423; 5,968,286; 5,935,561; 5,932,203; 5,837,661; 5,776,443; 5,756,436; 5,661,118; and 5,618,523.

Likewise, the levels at which encapsulated perfume compositions may be incorporated into the aforementioned products is also conventional, and may vary depending upon the particular product in which the composition is being incorporated. For example, the compositions may be employed in amounts of about 0.001 wt % to about 99.9 wt % based on the weight of the consumer product, more particularly from about 0.005 wt % to about 50 wt %, still more particularly about 0.01 wt % to about 20 wt %, and more particularly still about 0.1 wt % to about 5 wt %.

Encapsulated perfume compositions comprising microcapsules characterized by shells that are bi-layer or multi-layer were found to be sufficiently leakage stable as to be suitable for incorporation into particularly aggressive (or extractive) media containing high levels of surfactants and/or so-called unstructured surfactants. Representative of such media include fabric softening or conditioning products, and personal cleansing compositions such as body washes, shampoos and hair conditioners, and in particular those containing quaternized ester surfactants (so-called "esterquats") and non-ionic surfactants.

Un-structured surfactants are relatively free to extract perfume ingredients by forming micelles or vesicles around them, and solubilize them. They can be contrasted with "structured surfactants", which are essentially immobilized in a structure, such as a liquid crystalline, generally lamellar phase (sometimes called "mesophases") and are thus generally unavailable to form micelles or vesicles, and are less aggressive or extractive as a result.

Unstructured systems are essentially transparent, clear systems, whereas structured systems are essentially opaque, cloudy, turbid, opalescent, or display optical streaks when stirred or poured.

In view of the surprising stability of encapsulated perfume compositions comprising microcapsules having bi-layer or multi-layer shells, they were also found to be particularly suitable for use in bleach-containing consumer products.

Inorganic bleaches include perhydrate salts such as perborate, percarbonate, perphosphate, persulfate and persilicate salts. The inorganic perhydrate salts are normally the alkali metal salts.

Organic bleaches can include organic peroxyacids including diacyl and tetraacylperoxides, diperoxydodecanedioc acid, diperoxytetradecanedioc acid, and diperoxyhexadecanedioc acid. Other organic bleaches include the peroxy acids, particular examples being the alkylperoxy acids and the arylperoxy acids. Representative examples include (a) peroxybenzoic acid and its ring-substituted derivatives, such as alkylperoxybenzoic acids, but also peroxy-a-naphthoic acid and magnesium monoperphthalate; (b) the aliphatic or substituted aliphatic peroxy acids, such as peroxylauric acid, peroxystearic acid, ε-phthalimidoperoxycaproic acid[phthaloiminoperoxyhexanoic acid (PAP)], o-carboxybenzamidoperoxycaproic acid, N-nonenylamidoperadipic acid and N-nonenylamidopersuccinates; and (c) aliphatic and aralimphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyldi (6-aminopercaproic acid).

Bleach activators can include organic peracid precursors that enhance the bleaching action in the course of cleaning at temperatures of 60° C. and below. Bleach activators include compounds which, under perhydrolysis conditions, give aliphatic peroxoycarboxylic acids having from 1 to 10 carbon atoms, in particular from 2 to 4 carbon atoms, and/or optionally substituted perbenzoic acid. Suitable substances bear O-acyl and/or N-acyl groups of the number of carbon atoms specified and/or optionally substituted benzoyl groups.

Mention is made in particular to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), carboxylic anhydrides, in particular phthalic anhydride, acylated polyhydric alcohols, in particular triacetin, ethylene glycol diacetate and 2,5-diacetoxy-2,5-dihydrofuran and also triethylacetyl citrate (TEAC).

Bleach catalysts may be employed, and include the manganese triazacyclononane and related complexes (U.S. Pat. Nos. 4,246,612, 5,227,084); Co, Cu, Mn and Fe bispyridylamine and related complexes (U.S. Pat. No. 5,114, 611); and pentamine acetate cobalt(III) and related complexes (U.S. Pat. No. 4,810,410).

The encapsulated perfume compositions of the present invention, and particularly those containing microcapsules characterized by a bi-layer or multi-layer shell, are particularly suitable for use in products taking the form of single unit doses contained, for example, in water-dissolvable packaging, such as pouches or pods. Because these products are single dose and of relatively small size (typically about 10 to 20 ml volume), they are provided with a relatively low dose of detergent composition, and furthermore, because the packaging enclosing the detergent is water-soluble, or at least disintegrates readily in water, the composition necessarily contains a small volume of highly concentrated surfactant, and therefore represents a very aggressive medium in which to incorporate microcapsules.

These pouch formats can contain various compositions such as laundry detergents, dishwashing compositions or cleaning compositions for household care, and also shampoos, body washes and other personal care compositions, and they will contain light duty and heavy duty detergent compositions commonly employed in such compositions.

In pouches comprising laundry, laundry additive and/or fabric enhancer compositions, the compositions may comprise one or more of the following non-limiting list of ingredients: fabric care benefit agent; detersive enzyme; deposition aid; rheology modifier; builder; bleach; bleaching agent; bleach precursor; bleach booster; bleach catalyst; polyglycerol esters; whitening agent; pearlescent agent; enzyme stabilizing systems; scavenging agents including fixing agents for anionic dyes, complexing agents for anionic surfactants, and mixtures thereof; optical brighteners or fluorescers; polymer including but not limited to soil release polymer and/or soil suspension polymer; dispersants; antifoam agents; non-aqueous solvent; fatty acid; suds suppressors, e.g., silicone suds suppressors (see: U.S. Publication No. 2003/0060390 A1, ¶65-77); cationic starches (see: US 2004/0204337 A1 and US 2007/0219111 A1); scum dispersants (see: US 2003/0126282 A1); substantive dyes; hueing dyes (see: US 2014/0162929A1); colorants; opacifier; antioxidant; hydrotropes such as toluenesulfonates, cumenesulfonates and naphthalenesulfonates; color speckles; colored beads, spheres or extrudates; clay softening agents; anti-bacterial agents. Additionally or alternatively, the compositions may comprise surfactants, quaternary ammonium compounds, and/or solvent systems. Quaternary ammonium compounds may be present in fabric enhancer compositions, such as fabric softeners, and comprise quaternary ammonium cations.

Preferred surfactants are anionic, cationic, amphoteric or non-ionic surfactants, and mixtures thereof. Typically, surfactants are present in the liquid detergent composition at levels from 30 to 70 wt %.

Detersive surfactants utilized can be of the anionic, nonionic, zwitterionic, ampholytic or cationic type or can comprise compatible mixtures of these types. More preferably surfactants are selected from the group consisting of anionic, nonionic, cationic surfactants and mixtures thereof. Preferably the compositions are substantially free of betaine surfactants. Detergent surfactants useful herein are described in U.S. Pat. Nos. 3,664,961; 3,919,678; 4,222, 905; and 4,239,659. Anionic and nonionic surfactants are preferred.

If mixtures or non-ionic and ionic surfactant are present, then the weight ratio of non-ionic to ionic surfactants is from 10:1 to 1:10. Useful anionic surfactants can themselves be of several different types. For example, water-soluble salts of the higher fatty acids, i.e., "soaps", are useful anionic surfactants in the compositions herein. This includes alkali metal soaps such as the sodium, potassium, ammonium, and alkyl ammonium salts of higher fatty acids containing from about 8 to about 24 carbon atoms, and preferably from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Additional non-soap anionic surfactants which are suitable for use herein include the water-soluble salts, preferably the alkali metal, and ammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.) Examples of this group of synthetic surfactants include: a) the sodium, potassium and ammonium alkyl sulfates, especially those obtained by sulfating the higher alcohols ($C_8$-$C_{18}$) such as those produced by reducing the glycerides of tallow or coconut oil; b) the sodium, potassium and ammonium alkyl polyethoxylate sulfates, particularly those in which the alkyl group contains from 10 to 22, preferably from 12 to 18 carbon atoms, and wherein the polyethoxylate chain contains from 1 to 15, preferably 1 to 6 ethoxylate moieties; and c) the sodium and potassium alkylbenzene sulfonates in which the alkyl group contains from about 9 to about 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average number of carbon atoms in the alkyl group is from about 11 to 13, abbreviated as $C_{11}$-$C_{13}$ LAS.

Preferred nonionic surfactants are those of the formula $R_1(OC_2H_4)_nOH$, wherein $R_1$ is a $C_{10}$-$C_{16}$ alkyl group or a $C_8$-$C_{12}$ alkyl phenyl group, and n is from 3 to about 80. Particularly preferred are condensation products of $C_{12}$-$C_{15}$ alcohols with from about 5 to about 20 moles of ethylene oxide per mole of alcohol, e.g., $C_{12}$-$C_{13}$ alcohol condensed with about 6.5 moles of ethylene oxide per mole of alcohol.

The liquid composition may comprise from 30% to 70% by weight of surfactants comprising alkyl or alkenyl moieties having more than 6 carbon atoms, as disclosed in WO 2006/066654A1.

Laundry detergent compositions may have a pH of about 6 to about 10, about 6.5 to about 8.5, about 7 to about 7.5, or about 8 to about 10, wherein the pH of the detergent is defined as the pH of an aqueous 10% (weight/volume) solution of the detergent at 20±2° C.

The level of water in the liquid detergent composition is such that the water-soluble polymer forming the pouch does not dissolve by contact with the base. The level of water in the liquid detergent composition is less than 50% by weight and preferably less than 10% by weight of the liquid detergent composition. The neutralizing agent is preferably an organic base selected from amines, such as monoethanolamine, triethanolamine, organic Lewis bases, and mixtures thereof, but inorganic bases, such as sodium hydroxide, potassium hydroxide and ammonium hydroxide, can also be used. The level of neutralizing agent in the composition is typically from 5 to 15% by weight of the liquid detergent composition, although lower or higher levels can also be used.

Preferred solvents are those solvents which do not dissolve the water-soluble polymer forming the pouch. These solvents may have a low polarity or a high polarity. Low polarity solvents include typically linear and/or branched paraffin hydrocarbons. High polarity, water-soluble or partially soluble, or water miscible solvents include typically alcohols, such as methanol, ethanol, propanol, isopropanol, butanol; diols, such as 1,2-propanediol, 1,3-propanediol, glycerol, sorbitol, 2-amino-2-ethyl propanol, ethers, polyethers, short chain di-, tri- N-substituted alkylamines, short chain alkyl amides, short chain alkyl carboxylic acid lower alkyl esters, ketones, such as short chain alkyl ketones, including acetone. The liquid composition may comprise from 10% to 70% by weight of water-soluble solvents having molecular weight higher than 70 g/mol as disclosed in WO 2006/066654A1.

In another particular embodiment of the invention, the encapsulated perfume composition may be incorporated into a category of consumer products known as "scent boosters".

Scent booster products may be liquid or solid products. They are characterized in that they do not contain any actives, such as surfactants; they merely provide a suspending medium for perfume compositions, both in encapsulated form and optionally also in the form of free perfume oil.

A particularly suitable suspending medium for encapsulated perfume compositions in scent booster products is polyethylene glycol (PEG). The PEG may have a molecular weight of between 5,000 to 11,000, and more particularly about 8,000.

Scent booster products are disclosed in U.S. Pat. No. 7,867,968, which is herein incorporated in its entirety.

Given the fact that scent booster products do not contain actives, such as surfactants, stability issues do not arise and so the formulator's latitude to incorporate encapsulated perfume compositions into such products is greater. Accordingly, scent booster products may contain a wider concentration range of perfume. In particular, the encapsulated perfume compositions may be applied to scent booster products at levels that provide the consumer product with about 5 to 50 wt % of perfume composition based on the weight of the consumer product.

There now follows a series of Examples that serve to illustrate embodiments of the present invention. It will be understood that these Examples are illustrative, and the invention is not to be considered as being restricted thereto.

EXAMPLE 1

Preparation of Aminoplast Microcapsules

Aminoplast microcapsules were prepared according to the following method:
1. Adding and dissolving a polymer stabilizer (ZeMac® E400, ex Vertellus) in water under moderate shear mixing.
2. Adjusting the temperature to 35±2° C., the pH to 4.6±2 with NaOH, then adding an an alkylolated triamine pre-condensate (Luracoll SD, ex BASF), urea and perfume composition.
3. Emulsifying the system under moderate to high shear mixing, wherein the stirring speed and the geometry of the mixer is defined as a function of the desired average microcapsule size range and microcapsule size distribution.

4. Increasing the temperature to 88° C.±1° C. over a period of 75 min, then leaving the reaction at 88 C.±2° C. during 2h15.
5. Increasing the temperature to 88° C.±1° C. over a period of 75 min, then leaving the reaction at 88 C.±2° C. during 35 min. Adding a second portion of the alkylolated triamine or triamine pre-condensate and formic acid.
6. Adding ethylene urea as formaldehyde scavenger while the slurry is still hot (88° C.) for 10 min
7. Cooling the system to room temperature.
8. Adding Carbopol ETD 2561 in solution and leaving the agitation constant 1 h, at 129 rpm, then adding NaOH and optionally adjusting the pH within the range from 6 to 6.6 with formic acid.

EXAMPLE 2

Colouration of the Microcapsules

For three different encapsulated perfume compositions, the three coordinates L, a and b according to CIELAB scale were determined and ΔE was calculated in comparison to entry 1. Therein, the L value gives an information about the lightness of the colour, the a value indicates the position on the red vs. green axis and the b value indicates the position on the yellow vs. blue axis. ΔE is the calculated total colour difference.

TABLE 1

| Entry | Terpolymer | No. of layers in the shell | L | a | b | ΔE |
|---|---|---|---|---|---|---|
| 1 | Inventive composition | 2 | 77.13 | −0.46 | 4.92 | — |
| 2 | Comparative | 2 | 68.30 | 6.05 | 17.48 | 16.30 |
| 3 | Inventive | 1 | 76.91 | −0.91 | 4.19 | 0.89 |

A composition containing microcapsules with a shell comprising the terpolymer according to entry 1 was perceived white and was taken as reference for the measurement of the relative colour difference (ΔE).

If ΔE is below 3, it is not possible to differentiate the colour by human eye. The slurry containing microcapsules according to entries 1 and 3 are both perceived white. In contrast, the slurry containing microcapsules according to entry 2 is perceived light yellow. A composition containing microcapsules with a shell made of melamine-formaldehyde pre-condensate and urea, the shell having 1 or 2 layers, is colourless.

EXAMPLE 3

Leakage Stability

To determine the leakage stability of the encapsulated perfume compositions in laundry detergents, the corresponding slurries containing 0.1% of the microcapsules were placed in a 5% solution of sodium dodecyl sulfonate (SDS) at 50° C. for 3 days. SDS is a typical surfactant present in liquid and powder detergents.

The leakage stability of the encapsulated perfume compositions in a bleach environment was tested by placing the corresponding slurries containing 0.1% of the microcapsules in a 6% solution of $H_2O_2$ at pH 9 (adjusted with NaOH) at room temperature for 3 days.

After exposure, the microcapsules were analysed under an optical microscope to evaluate their stability.

TABLE 2

| Entry | Terpolymer | No. of shell layers | % of nominal fragrance level in the capsule after 3 days at 50° C. | |
|---|---|---|---|---|
| | | | Surfactant (5% SDS) | Bleach (6% $H_2O_2$) |
| 1 | Melamine-formaldehyde pre-condensate + urea | 2 | 75 | 75 |
| 2 | melamine - resorcinol - formaldehyde | 2 | 75 | 25 |
| 3 | melamine-formaldehyde pre-condensate + urea | 1 | 25 | 25 |
| 4 | melamine-formaldehyde pre-condensate + urea (post added) | 2 | No sufficient encapsulation, free fragrance still present at the end of the process | |

Microcapsules with a shell comprising 2 layers made of melamine-formaldehyde pre-condensate and urea are very stable in bleach environment compared to similar microcapsules containing resorcinol instead of urea. They are also stable in detergents comprising surfactants.

In entry 4, urea was post-added after microcapsule formation. By this change, no sufficient encapsulation took place. At the end of the process, there was still free fragrance present in the mixture.

EXAMPLE 4

Amount of Urea

The ratio of urea to melamine-formaldehyde pre-condensate used in the encapsulation process was varied to determine the most stable microcapsule system, in particular the most stable in terms of leakage stability in surfactant-containing bases. All microcapsules of samples 3 to 7 were provided with a shell of 2 layers and a deposition aid. Samples 1 and 2 were prepared as reference samples. Sample 1 was prepared according to EP 2111214, with a resorcinol to melamine weight ratio of 0.8. For sample 2, the melamine pre-condensate was added first and the urea was post-added after microcapsule formation.

In all cases, the percentage melamine-formaldehyde pre-condensate and the percentage of perfume in the slurry were held constant (melamine: 8.7% by weight of slurry, perfume 38% by weight of slurry). This means that the terpolymer to perfume ratio (which is the core-shell ratio) increased between sample 3 and 7. The solid content was gravimetrically at 160° C., using a Moisture Analyzer HB 43, Mettler Toledo, until weight constancy was reached, i.e. when the variation of the weight was less than 1 mg within 20 seconds.

TABLE 3

| Entry | Urea to melamine-formaldehyde pre-condensate ratio[1] | Solid content in slurry (%) | % Leakage in 5% SDS solution[2] |
|---|---|---|---|
| 1 (reference, with resorcinol) | — | 38.0 | 15 |
| 2 (urea post-added) | 1.1 | Poor capsule formation | — |
| 3 | 0.55 | 41.0 | 15 |
| 4 | 1.1 | 42.0 | 5 |
| 5 | 2.6 | 43.0 | 70 |

TABLE 3-continued

| Entry | Urea to melamine-formaldehyde pre-condensate ratio[1] | Solid content in slurry (%) | % Leakage in 5% SDS solution[2] |
|---|---|---|---|
| 6 | 4.5 | 46.0 | 90 |
| 7 | 5.6 | 37.4 | 100 |

[1] weight percent ratio.
[2] after 3 days at 50° C. in 5% SDS aqueous solution. The leakage is expressed as a percentage of the nominal perfume level in the system, assuming the whole perfume has been encapsulated.

As can be seen from the data summarised in table 3, the microcapsules with a good stability with respect to perfume leakage is obtained with an urea to melamine-formaldehyde pre-condensate percentage ratio of 1.1 (entry 4).

If the relative amount of urea is reduced by half, the stability with respect to perfume leakage is slightly diminished (entry 3). If the relative amount of urea is doubled (entry 5) or further increased, the leaking stability drops significantly.

Microcapsules with a shell comprising the terpolymer having an urea to melamine-formaldehyde pre-condensat-eratio of about 0.5 to 1.5 are particularly of about 0.8 to 1.2 are preferred.

As demonstrated by other examples, the leakage values of capsules having above urea to melamine-formaldehyde pre-condensate ratios are comparable to those of capsule comprising resorcinol (entry 1). When urea is post added to the reaction mixture (entry 2), only insufficient perfume encapsulation occurs. The results also teach that increasing simultaneously the level of urea in the polymer and the amount of polymer in the system, does not improve the stability of the capsules with respect to leakage in aqueous surfactant solutions.

EXAMPLE 5

Microcapsule Leakage in Liquid Detergent Pouches

The perfume compositions disclosed in Table 4 and Table 5 were encapsulated using the process disclosed in example 1 with an urea to melamine-formaldehyde pre-condensate ratio of 1.1. In each case, an amount of slurry equivalent to 0.2 wt % of perfume-containing capsules was added to a liquid detergent tab base composition having the formula described in Table 2.2.

TABLE 4

Perfume composition A

| RECON_VOLTAE Distribution | C [%] | Average RECON_VOLTAE [Bohr$^3$] |
|---|---|---|
| RECON_VOLTAE > 1750 | 18.6 | 1845 |
| 1540 < RECON_VOLTAE < 1750 | 22.3 | 1666 |
| 1200 < RECON_VOLTAE < 1750 | 53.7 | 1386 |
| RECON_VOLTAE < 1200 | 5.5 | 1100 |

Perfume A had 5.5 wt % of ingredients having RECON_VOLTAE lower than 1200; 94.5 wt % of ingredients having RECON_VOLTAE higher than 1200; 40.9 wt % of ingredients having RECON_VOLTAE higher than 1540; and 18.6 wt % of ingredients having RECON_VOLTAE higher than 1750. In table 2.1.1, all averages are weighted averages. RECON_VOLTAE <1200 means that RECON_VOLTAE can have any value between from 1 to 1199; 1200 <RECON_VOLTAE <1540 means that RECON_VOLTAE can have any value between 1200 and 1539. RECON_VOLTAE >1750 means that RECON_VOLTAE can have any value between from 1750 upwards.

TABLE 5

Perfume composition B

| RECON_VOLTAE Distribution | C [%] | Average RECON_VOLTAE [Bohr$^3$] |
|---|---|---|
| RECON_VOLTAE > 1750 | 6.6 | 1966 |
| 1540 < RECON_VOLTAE < 1750 | 59.9 | 1677 |
| 1200 < RECON_VOLTAE < 1540 | 26.4 | 1374 |
| RECON_VOLTAE < 1200 | 7.1 | 1155 |

Perfume B had 7.1 wt % of ingredients having RECON_VOLTAE lower than 1200; 92.9 wt % of ingredients having RECON_VOLTAE higher than 1200; 66.5 wt % of ingredients having RECON_VOLTAE higher than 1540; and 6.6 wt % of ingredients having RECON_VOLTAE higher than 1750. RECON_VOLTAE <1200 means that RECON_VOLTAE can have any value between from 1 to 1199; 1200<RECON_VOLTAE<1540 means that RECON_VOLTAE can have any value between 1200 and 1539. RECON_VOLTAE>1750 means that RECON_VOLTAE can have any value between from 1750 upwards.

TABLE 6

Liquid detergent tab base composition

| Ingredient | Chemical nature | Percentage |
|---|---|---|
| DEIONIZED WATER | | 10 wt % |
| PROPYLENE GLYCOL (ex MERCK) | | 20 wt % |
| GLYCEROL (ex Merck) | Propan-1,2,3 triol | 18.5 wt % |
| TEXAPON N 70 (ex COGNIS) | Sodium Lauryl Ether Sulfate + 2EO | 16.33 wt % |
| BIO SOFT LA ACID (ex STEPAN) | Acid benzenesulfonic | 5 wt % |
| LASACID FC 12 (ex LASCARAY SA) | Lauric acid 99% | 5 wt % |
| M.E.A (ex BASF) | Monoethanolamine | 10 wt % |
| NEODOL 25-7 (ex CALDIC) | Ethoxylated Alcohol C12-C15 | 15 wt % |
| BRONIDOX L (ex COGNIS) | 2-bromo-2-nitropropane | 0.03 wt % |

The liquid detergent base containing above perfume compositions were put in a thermostated cupboard at 37° C. for one month and the amount of free perfume having leached from the capsules was determined using the method describedbelow.

Determination of Capsule Leakage in Consumer Product Bases 1 g of consumer product base sample, previously filtered through a 5 micrometre syringe filter was accurately weighed in a 30 ml flask. 1 g of Celite 545 was added and admixed with the sample. 10 ml of pentane was then added together with 0.5 mg of internal standard (Methyl decanoate 99% Aldrich ref 299030) to the sample. The whole was stirred for 30 minutes using a magnetic stirrer. The pentane phase was then removed and an aliquot of 2 microlitre was injected in a gas chromatograph (GC) equipped with a splitless injector and a flame ionization detector. The initial temperature of the GC oven was 70° C., the final temperature, 240° C. and the rate of hating was set to 2° C./min. The temperature of the injector was 250° C. A RTX1 GC column with dimensions 60 m*0.25 µm*0.25 µm was used. Table 7 summarizes the results from capsule leakage analysis, along with RECON_VOLTAE values.

TABLE 7

| Perfume Composition | Ingredients with RV > 1200 (wt %) | Ingredients with 1200 < RV < 1540 (wt %) | Ingredients with RV > 1540 (wt %) | Ingredients with RV > 1750 (wt %) | LEAKAGE 1 month 37° C. (wt %) |
|---|---|---|---|---|---|
| Perfume A | 94.5 | 53.7 | 40.9 | 18.6 | 50 |
| Perfume B | 92.9 | 26.4 | 66.5 | 6.6 | 15 |

The results show that, provided an encapsulated perfume having a distribution of RECON_VOLTAE values (Perfume B) and an urea to melamine-formaldehyde pre-condensate ratio according to the present invention are used, the obtained microcapsules are stable in a liquid detergent composition typically used in liquid detergent pouches (or so-called liquid tabs).

The invention claimed is:

1. An encapsulated perfume composition comprising at least one aminoplast core-shell microcapsule dispersed in a suspending medium, the microcapsule comprising a perfume-containing core encapsulated in a shell, said shell comprising a network of cross-linked aminoplast resin, wherein 75-100 wt % of the resin comprises 50-90 wt % of a terpolymer and from 10-50 wt % of a polymeric stabilizer; the terpolymer comprising:
   (a) from 20-35 wt % of moieties derived from at least one triamine,
   (b) from 30-60 wt % of moieties derived from at least one diamine,
   (c) from 20-35 wt % of moieties derived from the group consisting of alkylene and alkylenoxy moieties having 1 to 6 methylene units,
   wherein the terpolymer comprising the moieties a), b) and c) is a condensation product of an amino-aldehyde pre-condensate cross-linked with a diamine,
   wherein said terpolymer comprises less than 2 wt % of aromatic polyols based on the weight of the shell,
   and wherein the microcapsule is a bilayer microcapsule.

2. The encapsulated perfume composition according to claim 1, wherein the amino-aldehyde pre-condensate is a melamine-formaldehyde pre-condensate.

3. The encapsulated perfume composition according to claim 1, wherein the at least one diamine is selected from the group consisting of urea and 3-substituted 1,5-diamino-2,4,6-triazin.

4. The encapsulated perfume composition according to claim 1, which is colourless upon visual inspection, and has a ΔE value of 3 or less on the CIELAB scale.

5. The encapsulated perfume composition according to claim 1, wherein the terpolymer further comprises an aromatic polyol.

6. The encapsulated perfume composition according to claim 5, wherein the aromatic polyol is selected from the group consisting of resorcinol, phenol, 3,5-dihydroxy toluene, bisphenol A, hydroquinone, xylenol, polyhydroxy naphthalene and polyphenols produced by the degradation of cellulose and humic acids.

7. The encapsulated perfume composition according to claim 1, wherein 75-100 wt % of the resin comprises from 60-85 wt % of the terpolymer and from 10-25 wt %, of the polymeric stabilizer.

8. The encapsulated perfume composition according to claim 1, wherein the terpolymer comprises:
   (a) from 22-30 wt % of moieties derived from at least one triamine,
   (b) from 40-55 wt % of moieties derived from at least one diamine, and
   (c) from 22-30 wt % of moieties derived from the group consisting of alkylene and alkylenoxy moieties having 1 to 6 methylene units.

9. The encapsulated perfume composition according to claim 1, wherein the moieties derived from the group consisting of alkylene and alkylenoxy moieties have 1 to 4 methylene units.

10. A method of forming an encapsulated perfume composition as defined in claim 1, comprising the steps of forming an oil-in-water emulsion comprising at least one perfume-containing oil droplet dispersed in an aqueous continuous phase, the continuous phase containing amino-aldehyde pre-condensate and diamine cross-linker; and at a pH of 4.6±2, raising the temperature of the emulsion to an elevated temperature, causing the amino-aldehyde pre-condensate and diamine to undergo polycondensation and cross-linking reactions, thereby to form a cross-linked aminoplast resin shell around the droplet.

11. The method according to claim 10, wherein the elevated temperature is 88° C.±1° C.

12. The method according to claim 10, wherein the temperature is elevated to 88° C.±1° C. over a time period of more than 1 hour.

13. The method according to claim 10, wherein at the elevated temperature the pH is reduced and further amino-aldehyde pre-condensate is added to form a second layer.

14. A fragranced personal care, household, washing and cleaning product comprising the encapsulated perfume composition according to claim 1.

15. The fragranced product according to claim 14, selected from laundry solid and liquid detergents and liquid fabric softeners and conditioners.

16. The fragranced product according to claim 14, in which the product further contains non-encapsulated perfume.

17. The fragranced product according to claims 14, further comprising unstructured surfactants.

18. The fragranced product according to claims 14, further comprising bleaches.

19. The fragranced product according to claim 14 provided in a one dose unit form.

* * * * *